(12) United States Patent
Stahl et al.

(10) Patent No.: US 10,030,251 B2
(45) Date of Patent: Jul. 24, 2018

(54) TRANSGENIC PLANT OF THE SPECIES SOLANUM TUBEROSUM WITH RESISTANCE TO PHYTOPHTHORA

(71) Applicant: KWS SAAT AG, Einbeck (DE)

(72) Inventors: Jurgen Dietmar Stahl, Einbeck (DE); Nora Temme, Munster (DE)

(73) Assignee: KWS SAAT SE, Einbeck (DE)

( * ) Notice: Subject to any disclaimer, the term of this patent is extended or adjusted under 35 U.S.C. 154(b) by 279 days.

(21) Appl. No.: 14/420,106

(22) PCT Filed: Aug. 6, 2013

(86) PCT No.: PCT/DE2013/000446
§ 371 (c)(1),
(2) Date: Feb. 6, 2015

(87) PCT Pub. No.: WO2014/023285
PCT Pub. Date: Feb. 13, 2014

(65) Prior Publication Data
US 2015/0225738 A1    Aug. 13, 2015

(30) Foreign Application Priority Data

Aug. 8, 2012    (DE) .................. 10 2012 016 009

(51) Int. Cl.
*C12N 15/82*    (2006.01)
*C12N 15/113*    (2010.01)

(52) U.S. Cl.
CPC ........ *C12N 15/8282* (2013.01); *C12N 15/113* (2013.01); *C12N 2310/14* (2013.01); *C12N 2310/141* (2013.01)

(58) Field of Classification Search
CPC ................................. C12N 15/8282
USPC ................................. 800/279, 285
See application file for complete search history.

(56) References Cited

U.S. PATENT DOCUMENTS

| | | | |
|---|---|---|---|
| 8,299,318 B2 | 10/2012 | Brover et al. | |
| 2010/0257634 A1 | 10/2010 | Bailey et al. | |
| 2011/0167514 A1 | 7/2011 | Brover et al. | |
| 2015/0082495 A1* | 3/2015 | Delebarre | C12N 15/1137 800/312 |

FOREIGN PATENT DOCUMENTS

| | | |
|---|---|---|
| CN | 101107362 A | 1/2008 |
| DE | 102012016009 A1 | 2/2014 |
| EP | 1716238 A1 | 11/2006 |
| WO | 2006047495 A2 | 5/2006 |
| WO | 2006070227 A2 | 7/2006 |
| WO | 2009112270 A2 | 9/2009 |
| WO | 2014023285 A2 | 2/2014 |

OTHER PUBLICATIONS

Fourgoux-Nicol et al 1999, Plant Molecular Biology 40 :857-872.*
Thomas et al. 2001, The Plant Journal 25(4):417-425.*
Pieter van West, et al., "Internuclear Gene Silencing in Phytophthora Infestans", Molecular Cell 3(3): 339-348 (1999).
International Search Report for PCT/DE2013/000446 dated Mar. 11, 2014.
International Preliminary Report on Patentability and Written Opinion for PCT/DE2013/000446 dated Feb. 10, 2015.
Jan. 28, 2005 "PE006G1 mycelium, carbon starvation Phytophthora infestans cDNA, mRNA sequence.", XP002717637 retrieved from EBI accession No. EM_EST:CV909836, Database accession No. CV909836 sequence.
Nov. 15, 2012 "Sequence 12097 from Patent U.S. Pat. No. 8,299,318.", retrieved from EBI accession No. EM_PAT: GZ562039, Database accession No. GZ562039 sequence.
Avrova AO, Boevink PC, Young V, Grenville-Briggs LJ, van West P, Birch PR, Whisson SC (2008) a novel Phytophthora infestans haustorium-specific membrane protein is required for infection of potato. Cell Microbiol. 10 (11):2271-84.
Birch RG, Shen B, Sawyer BJ, Huttner E, Tucker WQ, Betzner AS (2010) Evaluation and application of a luciferase fusion system for rapid in vivo analysis of RNAi targets and constructs in plants. Plant Biotechnol J. May 1;8(4):465-75. Epub Jan. 19, 2010.
Blackman LM, Arikawa M, Yamada S, Suzaki T, Hardham AR (2011) Identification of a mastigoneme protein from Phytophthora nicotianae. Protist. 162(1):100-14.
Benfey, P. N., Ren, L., and Chua, N.-H. (1990). Combinatorial and synergistic properties of CaMV 35S enhancer subdomains. EMBO J. (9), 1685-1696.
Chomczynski P, Sacchi N. (1987) Single-step method of RNA isolation by acid guanidinium thiocyanate-phenol-chloroform extraction. Anal Biochem.162(1):156-9.
Eckes P., Rosahl S., Schell J., Willmitzer L. (1986) Isolation and characterization of a light-inducible, organ-specific gene from potato and analysis of its expression after tagging and transfer into tobacco and potato shoots. Molecular and General Genetics 205 (1) 14-22, DOI: 10.1007/BF02428027.
Fire A, Xu S, Montgomery MK, Kostas SA, Driver SE, Mello CC. (1998) Potent and specific genetic interference by double-stranded RNA in Caenorhabditis elegans. Nature Feb. 19;391(6669):806-11.
Grenville-Briggs LJ, Avrova AO, Bruce CR, Williams A, Whisson SC, Birch PR, van West P (2005) Elevated amino acid biosynthesis in Phytophthora infestans during appressorium formation and potato infection. Fungal Genet Biol. 42 (3):244-56.
Inoue SB, Takewaki N, Takasuka T, Mio T, Adachi M, Fujii Y, Miyamoto C, Arisawa M, Furuichi Y, Watanabe T (1995) Characterization and gene cloning of 1,3-beta-D-glucan synthase from *Saccharomyces cerevisiae*. Eur J Biochem 231 (3):845-54.

(Continued)

*Primary Examiner* — Li Zheng
(74) *Attorney, Agent, or Firm* — Troutman Sanders LLP

(57) ABSTRACT

The present invention concerns a transgenic plant of the species *Solanum tuberosum* with a resistance to an oomycete of the genus *Phytophthora*, transgenic parts of such a plant, a method for its manufacture and to a composition for external application to plants. On the one hand, nucleotide sequences in accordance with SEQ ID NOS: 1-43 are provided from *Phytophthora* in a host plant-induced gene silencing strategy in potato plants; on the other hand, a fungicide for plant treatment is provided.

15 Claims, 33 Drawing Sheets

(56) References Cited

OTHER PUBLICATIONS

Figure 1:
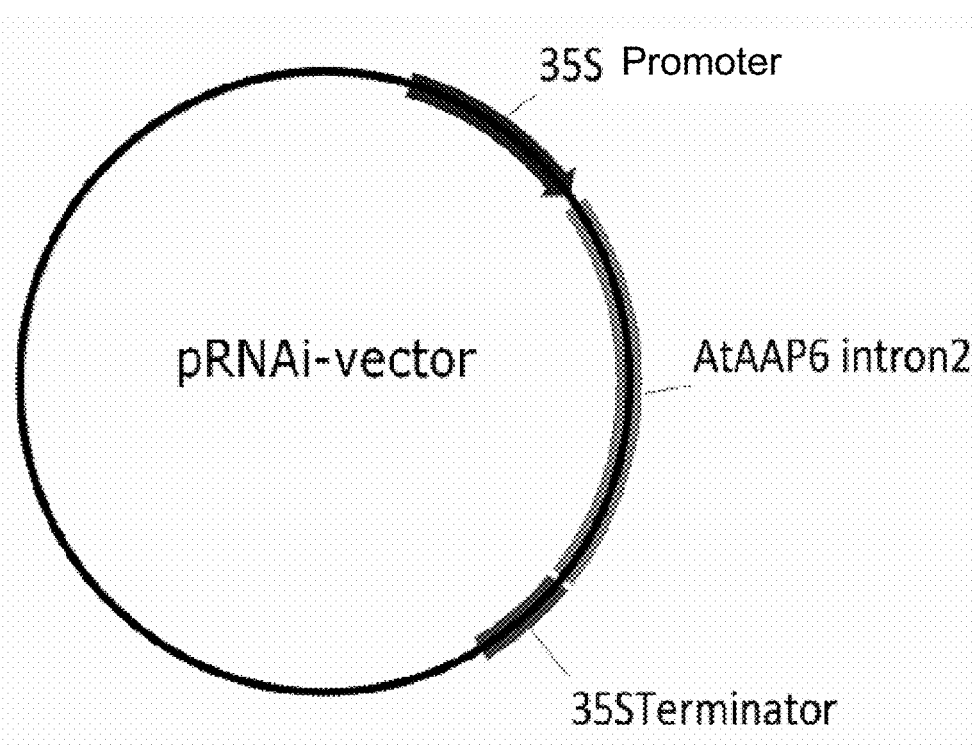

Judelson HS, Narayan RD, Ah-Fong AM, Kim KS (2009a) Gene expression changes during asexual sporulation by the late blight agent Phytophthora infestans occur in discrete temporal stages. Mol Genet Genomics. 281(2)193-206.

Judelson HS, Tani S, Narayan RD (2009b) Metabolic adaptation of Phytophthora infestans during growth on leaves, tubers and artificial media. Mol Plant Pathol. 10(6):843-55.

Kamoun S, van West P, Vleeshouwers VG, de Groot KE, Govers F. (1998) . Resistance of nicotiana benthamiana to phytophthora infestans is mediated by the recognition of the elicitor protein INF1. Plant Cell. Sep;10(9):1413-26.

Lesage G, Sdicu AM, Ménard P, Shapiro J, Hussein S, Bussey H (2004) Analysis of beta-1,3-glucan assembly in *Saccharomyces cerevisiae* using a synthetic interaction network and altered sensitivity to caspofungin. Genetics. May;167(1):35-49.

Li A, Wang Y, Tao K, Dong S, Huang Q, Dai T, Zheng X, Wang Y (2010) PsSAK1, a Stress-Activated MAP Kinase of Phytophthora sojae, Is Required for Zoospore Viability and Infection of Soybean. Mol Plant Microbe Interact. 23 (8):1022-31.

Mazur P, Morin N, Baginsky W, el-Sherbeini M, Clemas JA, Nielsen JB, Foor F (1995) Differential expression and function of two homologous subunits of yeast 1,3-beta-D-glucan synthase. Mol Cell Biol. 15(10):5671-81.

Pel MA, Foster SJ, Park TH, Rietman H, van Arkel G, Jones JDG, Van Eck HJ, Jacobsen E, Visser RGF, Van der Vossen EAG (2009) Mapping and cloning of late blight resistance genes from Solanum venturii using an interspecific candidate gene approach. MPMI 22:601-615.

Roemer T, Paravicini G, Payton MA, Bussey H (1994) Characterization of the yeast (1→6)-beta-glucan biosynthetic components, Kre6p and Skn1p, and genetic interactions between the PKC1 pathway and extracellular matrix assembly. J Cell Biol. 127(2):567-79.

Saito, K., Yamazaki, M., Kaneko, H., Murakoshi, I., Fukuda, Y., and van Montagu, M. (1991). Tissue-specific and stress-enhancing expression of the TR promoter for mannopine synthase in transgenic medicinal plants. Planta 184, 40-46.

Schmidt K., Heberle B., Kurrasch J., Nehls R., Stahl D.J. (2004) Suppression of phenylalanine ammonia lyase expression in sugar beet by the fungal pathogen Cercospora beticola is mediated at the core promoter of the gene. Plant Mol. Biol., 55: 835-852.

Stahl D. J., Kloos, D. U., and Hehl, R. (2004). A sugar beet chlorophyll alb binding protein void of G-box like elements confer strong and leaf specific reporter gene expression in transgenic sugar beet. BMC Biotechnology 4;31: 12.

Vancanneyt G., Schmidt R., O'Connor-Sanchez A., Willmitzer L., Rocha-Sosa M. (1990) Construction of an intron-containing marker gene: splicing of the intron in transgenic plants and its use in monitoring early events in Agrobacterium-mediated plant transformation. Mol Gen Genet. 220(2):245-50.

Van West P, Kamoun S, van 't Klooster JW, Govers F (1999) Internuclear gene silencing in Phytophthora infestans. Mol Cell. Mar;3(3):339-48.

Wang Y, Dou D, Wang X, Li A, Sheng Y, Hua C, Cheng B, Chen X, Zheng X, Wang Y (2009) the PsCZF1 gene encoding a C2H2 zinc finger protein is required for growth, development and pathogenesis in Phytophthora sojae. Microb Pathog. 47(2):78-86.

Wang Y, Li A, Wang X, Zhang X, Zhao W, Dou D, Zheng X, Wang Y (2010) GPR11, a putative seven-transmembrane G protein-coupled receptor, controls zoospore development and virulence of Phytophthora sojae. Eukaryot Cell 9 (2):242-50.

Yin C, Jurgenson J E, Hulbert S H (2011) Development of a Host-Induced RNAi System in the Wheat Stripe Rust Fungus *Puccinia striiformis* f. sp. *Tritici*. MPMI 24(5): 554-561. doi:10.1094/MPMI-10-1 0-0229. © 2011 The American Phytopathological Society.

Zhang M, Wang Q, Xu K, Meng Y, Quan J, et al. (2011) Production of dsRNA Sequences in the Host Plant is Not Sufficient to Initiate Gene Silencing in theColonizing Oomyzete Pathogen Phytothhora parasitica. PLoS ONE 6(11): e28114.

Catalanotto, C. et al., "Involvement of small RNAs and role of the qde genes in the gene silencing pathway in Neurospora", Research Communication, Genes & Development (2002), vol. 16, pp. 790-795.

Koch, A. et al., "New wind in the sails: improving the agronomic value of crop plants through RNAi-mediated gene silencing", Plant Biotechnology Journal (2014), vol. 12, pp. 821-831.

Loke, S. L, et al., "Characterization of oligonucleotide transport into living cells", Proc. Natl. Acad., Sci. (1989), vol. 86, pp. 3474-3478.

Meister, G. et al., "Mechanisms of gene silencing by double-stranded RNA", Nature (2004), vol. 431, pp. 343-349.

Randall, T.A. et al., "Large-Scale Gene Discovery in the Oomycete Phytophthora infestans Reveals Likely Components of Phytopathogenicity Shared with True Fungi", MPMI (2005), vol. 18, No. 3, pp. 229-243; EBI accession No. CV909836.

\* cited by examiner

US 10,030,251 B2

TRANSGENIC PLANT OF THE SPECIES SOLANUM TUBEROSUM WITH RESISTANCE TO PHYTOPHTHORA

CROSS REFERENCE TO RELATED APPLICATIONS

This application is a U.S. National Phase Application under 35 U.S.C. § 371 of International Patent Application PCT/DE2013/000446 filed Aug. 6, 2013 which claims priority to German Patent Application 10 2012 016 009.7 filed Aug. 8, 2012. The International Application was published on Feb. 13, 2014, as International Publication No. WO 2014/023285 under PCT Article 21(2). The entire contents of these applications are hereby incorporated by reference.

SEQUENCE LISTING

The instant application contains a Sequence Listing which has been submitted electronically in ASCII format and is hereby incorporated by reference in its entirety. Said ASCII copy, created on Jan. 15, 2015, is named 245761.000009_SL.txt and is 100,249 bytes in size.

BACKGROUND OF THE INVENTION

The present invention relates to a transgenic plant of the species *Solanum tuberosum* with a resistance to an oomycete of the genus *Phytophthora*, to transgenic parts a plant of this type, to a method for its manufacture and to a means for external application to plants.

Even now, potato late blight caused by *Phytophthora infestans* is still the most prevalent and most economically important potato disease.

Throughout the globe, the pathogen results in loss of earnings, with harvest losses of more than 20 percent. This means that expensive chemical plant protection means have to be used, because the natural defence mechanisms of the potato with the help of which *P. infestans* is combatted or with which propagation can be slowed down and restricted is not sufficient or not permanent.

Natural plant defence mechanisms, such as the hypersensitive reaction at the infection site, lignification of the cell wall, the production of PR (pathogenesis-related) proteins and the synthesis of phytoalexins are indeed known to contribute to augmenting resistance, but they are always accompanied by an energy loss and thus a loss of earnings for affected plants.

Natural defence mechanisms in plants also include the expression of so-called resistance genes (R genes), the gene products of which interact with microbial avirulence genes (Avr genes) (gene for gene hypothesis) and thus induce a specific defence reaction. This resistance can, however, be interrupted if a pathogen such as *P. infestans* can dispense with the synthesis of the Avr gene and recognition of the pathogen and thus the subsequent specific defence reaction in the plant host does not occur.

Fire et al. (1998) have already demonstrated that double stranded RNA (dsRNA) can result in the sequence-specific degradation of homologous RNA. Starting from these results, transgenic plants have been developed in the meantime which, with the aid of RNA interference (RNAi) by means of host plant-induced silencing of conserved and essential genes, for example from nematodes or *Lepidoptera*- and *Coleroptera* species, can exhibit resistance to these pests in vitro as well as in vivo.

In addition, the host plant-phytopathogenic fungus interaction can constitute an application of the concept of host-induced gene silencing (HIGS) to induce resistance (EP 1 716 238).

Van West et al. (1999) initially used the gene silencing method in *Phytophthora*, in order to carry out functional analyses of these oomycete-specific genes.

In WO 2006/070227, the use of RNA interference to control fungal pathogens based on contact of dsRNA with fungal cells outside the fungal cell was described for the first time. It proposes a method for the manufacture of a pathogen-resistant plant. In this manner, the RNA interference can be directed against one or more genes of a pathogen as well as several pathogens. *Phytophthora infestans* is mentioned as a possible fungal pathogen and potato as a possible host plant.

Previous studies have given rise to the hypothesis that host plant-induced gene silencing does not work for every gene and choice of the target gene is essential for functional silencing. Thus, for example, the plasma membrane H+-ATPase PnMA1 in *Phytophthora parasitica* could not be reduced sufficiently by host plant-induced gene silencing to deliver efficient protection against a pathogen (Zhang et al. 2011). According to this, selection of the target genes is also decisive for effective pathogen defence (Yin et al. 2011).

Recently, a screening system was proposed which was supposed to facilitate the selection of suitable parasitic genes for silencing constructs for the production of pathogen-resistant plants (US 2010/0257634). The identification of appropriate test constructs to induce phytoresistance in potato was also proposed by the authors. In this regard, target genes were defined based on bioinformatic analyses of genome sequences or based on sequence homologies to essential genes or virulence factors from known model organisms. That document does not contain any indications of the genes disclosed in the present invention for the generation of a resistance against an oomycete of the genus *Phytophthora*.

A method for producing a broad spectrum resistance in transgenic plants against multiple fungi is described in WO 2009/112270. In one implementation of the method of that invention, the broad spectrum resistance is directed against *Uncinula necator*, *Plasmopora viticola*, *Uromyces* spec., *Phakopsora pachyrhizi*, *Erysiphe* sp. and also *P. infestans*.

Furthermore, the development of *Phytophthora infestans*-resistant potato plants through RNAi-induced silencing is disclosed in WO 2006/047495. On the one hand, plants were generated which carry gene sequences of the rRNA gene from *Phytophthora infestans* for RNA interference. The silencing construct described in WO 2006/047495 directed against the rRNA gene of *Phytophthora infestans* comprises base pairs 1-600 of Accession number AJ854293 and with it 32 bp of the coding region of the 18S rRNA as well as the complete coding region of the 5.8 S rRNA gene of the blight pathogen. When selecting the target genes for HIGS strategies, with a view to applicability, it is vital that it has as short as possible or preferably no homologies extending over more than 17 sequential base pairs to the gene sequences of non-target organisms, as if there were, gene expression of the non-target organisms in the case of consumption of the transgenic plant or its harvest product could be destroyed ("off-target" effect). However, the sequence described in in WO 2006/047495 comprises 32 bp of the *P. infestans* 18S rRNA, which has 100% identity with the homologous sequence of the 18S rRNA gene from man (*Homo sapiens*), pigs (*Sus scrofa*) and cattle (*Bos taurus*). Human potato consumption in Asia in 2005 was 26 kg, in North America it was 58 kg and in Europe it was 96 kg per person (FAOSTAT). In the light of the high human and animal consumption of potatoes, the rRNA sequences from *Phytophthora infestans* described in WO 2006/047495 as HIGS target genes are unsuitable for consumers on safety grounds.

On the other hand, in WO 2006/047495, plants were produced that carry gene sequences for the cathepsin B gene from *Myzus persicae* and the elicitin gene INF1 from *P. infestans* for RNA interference and thus exhibit resistance to two plant pathogens. The target gene INF1 used therein codes for an elicitor. A resistance based on an elicitor as a pathogenicity factor is a disadvantage because the elicitin gene INF1 is not always necessary for an infection of potatoes by *Phytophthora infestans* (Kamoun et al. 1998).

BRIEF SUMMARY OF THE INVENTION

The aim of the present invention is thus to provide a transgenic plant of the species *Solanum tuberosum* which is pathogen-resistant to an oomycete of the genus *Phytophthora* and in particular is suitable for consumption.

In accordance with the invention, this aim is accomplished by the fact that a double-stranded first and second DNA are stably integrated into the transgenic plant, wherein the first DNA comprises (a) a nucleotide sequence in accordance with SEQ ID NOS: 1-43, or (b) a fragment of at least 15 successive nucleotides of a nucleotide sequence in accordance with SEQ ID NOS: 1-43, or (c) a nucleotide sequence which is complementary to one of the nucleotide sequences of (a) or (b), or (d) a nucleotide sequence which hybridizes with one of the nucleotide sequences of (a), (b) or (c) under stringent conditions.

Surprisingly, it has been found that a first DNA of this type is particularly suitable for conferring a pathogen resistance in potato plants via a host-induced gene silencing strategy.

The first and the second DNA are integrated in a stable manner into the genome of a transgenic plant of the species *Solanum tuberosum*. Preferably, the DNAs are integrated in a stable manner into a chromosome of the plant. However, they can also be integrated into an extra-chromosomal element. The advantage of stable integration is that the DNA can be passed on to subsequent generations of the transgenic plant.

The double-stranded DNA is composed of a coding and a non-coding strand.

Furthermore, the nucleotide sequence of the coding strand of the second DNA is the reverse complement of the nucleotide sequence of the coding strand of the first DNA. The term "reverse complement" with respect to a nucleotide sequence in the 5'-3' direction should be understood to mean a nucleotide sequence in the 3'-5' direction wherein, in accordance with the base pairing rules, the bases correspond to the bases of the first DNA and are in a reverse/mirrored sequence. If the nucleotide sequence of the coding strand of the first DNA is atggttc, for example, then the reverse complementary nucleotide sequence of the coding strand of the second DNA is gaaccat. This is also known as sense and corresponding antisense (reverse complementary) orientation of the nucleotide sequences.

In particular, the nucleotide sequence of the coding strand of the second DNA can be the reverse complement of the nucleotide sequence of the coding strand of the first DNA over the whole length of the sequence. However, it can also be only partially reverse complementary, i.e. reverse complementary over a limited length. The nucleotide sequence of the coding strand of the second DNA can also be reverse complementary in more than one region, for example in two or three regions of its nucleotide sequence to the nucleotide sequence of the coding strand of the first DNA.

Starting from the completely or partially reverse complementary nucleotide sequences for the coding strand of the first and second DNA, a double-stranded RNA is produced. The double-stranded structure of the RNA arises by the formation of bridging hydrogen bonds between complementary nucleotides. Double-stranded RNA regions may be formed over a single nucleic acid strand which is partially complementary to itself, or over two different, discontinuous complementary nucleic acid strands. The bridging hydrogen bond formation may thus be intramolecular as well as intermolecular.

In accordance with the invention, the first DNA comprises a nucleotide sequence in accordance with SEQ ID NOS: 1-43, wherein these sequences are nucleotide sequences from selected target genes from *Phytophthora infestans*. The group formed by these target genes comprises essential genes for primary metabolism as well as for amino acid synthesis, in particular the biosynthesis of aliphatic amino acids (valine, leucine, isoleucine) as well as for glutamate biosynthesis, genes for cell regulation and signal transduction as well as redox regulation, calcium signalling, G-protein signalling, MAP-kinase signalling and transcription factors, as well as genes for translation components, gene with RNA processing functions, genes which code for developmental and differentiation proteins such as, for example, with cell wall formation functions, as well as genes which code for transporters, channelling and membrane proteins. A summary of these target genes from *Phytophthora* which are used for designing the host-induced gene silencing is set out in Table 1.

TABLE 1

| ID | Target gene_ID | Function | Category | identification |
|---|---|---|---|---|
| 1 | PITG_03410 | Acetolactate synthase | Amino acid biosynthesis | A |
| 2 | PITG_00375 | Haustorium-specific membrane protein (Pihmp1) | Development/differentiation | D |
| 3 | PITG_13490 | Urokanase | Glutamate biosynthesis | C |
| 4 | PITG_00146 | Glucose-6-P-dehydrogenase | Primary metabolism | C |
| 5 | PITG_00561 | Ubiquinone- biosynthesis protein COQ9 | Primary metabolism | B |
| 6 | PITG_06732 | Acyl-CoA-dehydrogenase | Primary metabolism | B |
| 7 | PITG_07405 | Pyruvate kinase | Primary metabolism | B |
| 8 | PITG_12228 | NADH-cytochrome B5 reductase | Primary metabolism | B |
| 9 | PITG_15476 | Malate dehydrogenase | Primary metabolism | B |

TABLE 1-continued

| ID | Target gene_ID | Function | Category | identification |
|---|---|---|---|---|
| 10 | PITG_18076 | Phosphoglycerate mutase | Primary metabolism | B |
| 11 | PITG_19736 | Alcohol dehydrogenase | Primary metabolism | B |
| 12 | PITG_20129/ | Acyl-CoA-dehydrogenase | Primary metabolism | B |
| 13 | PITG_00221 | Tryptophan synthase | Amino acid biosynthesis | A |
| 14 | PITG_05318 | N-(5'-phosphoribosyl) anthranilate-isomerase | Amino acid biosynthesis | C |
| 15 | PITG_13139 | Threonine synthase | Amino acid biosynthesis | C |
| 16 | PITG_00578 | Imidazolone propionase | Glutamate biosynthesis | C |
| 17 | PITG_15100 | Histidine ammonium lyase | Glutamate biosynthesis | A |
| 18 | PITG_11044 | Protein phosphatase | Signal transduction | B |
| 19 | PITG_21987 | Protein phosphatase 2C | Signal transduction | B |
| 20 | PITG_01957 | Calcineurin-like catalytic subunit A | Calcium signalling | C |
| 21 | PITG_02011 | Calcineurin-subunit B | Calcium signalling | C |
| 22 | PITG_16326 | Calcineurin-like catalytic subunit A | Calcium signalling | C |
| 23 | PITG_00708 | Thioredoxin | Redox regulation | C |
| 24 | PITG_00715 | Thioredoxin | Redox regulation | C |
| 25 | PITG_00716 | Thioredoxin | Redox regulation | C |
| 26 | PITG_09348 | Glutaredoxin | Redox regulation | C |
| 27 | PITG_08393 | PsGPR11 G-protein coupled receptor | G-Protein signalling | D |
| 28 | PITG_10447 | SAPK homologue | MAP Kinase signalling | D |
| 29 | PITG_06748 | Myb-like DNA-binding protein | Transcription factor | A |
| 30 | PITG_19177 | C2H2-transcription factor (PsCZF1-homologue) | Transcription factor | D |
| 31 | PITG_06873 | Aspartyl-tRNA-synthetase | Translation | B |
| 32 | PITG_09442 | 40S Ribosomal protein S21 | Translation | B |
| 33 | PITG_16015 | Ribonuclease | RNA-processing | B |
| 34 | PITG_09306 | PnMas2- homologue | Development/differentiation | D |
| 35 | PITG_03335 | Callose synthase (Fks1/2-homologue) | Cell wall formation | D |
| 36 | PITG_05079 | Glycosyl transferase (Fks1/2-Homologue) | Cell wall formation | D |
| 37 | PITG_18356 | Beta-glucane synthesis-associated protein (KRE6-homologue) | Cell wall formation | D |
| 38 | PITG_09193 | Aquaporin | Channel | B |
| 39 | PITG_00562 | Mitochondrial tricarboxylate carrier | Transporter | B |
| 40 | PITG_08314 | ABC superfamily protein | Transporter | B |
| 41 | PITG_12289 | ATPase H- or Na-translocating F-type | Transporter | B |
| 42 | PITG_12999 | MFS superfamily transporter | Transporter | B |
| 43 | PITG_16478 | Acyl-CoA-dehydrogenase | Primary metabolism | B |

DETAILED DESCRIPTION OF THE INVENTION

The term "gene silencing" or silencing describes processes for switching genes off. Silencing can, for example, be transcriptional or post-transcriptional. Gene silencing also includes antisense technology, RNAi, or dsRNA.

The expression of a nucleotide sequence of a target gene in *Phytophthora infestans* is selectively inhibited by gene silencing. A target nucleotide sequence can in this case also be a non-processed RNA molecule, an mRNA or a ribosomal RNA sequence.

The target genes were identified by (i) publically available expression studies such as microarray data regarding oomycete differentiation or infection processes, for example, and publically available data on the investigation of metabolic processes during oomycete differentiation or infection (Grenville-Briggs et al. 2005, Judelson et al. 2009a, Judelson et al. 2009b) (A), (ii) comparative bioinformatic studies coupled with pedantic analysis (BioMax Bioinformatic Framework) (B), (iii) analyses of metabolic pathways coupled with pedantic analysis (C) as well as (iv) evaluations of publically available data regarding the characterization of homologous genes in eukaryotic organisms (Roemer et al. 1994, Inoue et al. 1995, Mazur et al. 1995, Lesage et al. 2004, Avrova et al. 2008, Wang et al. 2009, Li et al. 2010, Wang et al. 2010) (D).

When selecting the target genes, care was taken that the nucleotide sequence of these genes was specific for *P. infestans* in order to exclude unwanted silencing of plant and human genes. To this end, the selected target genes were compared as regards their proteins (BlastX) with the proteome of *Solanum tuberosum* and *Solanum lycopersicum*. At the same time, the target gene sequences were compared as regards their nucleotides (BlastN) with the genome of *Solanum tuberosum, Solanum lycopersicum* and a general BlastN (criteria: BlastN; database: human genomic+transcript; optimize for: somewhat similar sequences (blastn)). Target genes were considered to be highly suitable when they exhibited no nucleotide homologies with *Solanum tuberosum* and *Solanum lycopersicum* and no or only partial homologies in general BlastN in only short sequence regions (<17 nts), so that an interaction with endogenous plant nucleotide sequences was inhibited or did not occur.

In accordance with the invention, the nucleotide sequences used may have different lengths. Thus, the nucleotide sequences of one of SEQ ID NOS: 1-43 may, for example, have a length of between 501 and 735 nucleotides.

The nucleotide sequences used may also be one or more fragments of one or more nucleotide sequences of SEQ ID NOS: 1-43. In this regard, the fragments comprise at least 15, 16, 17, 18, 19, 20, 21, 22, 23, 24, 25, 30, 40, 50, 60, 70, 80, 90, 100, 150, 200, 250, 300, 350, 400, 450, 500, 550, 600, 650, 700, 750, 800, 850, 900, 950, 1000, 1100, 1200 or 1300, 1400, 1500, 1600, 1700, 1800, 1900, 2000, 2100, 2200, 2300, 2400 or 2500 successive nucleotides of one or more of the nucleotide sequences of SEQ ID NOS: 1-43. A particularly suitable fragment is a fragment of the nucleotide sequence of SEQ ID NO: 1 with 290 nucleotides.

In a preferred embodiment of the invention, combinations of two, three, four, five, six, seven, eight, nine, ten or more fragments of the same nucleotide sequence as that of SEQ ID NO: 1 or different nucleotide sequences such as those of SEQ ID NOS: 1, 2, 3, 4, 5, 6, 7, 8, 9, 10, 1, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or 43 are used. A preferred combination comprises fragments of the nucleotide sequences of SEQ ID NOS: 4, 23, 27 and 28, the genes of which are involved with signal transduction. A further preferred combination comprises fragments of nucleotide sequences of SEQ ID NOS: 3, 16 and 17; these are genes for glutamate biosynthesis from *P. infestans*. Further advantageous combinations comprise nucleotide sequences or fragments of nucleotide sequences from genes for cell wall formation (SEQ ID NOS: 25, 36, 37), calcium signalling (SEQ ID NOS: 20, 21, 22), primary metabolism genes (SEQ ID NOS: 5, 6, 7), redox regulation genes (SEQ ID NOS: 24, 25, 26), or comprise several nucleotide sequences or fragments of nucleotide sequences from transporter genes in accordance with SEQ ID NOS: 39, 40, 41, 42. Further preferred combinations comprise nucleotide sequences or fragments of nucleotide sequences of different target gene groups such as, for example, genes for G-protein signalling, MAP kinase signalling, primary metabolism and redox regulation (SEQ ID NOS: 27, 28, 4, 23). Combining several target genes means that the possibility that the resistance of the transgenic plant could be disrupted by a natural mutation in the oomycete is avoided.

The double-stranded first DNA introduced into the potato plant of the invention may comprise a nucleotide sequence which hybridizes under stringent conditions with one of the following nucleotide sequences: (a) a nucleotide sequence in accordance with SEQ ID NOS: 1-43, or (b) a fragment of at least 15 successive nucleotides of a nucleotide sequence in accordance with SEQ ID NOS: 1-43, or (c) a nucleotide sequence which is complementary to one of the nucleotide sequences of (a) or (b), or (c). Examples of stringent conditions are: hybridizing in 4×SSC at 65° C. and then washing several times in 0.1×SSC at 65° C. for approximately 1 hour in total. The term "stringent hybridization conditions" as used here can also mean: hybridization at 68° C. in 0.25 M sodium phosphate, pH 7.2 7% SDS, 1 mM EDTA and 1% BSA for 16 hours and subsequently washing twice with 2×SSC and 0.1% SDS at 68° C.

The present invention also in particular encompasses such fragments of nucleotide sequences which have a few, for example 1 or 2 nucleotides, which are not complementary to the target gene sequence from *Phytophthora infestans*. Sequence variations which, for example, occur in oomycetes, which are based on a genetic mutation, for example by addition, deletion or substitution or a polymorphism in a *Phytophthora infestans* strain and which result in wrong pairing over a region of 1, 2 or more nucleotides, can be tolerated as long as the RNA formed by the transgenic potato plant can still interfere with the target gene RNA formed by the oomycete.

In accordance with the invention, the transgenic plant of the species *Solanum tuberosum* confers a pathogen resistance to an oomycete of the genus *Phytophthora*. To determine the resistance, the transgenic potato plant is compared with a control plant which ideally has the identical genotype to the transgenic plant and has been grown under identical conditions, but which does not contain the DNA which has been introduced into the transgenic plant. The resistance can be determined using an optical score, wherein scores of 0 (not susceptible) to 100 (very susceptible) are awarded. Preferably, the transgenic plants of the invention confer a resistance which, compared with a control plant, results in a reduced propagation of infection over the plant surface of at least 10, 15, 20, 25, 30, 35, 40, 45, 50, 55, 60, 65, 70, 75, 80, 85, 90, 95, 100 percent (see the conditions under "measuring the resistance in transgenic potato plants under outdoor conditions).

The genus *Phytophthora* comprises various species, for example the species *alni, cactorum, capsici, cinnamomi, citrophthora, clandestina, fragariae, hedraiandra, idaei, infestans, ipomoeae, iranica, kernoviae, mirabilis, megakarya, nicotianae, palmivora, parasitica, phaseoli, ramorum, pseuodotsugae, quercina, sojae* or *tentaculata*.

In a preferred embodiment of the invention, the transgenic potato plant exhibits a resistance to *Phytophthora infestans*.

Already the inhibition of the biosynthesis of the aliphatic amino acids valine, leucine and isoleucine by a construct directed against acetolactate synthase from *P. infestans* results in a substantial reduction in blight infestation and a drastic increase in leaf resistance under laboratory and field conditions. By combining several target genes such as, for example, genes from G protein signalling, MAP kinase signalling, primary metabolism, amino acid biosynthesis and redox regulation in one construct, the resistance effect can be increased still further, since the pathogen is inhibited by the multiple action of the combination construct on the use of alternative signalling and metabolic pathways.

Surprisingly, the defensive power of the potato plants of the invention against isolates of *P. infestans* of varying aggressivity is changed in a manner such that a resistance is obtained which protects the plants efficiently and permanently against this most important of pathogens.

It was also surprisingly discovered that the resistance has no great energetic disadvantages or negative changes in the agronomic properties of the potato plant. The cultivation trials under near-field conditions did not have any deleterious effects on the quality of the plants. Careful selection of the target genes of *P. infestans* which excludes any homology extending over 17 successive base pairs with genes from non-target organisms (potato, human, pig, cattle) means that there are no restrictions on using the plants as a feed or foodstuff and no restrictions as regards sowing, cultivation, harvesting or processing the crop. The plants can freely be used as agricultural, food or feed plants.

In accordance with a preferred embodiment, the double-stranded RNA is miRNA or siRNA. MiRNA describes small interfering RNA and includes naturally produced miRNAs and synthetic miRNAs which, for example, can be produced by recombinant or chemical synthesis or by processing primary miRNA.

SiRNA describes small interfering RNA and includes naturally produced siRNAs and synthetic siRNAs which, for example, can be produced by recombinant or chemical synthesis or by processing dsRNAs.

The transgenic plant produces dsRNA from the introduced double-stranded DNA which is processed by endogenous RNAi or silencing mechanisms to form siRNAs and miRNAs.

In order to obtain dsRNA, a double-stranded first DNA with a nucleotide sequence in accordance with one of SEQ ID NOS: 1-43 or a fragment thereof in the sense orientation and a double-stranded second DNA in the antisense orientation can be used which are separated by an intron which has no similarity with the target genes in question. As an example, the DNA may be orientated with a nucleotide sequence of SEQ ID NO: 1 against the acetolactate synthase gene from *Phytophthora infestans*. Upon expression in a plant cell, an RNA transcript is formed which, because of the homology between the sense and antisense sequence regions, can coalesce to form a dsRNA. Because the missing base pairs in the region of the intron, the dsRNA forms a hairpin structure. A dsRNA with a hairpin structure can also be prepared by means of one double-stranded DNA with a nucleotide sequence in accordance with one of SEQ ID NOS: 1-43 in the sense orientation and a second in the antisense orientation with a different length. In this respect, the nucleotide sequence in the sense orientation may be about 190 nucleotides longer than the nucleotide sequence in the antisense orientation, or vice versa.

Defined sequence regions for the selected nucleotide sequences of the target genes are amplified by PCR and cloned both in the sense and in the antisense direction into a vector which is suitable for the synthesis of hairpin structures. In this regard, several fragments with sequence regions of different target genes can be cloned into a vector in order to construct a combination hairpin construct. The vectors can be introduced into a plant cell using transformation methods which are known in plant biotechnology. The skilled person will be aware that, for example, a selected nucleotide sequence of a target gene can also be cloned into one vector in the sense orientation and the nucleotide sequence of the target gene can be cloned into a second vector in the antisense orientation and then introduced into a plant cell by co-transformation, for example.

The silencing mechanism arises from dsRNA such as, for example, hairpin RNA structures or gene duplexes. The dsRNA will produce small dsRNAs by means of a dsRNA-specific endonuclease (dicer), which are processed by means of longer nucleotide sequences into small dsRNAs preferably of 21-25 base pairs, a process which is similar for both "stem-loop" (primary miRNA) and also for long complementary dsRNA precursors. Argonaut proteins, as central components of the RNA-induced silencing complexes (RISC), bind and unwind siRNA and miRNA so that the lead strand of the duplex binds specifically by base pairing to the mRNA and leads to its degradation. By means of miRNA, RNAi behaves in a comparatively similar process, with the difference that the miRNA produced also comprises partial regions which are not identical to the target genes.

After infestation of a host plant with *Phytophthora infestans*, an exchange of RNA formed in the plant which is directed against one or more *Phytophthora*-specific target sequences can occur between the host plant and the oomycetes. In the oomycetes, these RNAs can lead to sequence-specific gene silencing of one or more target genes. Proteins and protein complexes such as dicers, RISC (RNA-induced silencing complex) as well as RNA-dependent RNA polymerase (RdRP), can participate in this process.

The siRNA effect is known to be continued in plants when the RdRP synthesises new siRNAs from the degraded mRNA fragments. This secondary or transitive RNAi can reinforce silencing and also result in silencing of different transcripts when they share these highly conserved sequences.

In a preferred embodiment, the first DNA and the second DNA are operatively linked with at least one promoter.

A "promoter" is a non-translated DNA sequence, typically upstream of a coding region which contains the binding site for the RNA polymerase and initiates transcription of the DNA. A promoter contains special elements which function as regulators for gene expression (for example cis-regulatory elements). The term "operatively linked" means that the DNA which comprises the integrated nucleotide sequence is linked to a promoter in a manner such that it allows expression of this nucleotide sequence. The integrated nucleotide sequence may be linked with a terminator signal downstream as a further component.

The promoter can be of plant, animal or microbial origin, or it may be of synthetic origin and can, for example, be selected from one of the following groups of promoters: constitutive, inducible, development-specific, cell type-specific, tissue-specific or organospecific. While constitutive promoters are active under most conditions, inducible promoters exhibit expression as a result of an inducing signal which, for example, may be issued by biotic stressors such as pathogens or abiotic stressors such as cold or dryness or chemicals.

Examples of promoters are the constitutive CaMV 35S promoter (Benfey et al., 1990) as well as the C1 promoter which is active in green tissue (Stahl et al., 2004).

The first and second DNA may also, however, be operatively linked to a double promoter such as, for example, the bidirectionally active TR1' and TR2' promoter (Saito et al., 1991).

Furthermore, the first and the second DNA may each be operatively linked to a promoter.

The use of two promoters, which each flank the 3' end and the 5' end of the nucleic acid molecule, enables expression of the respective individual DNA strand, wherein two complementary RNAs are formed which hybridize and form a dsRNA. In addition, the two promoters can be deployed such that one promoter is directed towards the transcription of a selected nucleotide sequence and the second promoter is directed towards the transcription of a nucleotide sequence which is complementary to the first nucleotide sequence. As long as both nucleotide sequences are transcribed, a dsRNA is formed.

Further, a bidirectional promoter can be deployed which allows the expression of two nucleotide sequences in two directions, wherein one nucleotide sequence is read off in the 3' direction and a second nucleotide sequence is read off in the 5' direction. As long as both nucleotide sequences are complementary to each other, a dsRNA can be formed.

The present invention also concerns parts of a transgenic plant of the species *Solanum tuberosum*.

In the context of this application, the term "parts" of the transgenic plant in particular means seeds, roots, leaves, flowers as well as cells of the plant of the invention. In this regard, the term "cells" should be understood to mean, for example, isolated cells with a cell wall or aggregates thereof, or protoplasts. "Transgenic parts" of the transgenic plant also means those which can be harvested, such as potato tubers, for example.

Furthermore, the present invention concerns a method for the manufacture of a transgenic plant of the species *Solanum tuberosum* which exhibits a resistance against an oomycete of the genus *Phytophthora*.

Suitable methods for the transformation of plant cells are known in plant biotechnology. Each of these methods can be used to insert a selected nucleic acid, preferably in a vector, into a plant cell in order to obtain a transgenic plant in accordance with the present invention. Transformation methods can include direct or indirect methods for transformation and can be used for dicotyledenous plants and primarily also for monocotyledenous plants. Suitable direct transformation methods include PEG-induced DNA uptake, liposome-induced transformation, biolistic methods by means of particle bombardment, electroporation or microinjection. Examples of indirect methods are *agrobacterium*-induced transformation techniques or viral infection by means of viral vectors.

A preferred method which is employed is *agrobacterium*-induced DNA transfer using binary vectors. After transformation of the plant cells, the cells are selected on one or more markers which were transformed in the plant with the DNA of the invention and comprise genes which preferably induce antibiotic resistance such as, for example, the neomycin phosphotransferase II gene NPTII, which induces kanamycin resistance, or the hygromycin phosphotransferase II gene HPTII, which induces hygromycin resistance.

Next, the transformed cells are regenerated into complete plants. After DNA transfer and regeneration, the plants obtained may, for example, be examined by quantitative PCR for the presence of the DNA of the invention. Resistance tests on these plants against *Phytophthora infestans* in vitro and in the greenhouse are next. Routine further phenotypic investigations can be carried out by appropriately trained personnel in the greenhouse or outdoors. These transformed plants under investigation can be cultivated directly.

The method of the invention for the manufacture of a transgenic plant of the species *Solanum tuberosum* which exhibit a resistance against an oomycete of the genus *Phytophthora* comprises the following steps:

(i) producing a transformed first parent plant containing a double-stranded first DNA which is stably integrated into the genome of the parent plant and which comprises (a) a nucleotide sequence in accordance with SEQ ID NOS: 1-43, or (b) a fragment of at least 15 successive nucleotides of a nucleotide sequence in accordance with SEQ ID NOS: 1-43, or (c) a nucleotide sequence which is complementary to one of the nucleotide sequences of (a) or (b), or (d) a nucleotide sequence which hybridizes with one of the nucleotide sequences of (a), (b) or (c) under stringent conditions;

(ii) producing a transformed second parent plant containing a double-stranded second DNA which is stably integrated into the genome of the parent plant, wherein the nucleotide sequences for the coding strand of the first and second DNA are partially or completely reverse complementary with respect to each other;

(iii) crossing the first parent plant with the second parent plant;

(iv) selecting a plant in the genome of which a double-stranded first DNA and a double-stranded second DNA has been stably integrated in order to confer a pathogen resistance against an oomycete of the genus *Phytophthora* so that a double-stranded RNA can be produced therefrom.

In accordance with the invention, it is a nucleotide sequence or a fragment of a nucleotide sequence in accordance with SEQ ID NOS: 1-43 from *Phytophthora* infestans.

In a preferred embodiment of the invention, the double-stranded RNA can be miRNA or siRNA.

The invention also concerns a composition for external application to plants.

This composition is prepared for external application to plants. It contains double-stranded RNA, wherein one strand of this RNA corresponds to the transcript of a double-stranded DNA comprising (a) a nucleotide sequence in accordance with SEQ ID NOS: 1-43, or (b) a fragment of at least 15 successive nucleotides of a nucleotide sequence in accordance with SEQ ID NOS: 1-43, or (c) a nucleotide sequence which is complementary to one of the nucleotide sequences of (a) or (b), or (d) a nucleotide sequence which hybridizes with one of the nucleotide sequences of (a), (b) or (c) under stringent conditions.

Double-stranded RNA for the manufacture of the composition in accordance with the invention can be produced in vitro using methods known to the skilled person. As an example, the double-stranded RNA can be synthesized by forming the RNA directly in vitro. The double-stranded RNA can also be synthesized from a double-stranded DNA by formation of an mRNA transcript which then forms a hairpin structure, for example.

The composition in accordance with the invention can be used as a fungicide for a plant or its seed. In this regard, the composition is used to control the growth of the pathogen, for containing the propagation of the pathogen or for the treatment of infected plants. As an example, the composition can be used as a fungicide for spraying in the form of a spray, or other routine ways which are familiar to the skilled person for external application to the plant tissue or by spraying or mixing with the cultivation substrate before or after the plants have sprouted.

In a further application, the composition in accordance with the invention is used as a pre-treatment for seed. In this regard, the composition is initially mixed with a carrier substrate and applied to the seeds in a combination which comprises the double-stranded RNA and the carrier substrate, whereby the carrier substrate has an RNA-stabilizing effect, for example. Thus, the RNA stability and thus its action on the selected target genes of *Phytophthora infestans* can be increased, for example by chemical modifications such as the exchange of ribose for a hexose. Liposomes which encapsulate the RNA molecules can also be used as RNA stabilizers.

Ideally, the plants treated with the composisiton are those of the species *Solanum tuberosum.*

The discussion above regarding the plant of the invention and the method of the invention also apply to this composition.

The present invention will now be described with reference to the figures and sequences:

BRIEF DESCRIPTION OF THE DRAWINGS

FIG. 1: Plasmid pRNAi as an exemplary representation of a vector which can be used for the formation of hairpin constructs against a target gene. This vector contains a CaMV 35S promoter, a multiple cloning site, an intron from the gene AtAAP6 which codes for an amino acid permease in *Arabidopsis thaliana*, a further multiple cloning site as well as a CaMV 35S terminator.

FIG. 2: Plasmid pRNAi_PITG_03410 as an exemplary representation of a vector which contains a sense-intron-antisense fragment for the formation of dsRNA against a target gene (here PITG_03410). This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.

Figure 3:
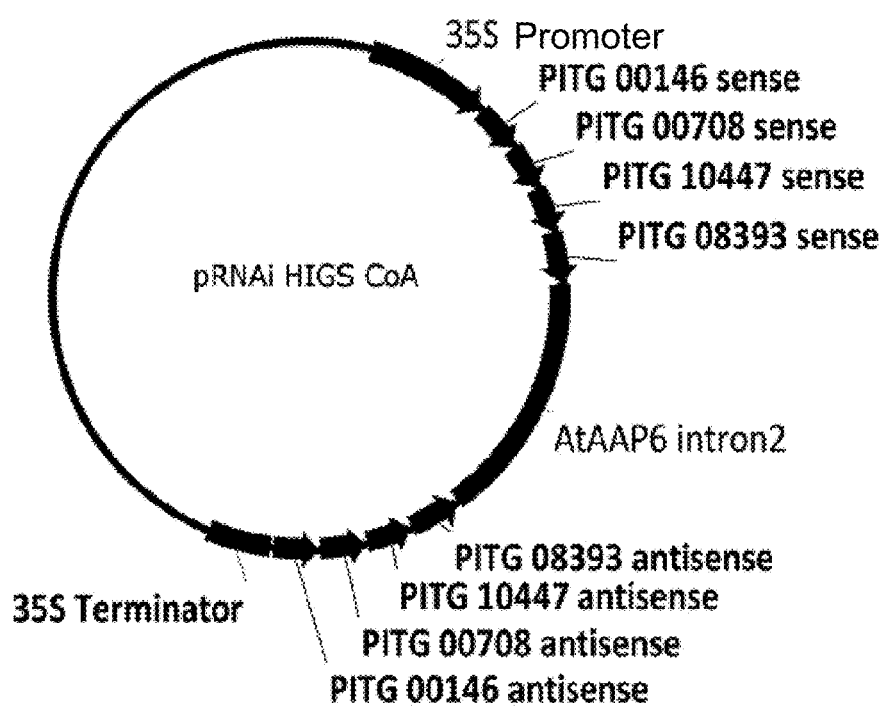

FIG. 3: Plasmid pRNAi_HIGS_CoA as an exemplary representation of a vector which contains various defined sequences in the sense-intron-antisense fragment, which should lead to the formation of dsRNA against various target genes. This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.

Figure 4:
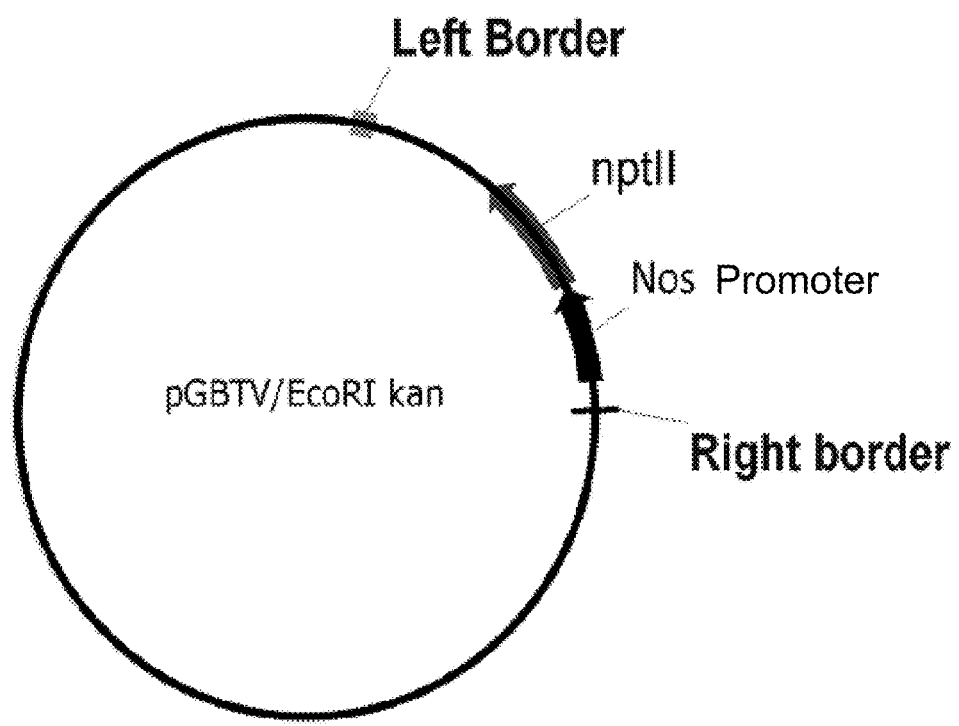

FIG. 4: Plasmid pGBTV/EcoRI_kan. Binary Ti plasmid which was used as a cloning vector.

Figure 5:
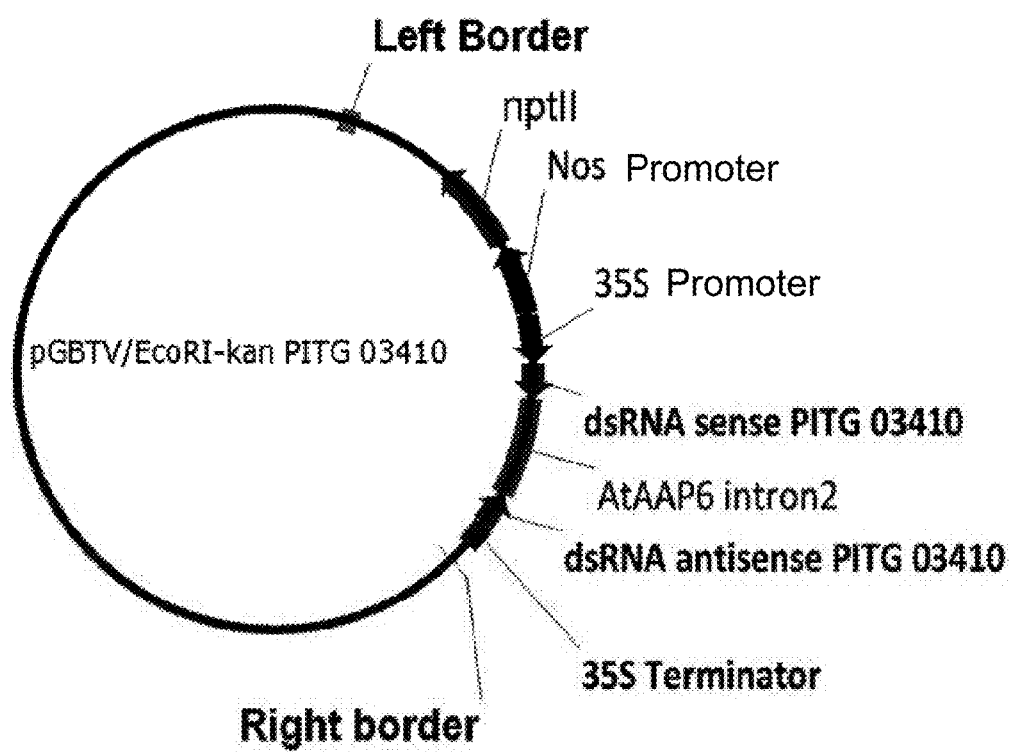

FIG. 5: Plasmid pGBTV/EcoRI_kan_PITG_03410. Binary Ti plasmid which was used for *agrobacterium*-induced transformation.

Figure 6:
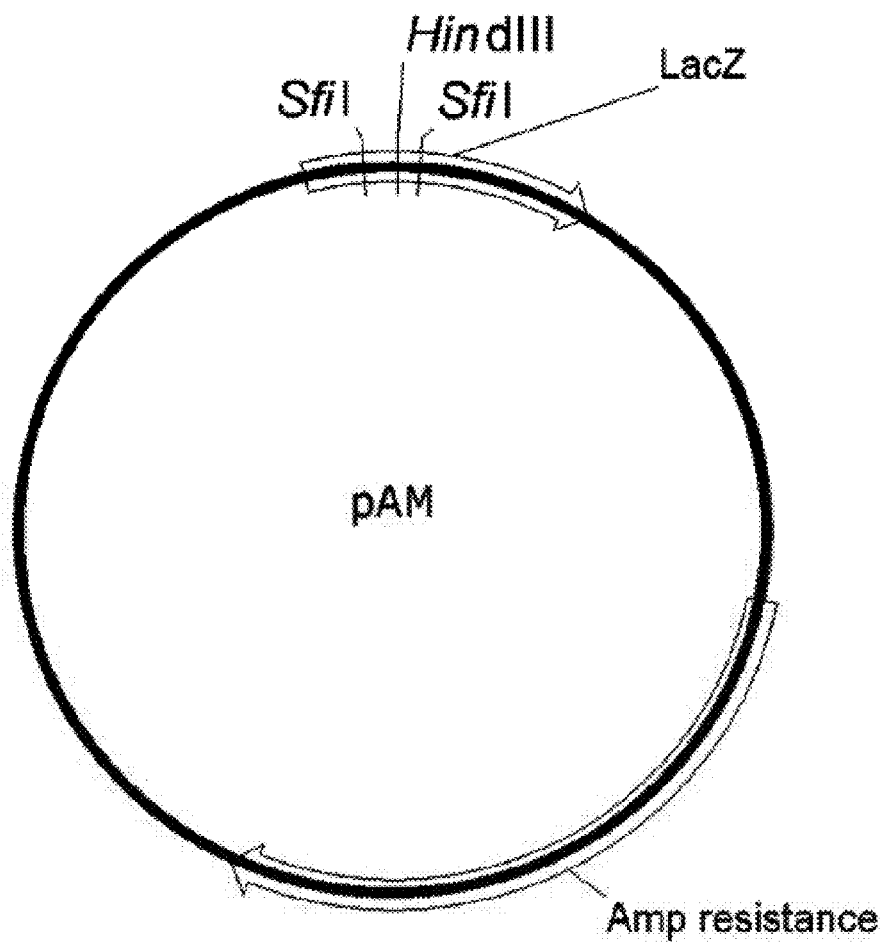

FIG. 6: Plasmid pAM, which was used as a cloning vector.

Figure 7:
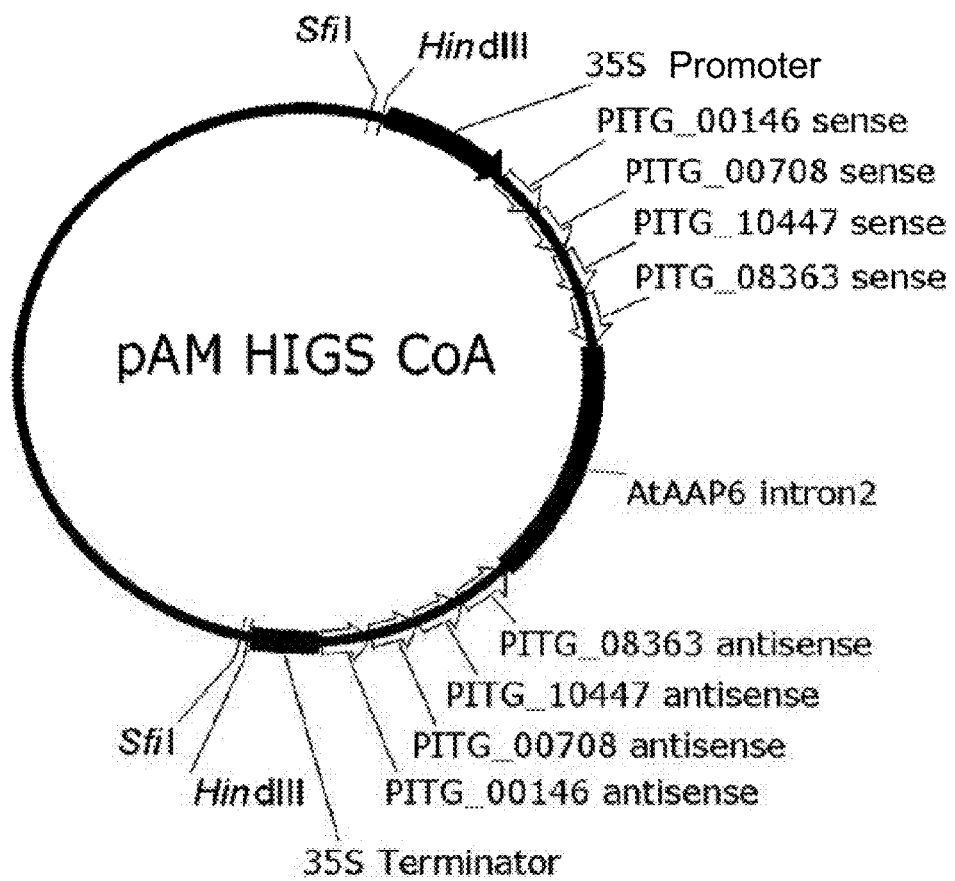

FIG. 7: Plasmid pAM_HIGS_CoA, as an example of a plasmid which was used as a cloning vector.

Figure 8:
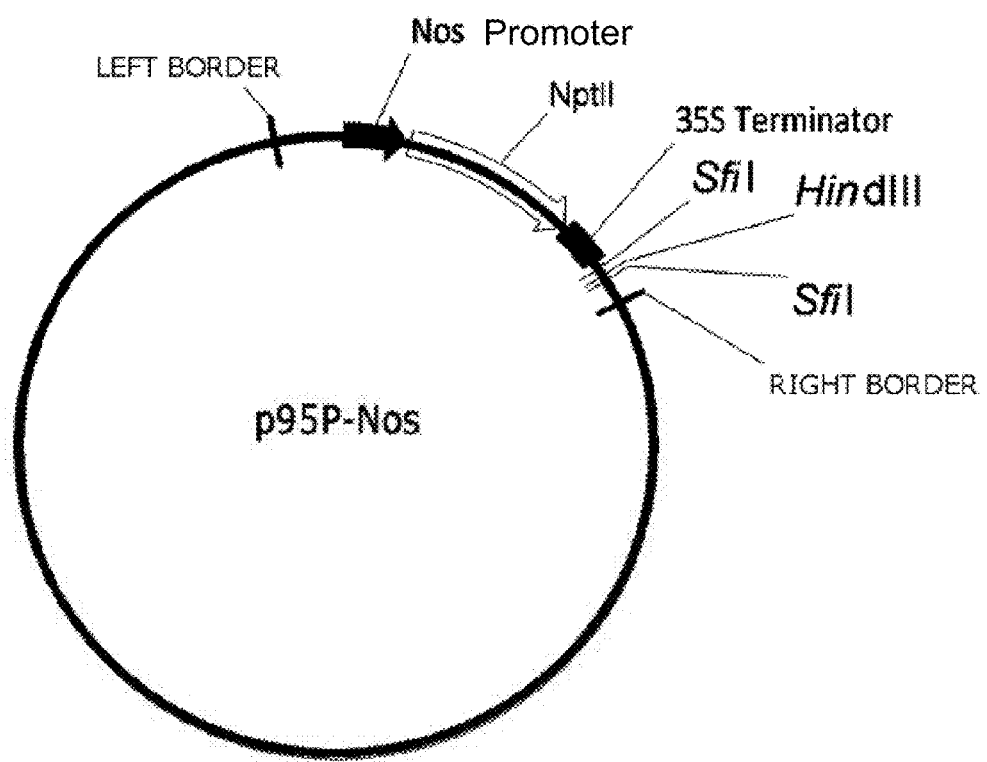

FIG. 8: Plasmid p95P-Nos. Binary Ti plasmid which was used as a cloning vector.

Figure 9:
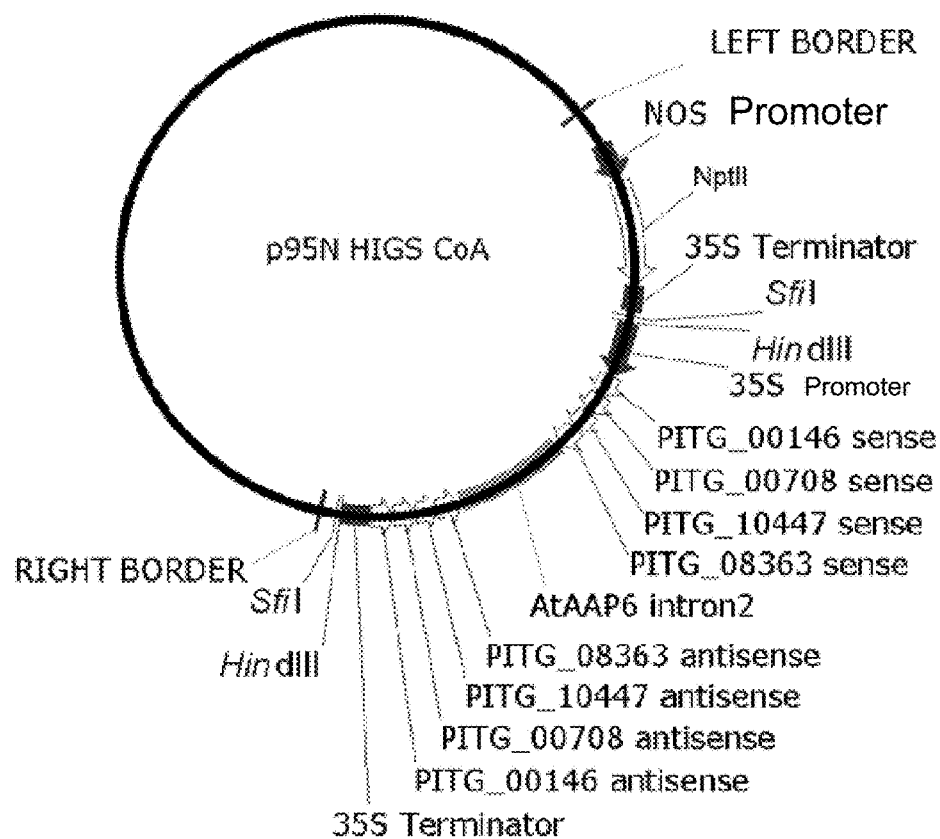

FIG. 9: Plasmid p95N_HIGS_CoA. Binary Ti plasmid which was used for *agrobacterium*-induced transformation.

Figure 10:
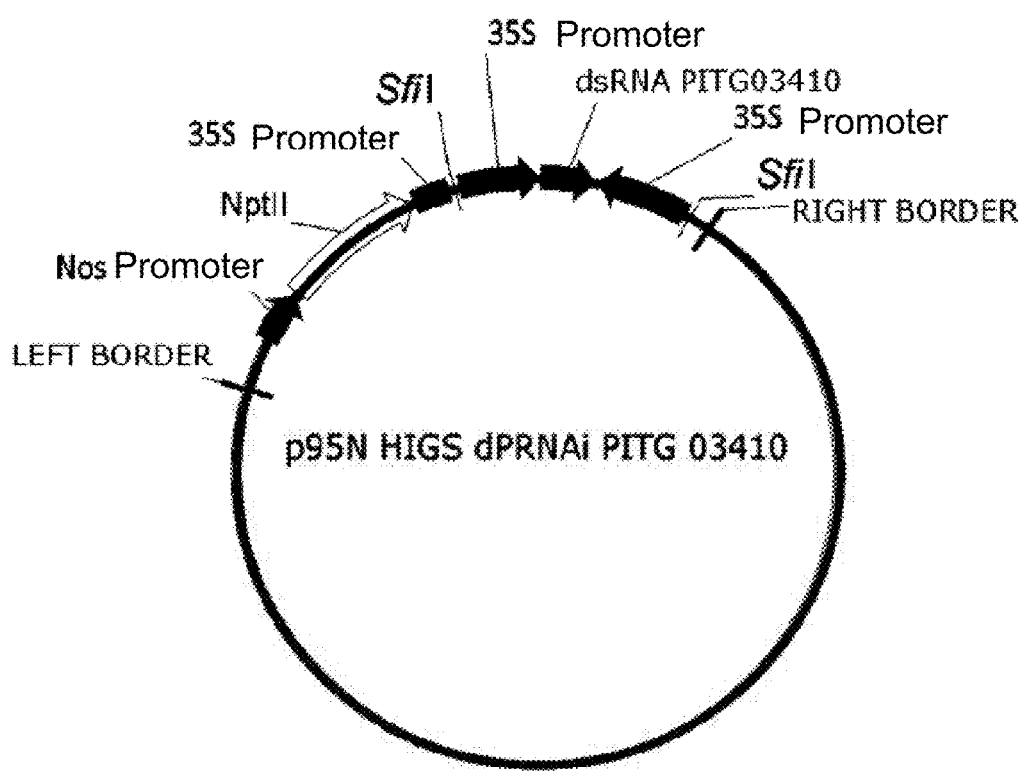

FIG. 10: Plasmid p95N_HIGS_dPRNAi_PITG_03410 as an exemplary representation of a binary vector for the formation of dsRNA against a target gene (here PITG_03410) using two CaMV 35S promoters which each flank the 3'- and the 5' end of the nucleic acid molecule.

Figure 11:
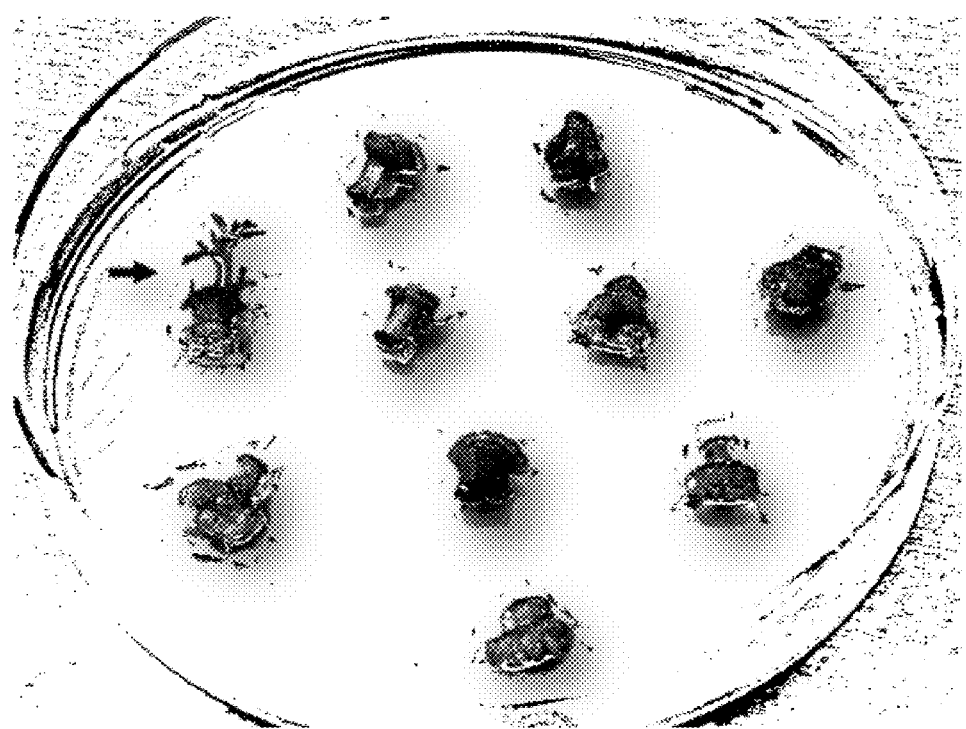

FIG. 11: Transgenic potato shoot on selection medium after transformation in the regeneration stage.

Figure 12:

FIG. 12: Diagnostic PCR for testing the transgenicity of potatoes (PR-H4) after transformation with the binary vector pGBTV/EcoRI_kan_PITG_03410.

Detection of sense fragment (370 bp) (primer S334 5'-ATCCCACTATCCTTCGCAAG-3' (SEQ ID NO: 44)× S1259 5'-TTGATATCGCGGAAGGCGAGAGACATCG-3' (SEQ ID NO: 45)) and antisense fragment (450 bp) (S 329 5'-CTAAGGGTTTCTTATATGCTCAAC-3' (SEQ ID NO: 46)×S1259 5'-TTGATATCGCGGAAGGCGAGAGA-CATCG-3' (SEQ ID NO: 45)). Mix: PCR-MasterMix, PCR monitoring. Marker: Tracklt™ 1 Kb DNA Ladder.

Figure 13:
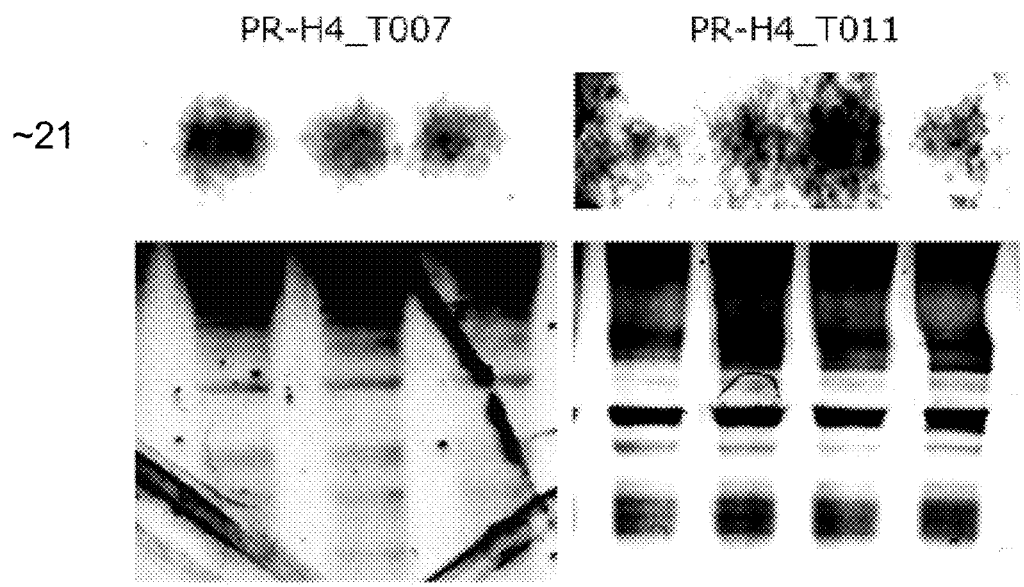
Figure 13:
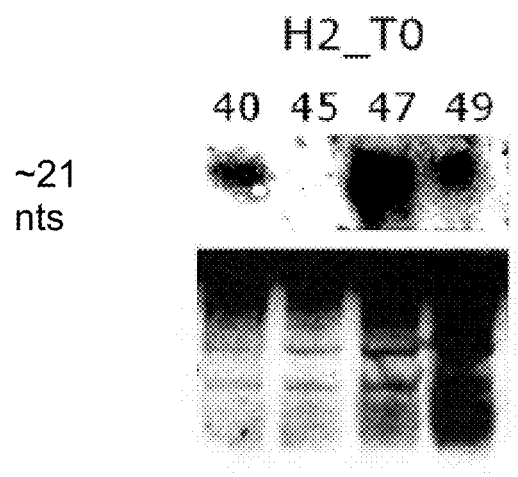

FIG. 13 A: Detection of siRNAs in transgenic potato plants after transformation with the binary vector pGBTV/ EcoRI_kan_PITG_03410. Detection was carried out by hybridization of the Northern Blot with the radioactively labelled probe dsRNA_. Multiple applications of various samples from the lines PR-H4_T007 and TO11. FIG. 13 B: Detection of siRNAs in transgenic potato plants after transformation with the binary vector p95N HIGS_PITG_00375. Detection was carried out by hybridization of the Northern Blot with the radioactively labelled probe dsR-NA_PITG00375. Single application of the samples from the lines PR-H2_T040, T045, T047 and T049.

Figure 14:
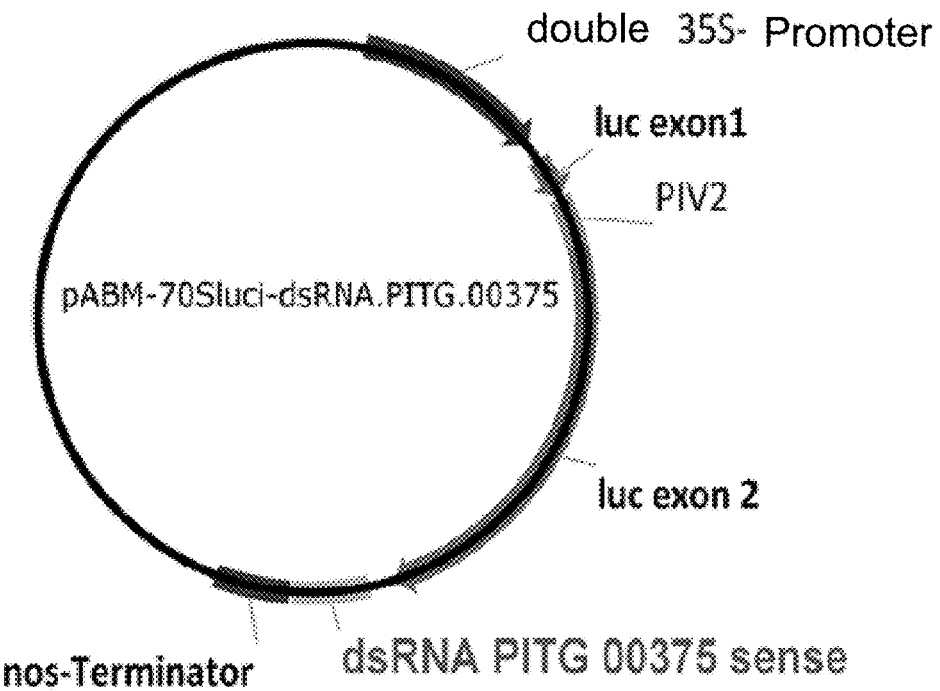
Figure 14:
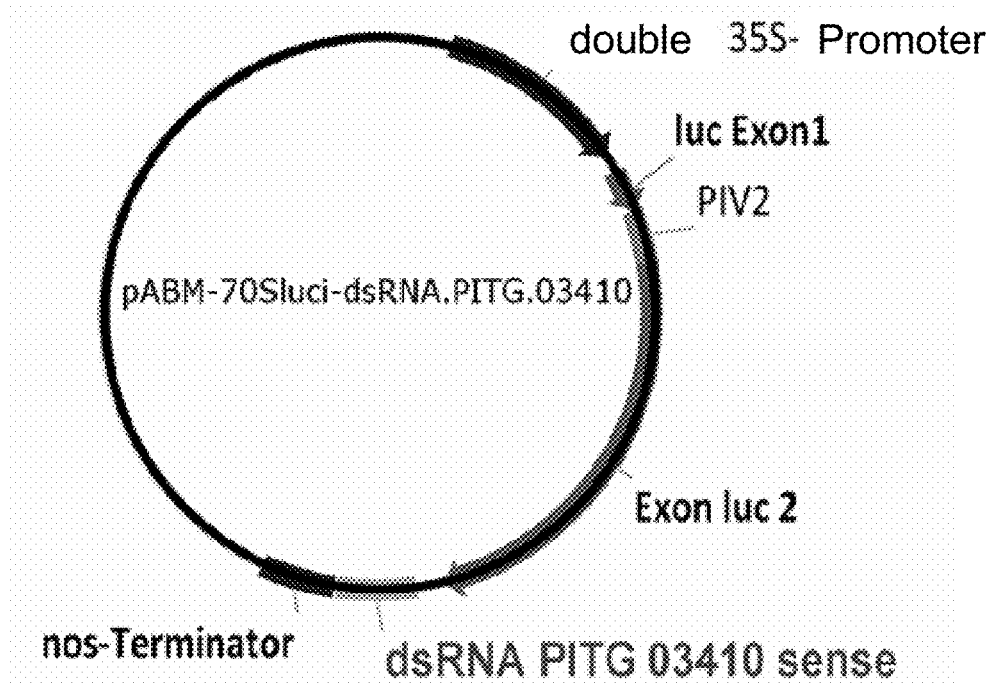

FIG. 14 A: Plasmid pABM-70Sluci_dsRNA.PITG_00375 as an exemplary representation of a vector which contains a fusion construct consisting of the luciferase reporter gene and the test HIGS target fragment PITG_00375. The vector additionally contains a double CaMV 35S promoter, a multiple cloning site, the coding sequence for the luc gene from *Photinus pyralis*, which codes for a luciferase, separated from a modified intron PIV2 from the potato gene St-LS1 (Eckes et al. 1986, Vancanneyt et al. 1990), a further multiple cloning site as well as a Nos terminator from the nopalin synthase gene from *Agrobacterium tumefaciens*.

FIG. 14 B: Plasmid pABM-70Sluci_dsRNA.PITG_03410 as an exemplary representation of a vector which contains a fusion construct consisting of a luciferase reporter gene and the test HIGS target gene fragment PITG_03410.

Figure 15:
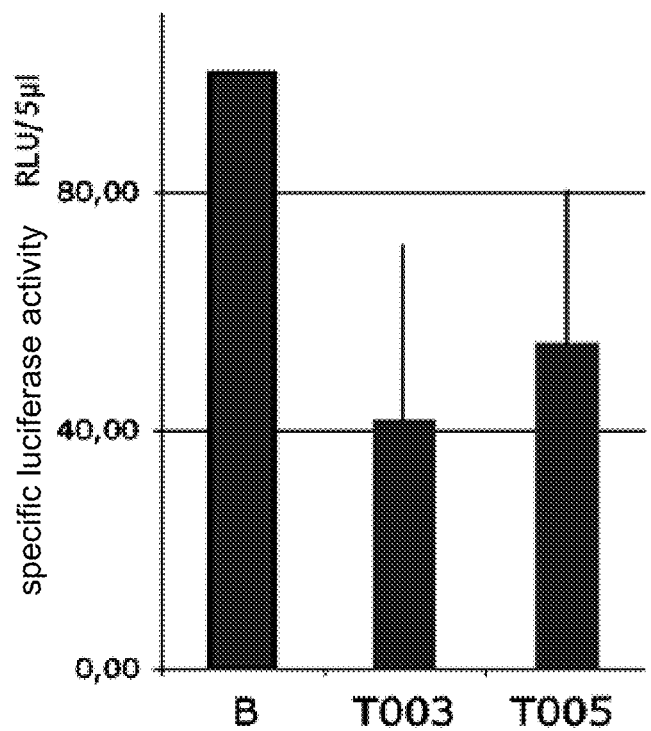
Figure 15:
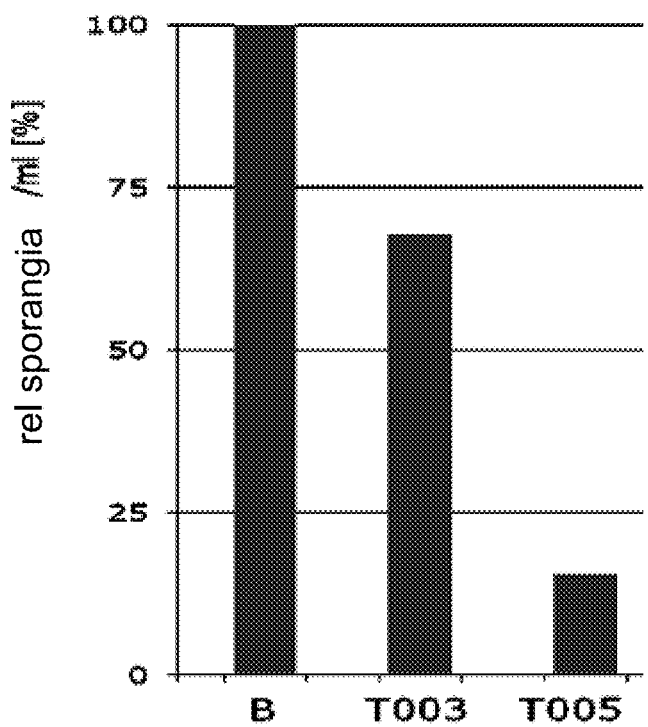

FIG. 15 A: Relative luciferase activity in transgenic potato lines of the genotype Baltica with stable integration of the HIGS_RNAi construct against the PITG_03410 gene from *P. infestans* after bombardment with the vector pABM-70Sluci_dsRNA.PITG_03410. B: Baltica (non-transgenic control), T003, T005 transgenic HIGS potato lines.

FIG. 15 B: Relative sporangia production from *P. infestans* on transgenic HIGS lines. The potato lines of the variety Baltica were transformed with an RNAi construct in order to form dsRNA against the *P. infestans* gene PITG_03410. After infection with *P. infestans* in the detached leaf assay, these lines exhibited a reduced sporangia production compared with the non-transgenic variety Baltica (mean of 4 biological repetitions). B: Baltica (non-transgenic control), T003, T005: transgenic HIGS potato lines.

Figure 16:
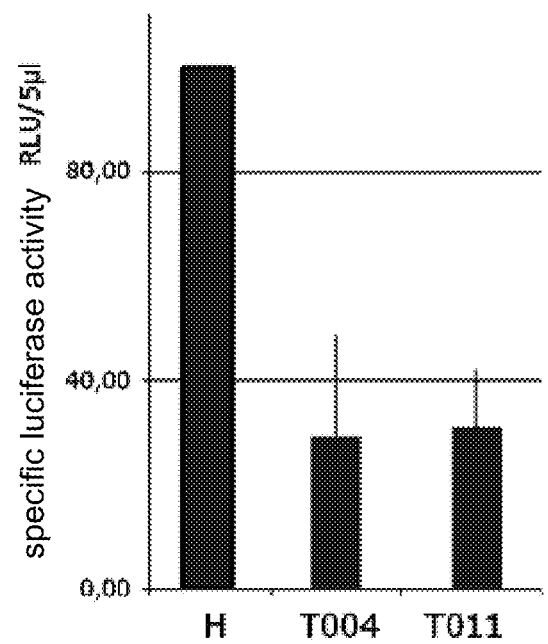
Figure 16:
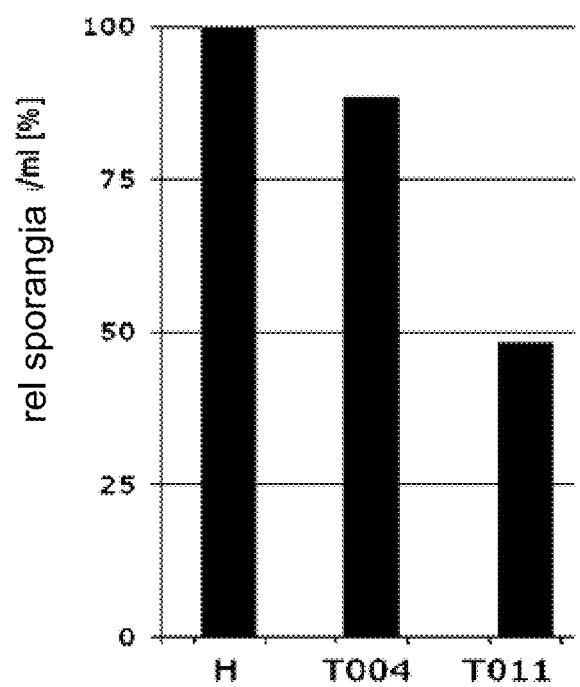

FIG. 16 A: Relative Luciferase activity in transgenic potato lines of the genotype Hermes with stable integration of the HIGS_RNAi construct against the PITG_03410 gene from *P. infestans* after bombardment with the vector pABM-70Sluci_dsRNA.PITG_03410. H: Hermes (non-transgenic control), T004, TO11: transgenic HIGS potato lines.

FIG. 16 B: Relative sporangia production of *P. infestans* on transgenic HIGS lines. The potato lines of the variety Hermes were transformed with an RNAi construct in order to form dsRNA against the *P. infestans* gene PITG_03410. After infection with *P. infestans* in the detached leaf assay, these lines exhibited a reduced sporangia production compared with the non-transgenic variety Baltica (mean of 4 biological repetitions). H: Hermes (non-transgenic control), T004, TO11: transgenic HIGS potato lines.

Figure 17:
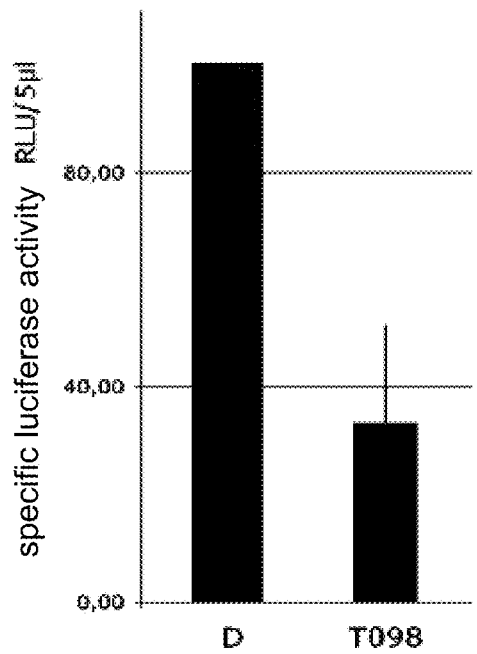
Figure 17:
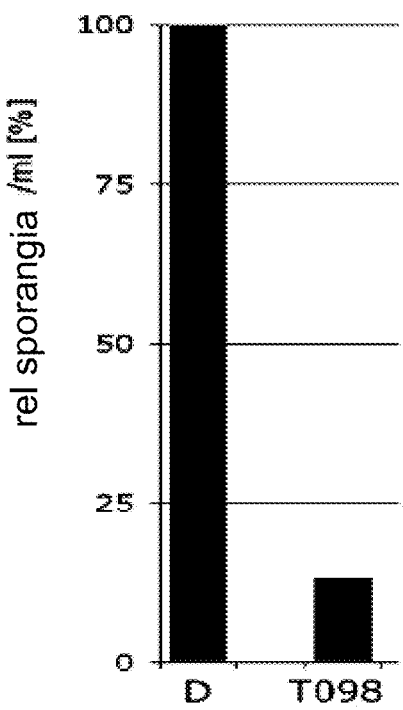

FIG. 17 A: Relative luciferase activity in transgenic potato lines of the genotype Desirée with stable integration of the HIGS_RNAi construct against the PITG_03410 gene from *P. infestans* after bombardment with the vector pABM-70Sluci_dsRNA.PITG_03410. D: Desirée (non-transgenic control), T098: transgenic HIGS potato line.

FIG. 17 B: Relative sporangia production of *P. infestans* on transgenic HIGS lines. The potato lines of the variety Desirée were transformed with an RNAi construct in order to form dsRNA against the *P. infestans* gene PITG_03410. After infection with *P. infestans* in the detached leaf assay, these lines exhibited a reduced sporangia production compared with the non-transgenic variety Baltica (mean of 4 biological repetitions). D: Desirée, (non-transgenic control), T098: transgenic HIGS potato line.

Figure 18:
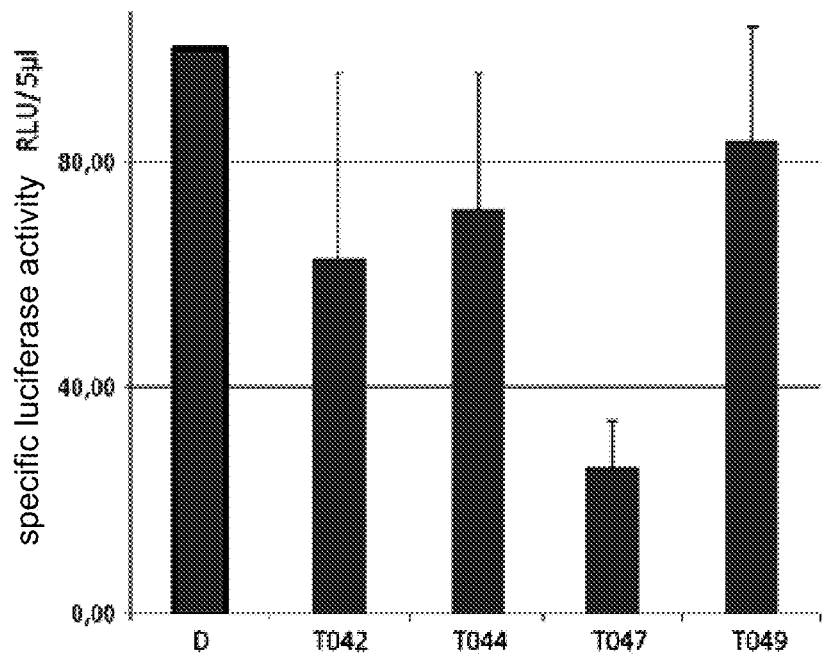
Figure 18:
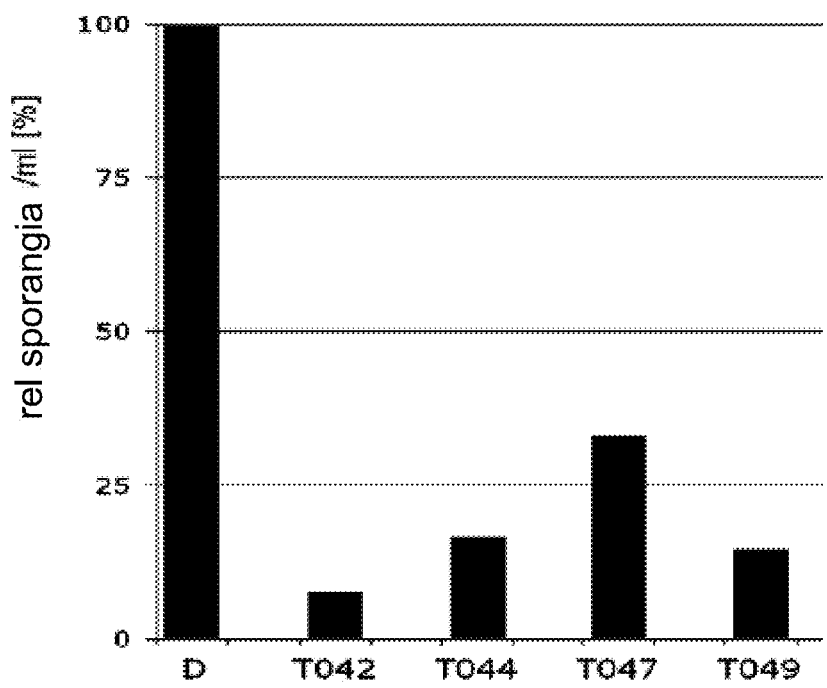

FIG. 18 A: Relative Luciferase activity in transgenic potato lines of the genotype Desirée with stable integration of the HIGS_RNAi construct against the PITG_00375 gene from *P. infestans* after bombardment with the vector pABM-70Sluci_dsRNA.PITG_00375. D: Desirée, (non-transgenic control), T042, T044 T047, T049: transgenic HIGS potato lines.

FIG. 18 B: Relative sporangia production of *P. infestans* on transgenic HIGS lines. The potato lines of the variety Desirée were transformed with a RNAi construct in order to form dsRNA against the *P. infestans* gene PITG_00375. After infection with *P. infestans* in the detached leaf assay, these lines exhibited a reduced sporangia production compared with the non-transgenic variety Baltica (mean of 4 biological repetitions). D: Desirée, (non-transgenic control), T042, T044 T047, T049: transgenic HIGS potato lines.

Figure 19A:
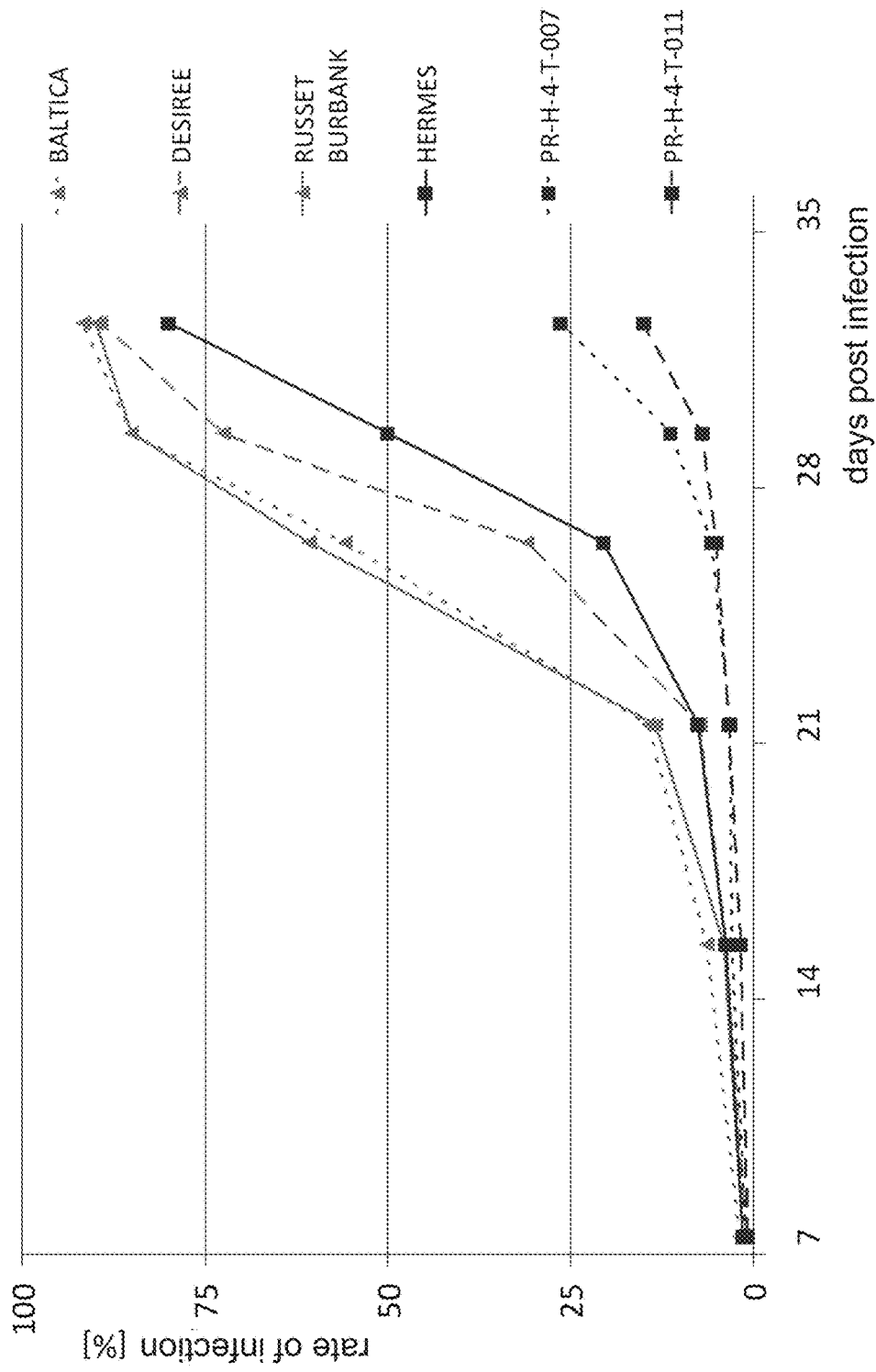
Figure 19:
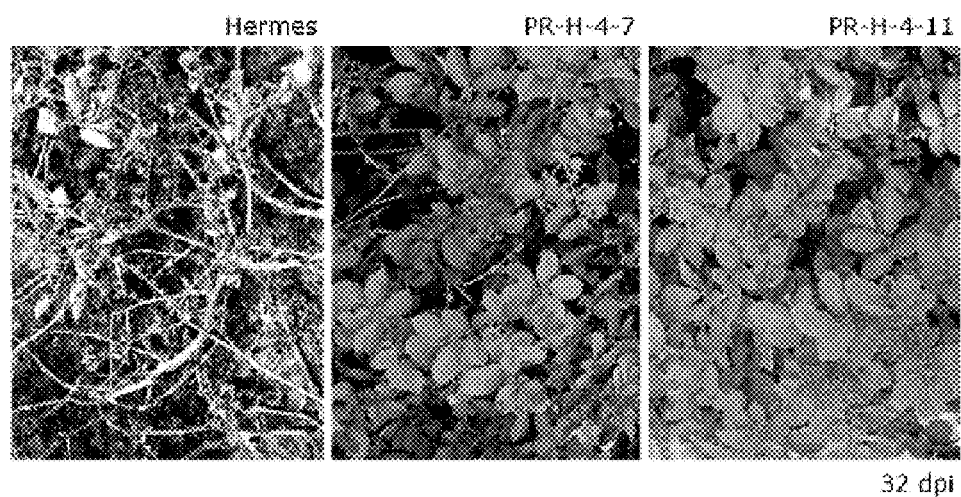
Figure 20:
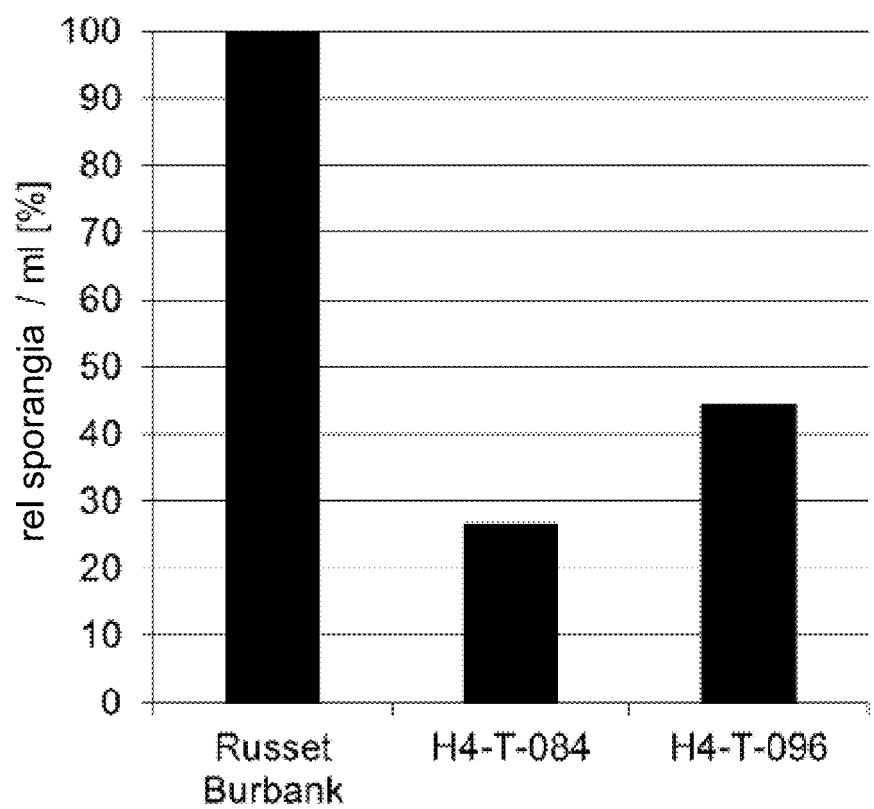
Figure 21:
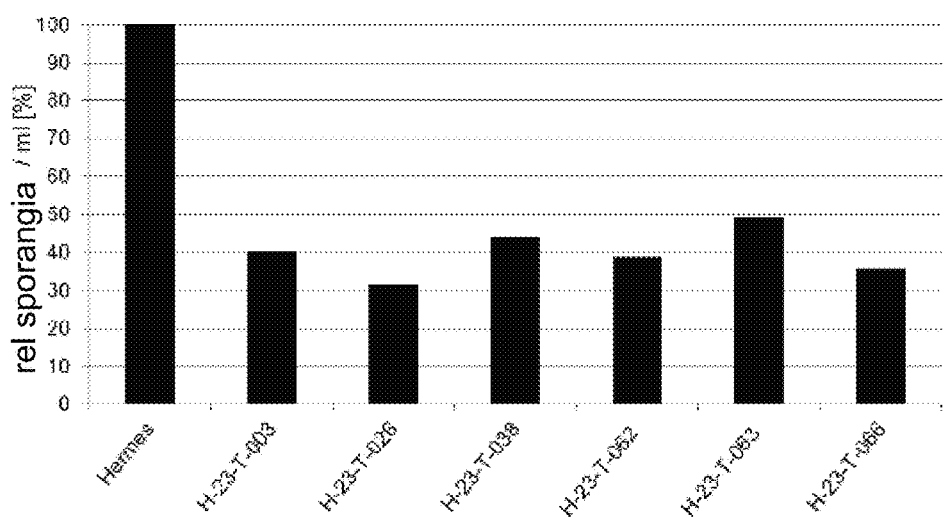
Figure 22:
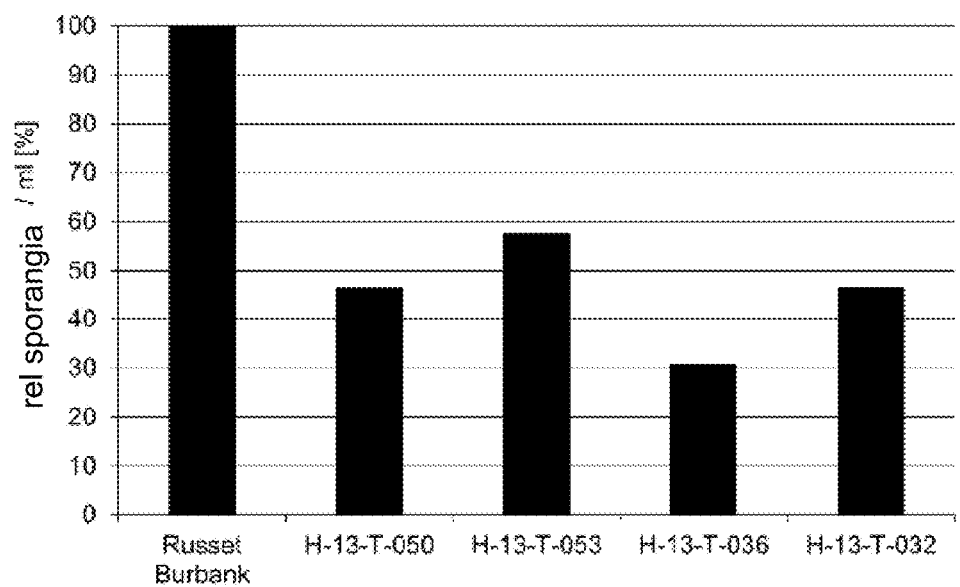
Figure 23:
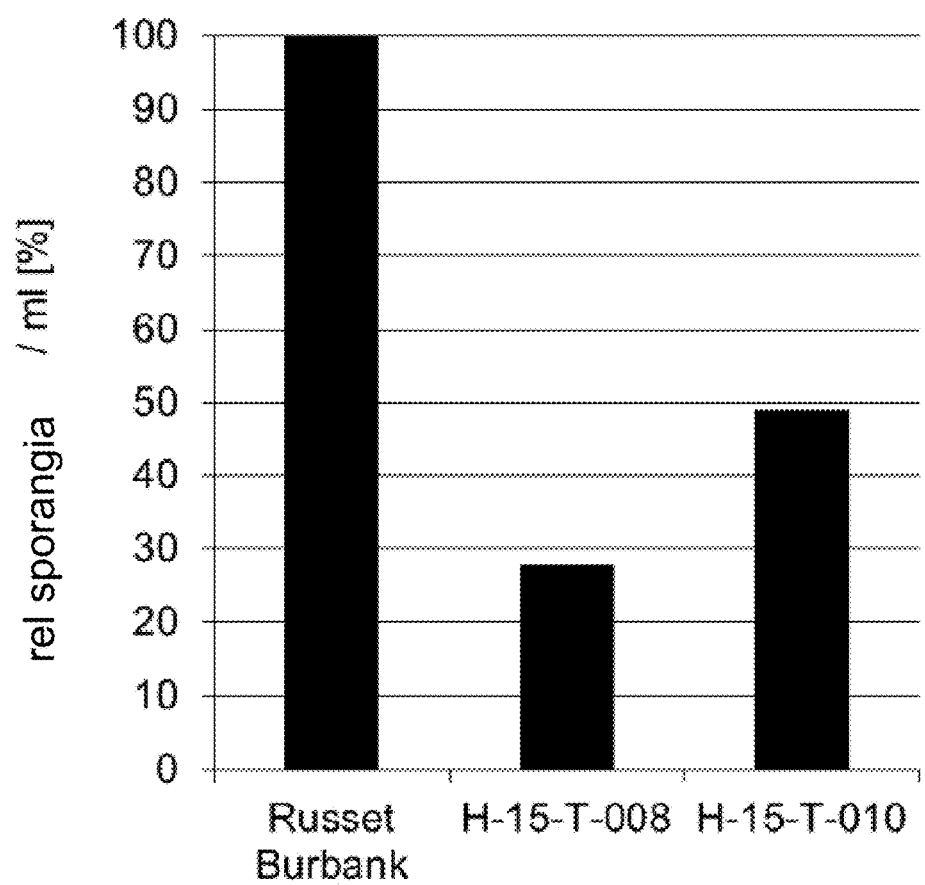
Figure 24:
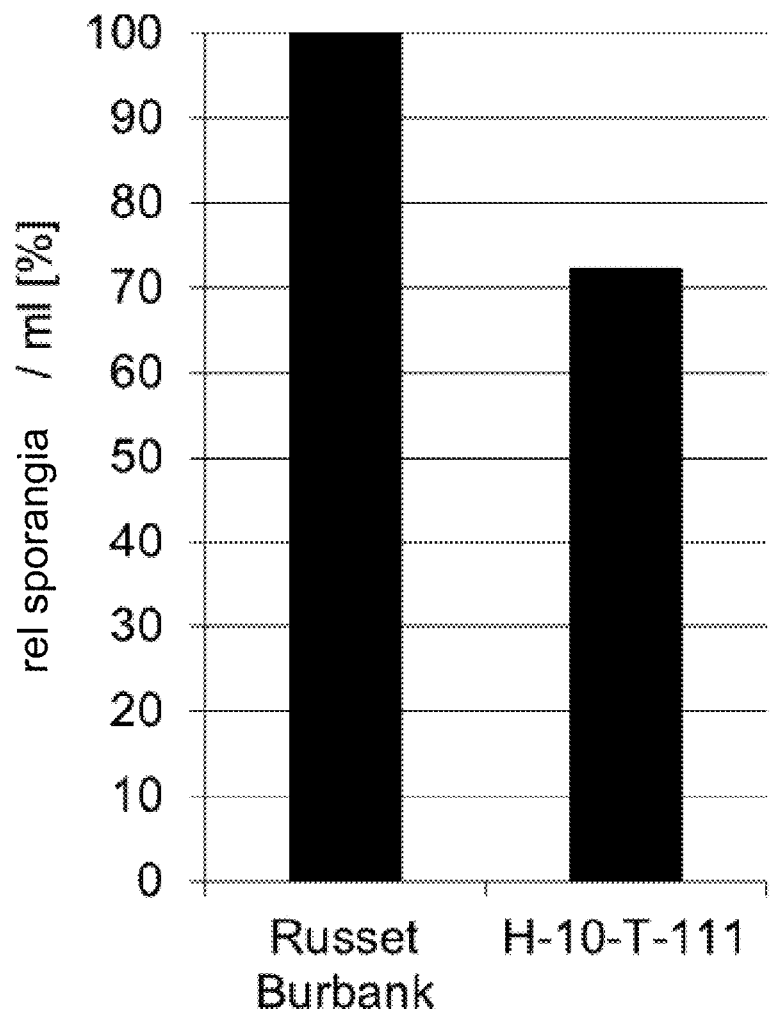
Figure 25:
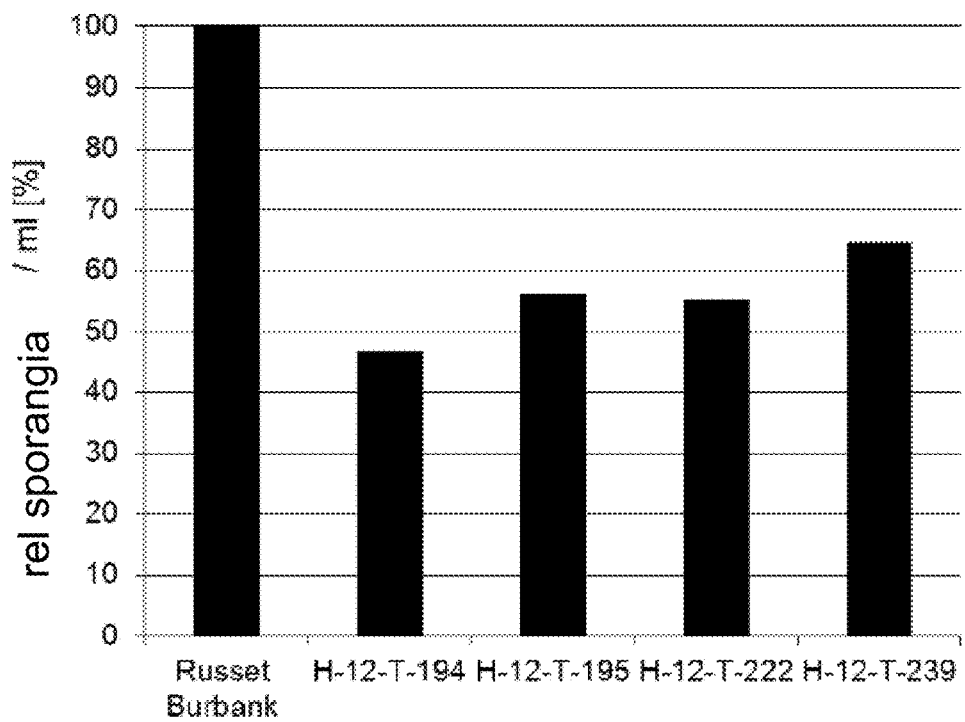
Figure 26:
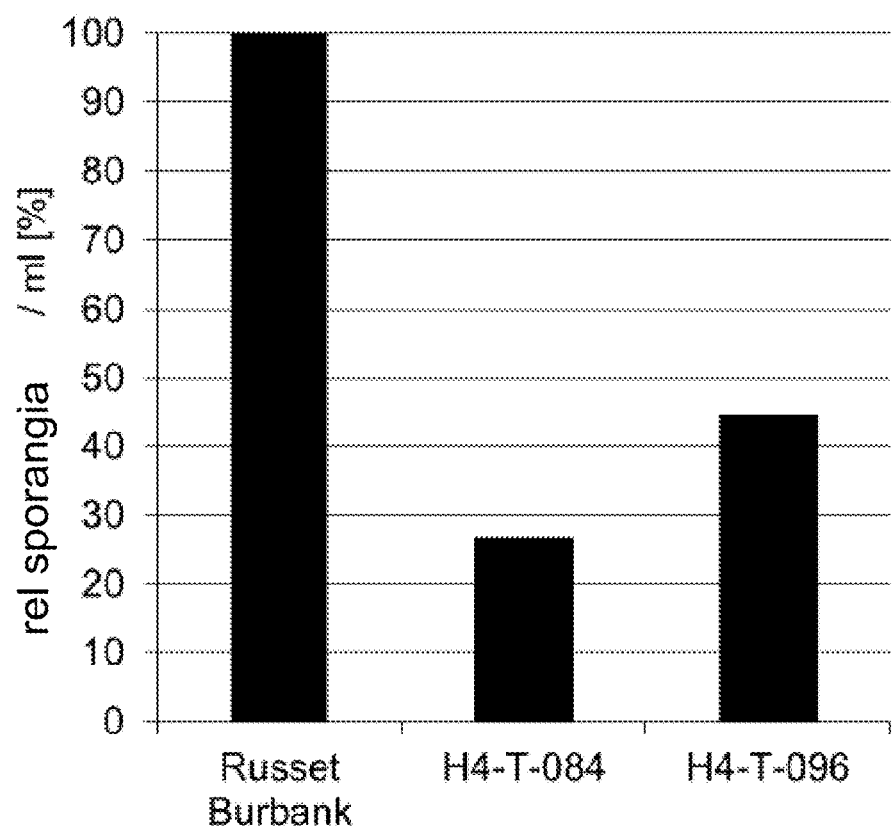
Figure 27:
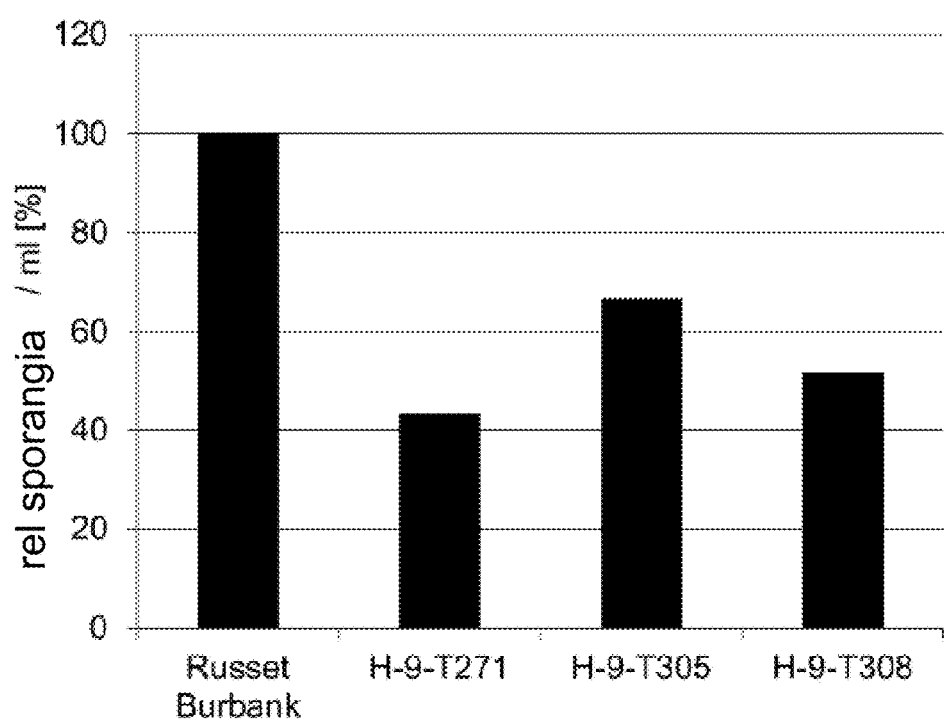
Figure 28:
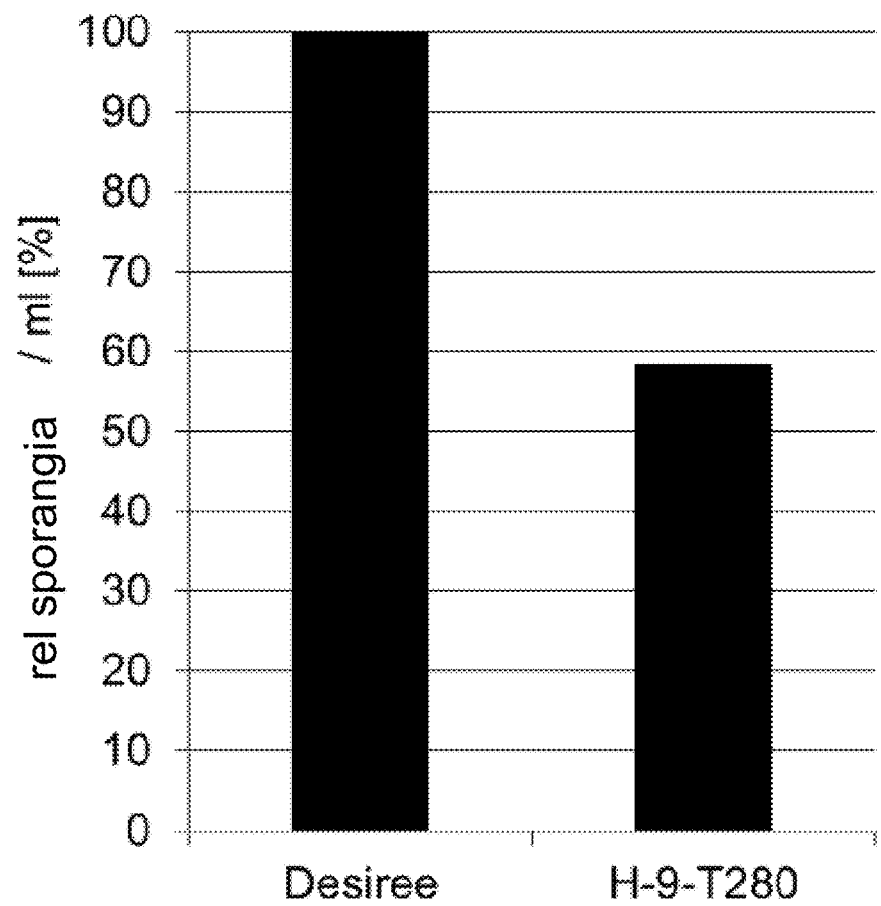
Figure 29:
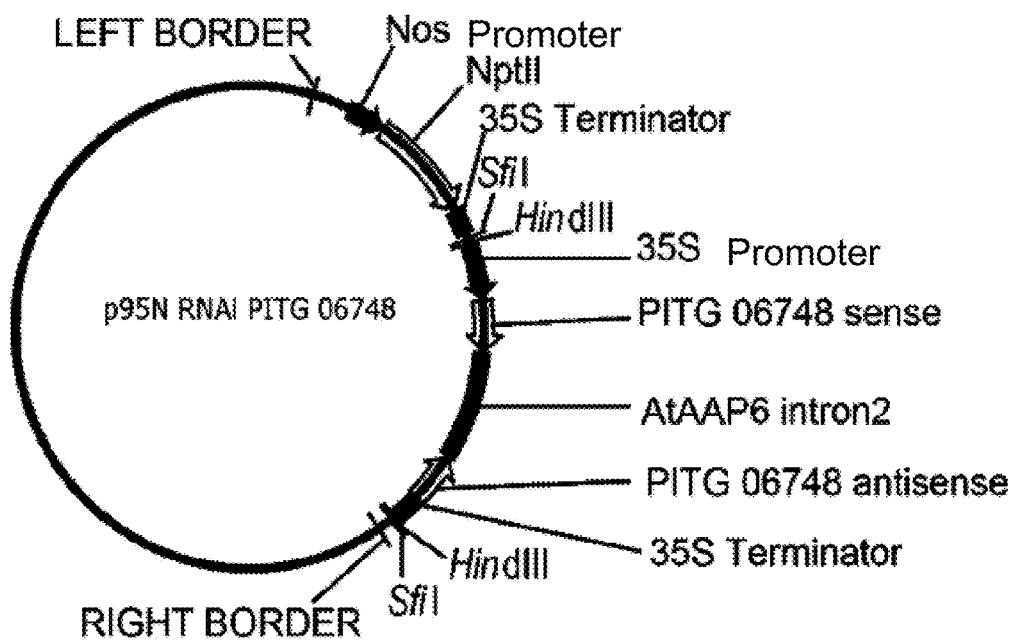
Figure 30:
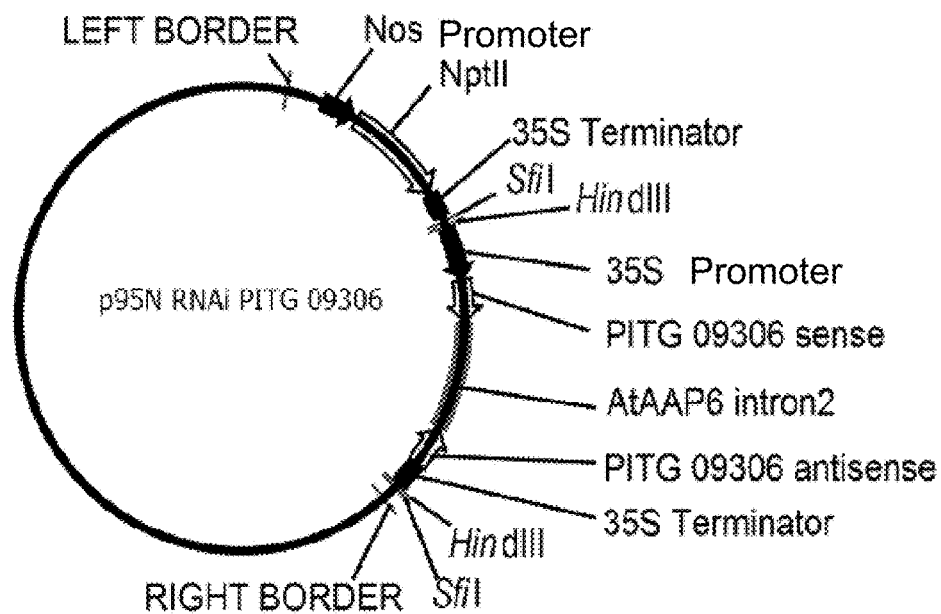
Figure 31:
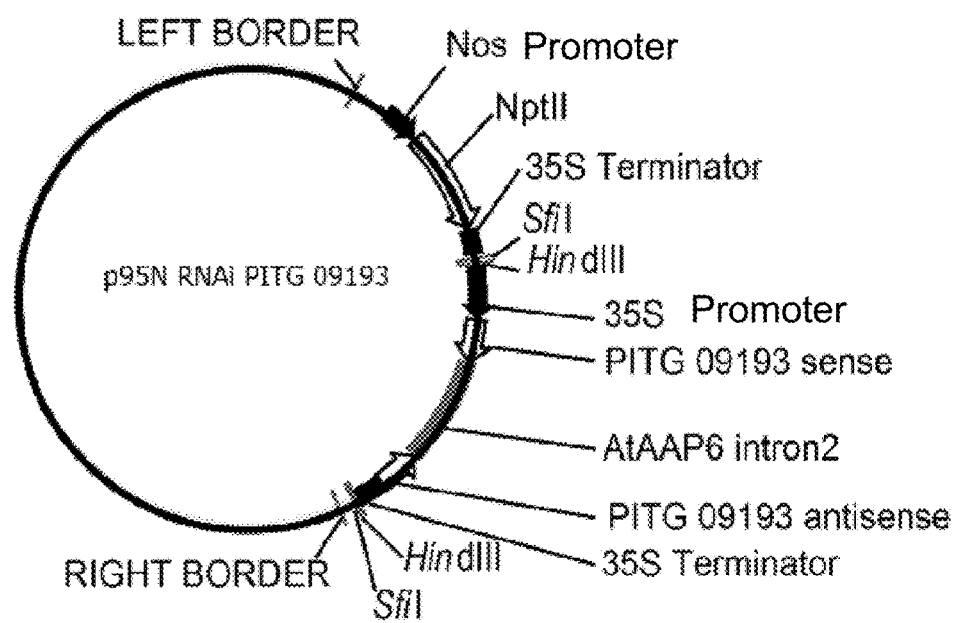
Figure 32:
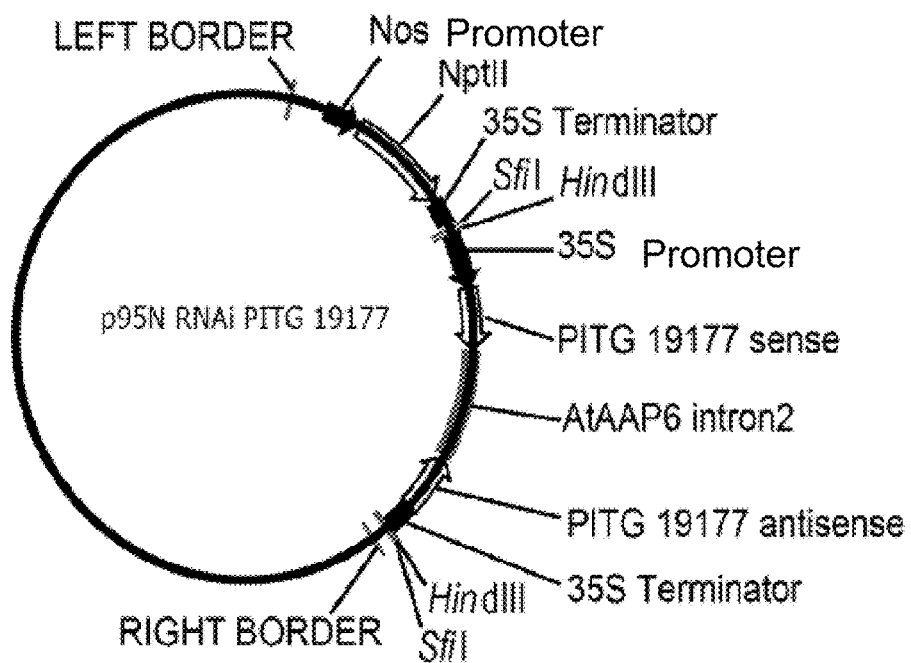

FIG. 19 A: Level of infection in transgenic potato lines of the genotype Hermes with stable integration of the HIG- S_RNAi construct against the PITG_03410 gene from *P. infestans* after infection of the plants under outdoor-like conditions with *P. infestans*. Grey lines with triangle: *Baltica*, Desirée, and Russet Burbank (non-transgenic controls), Black lines with square: plants of the genotype Hermes: solid line: Hermes (non-transgenic control), dashed line: PR-H-4-7 & dotted line: PR-H-4-11: transgenic HIGS potato lines.

FIG. 19 B: Photographic documentation of the degree of infection of the transgenic potato lines PR-H-4-7 and PR-H-4-11 of the genotype Hermes with stable integration of the HIGS_RNAi construct against the PITG_03410 gene from *P. infestans* after infection of the plants under outdoor-like conditions with *P. infestans* compared with the non-transgenic control Hermes. Photographs taken 32 days post-infection.

FIG. 20: Relative sporangia production of *P. infestans* on transgenic HIGS lines. The potato lines of the variety Russet Burbank were transformed with a RNAi construct in order to form dsRNA against the *P. infestans* gene PITG_03410. After infection with *P. infestans* in the detached leaf assay, these lines exhibited a reduced sporangia production compared with the non-transgenic variety Russet Burbank (mean of 3 biological repetitions). Russet Burbank (non-transgenic control); H-4-T084, H-4-T096: transgenic HIGS potato lines.

FIG. 21: Relative sporangia production of *P. infestans* on transgenic HIGS lines. The potato lines of the variety Hermes were transformed with a RNAi construct in order to form dsRNA by means of a double promoter construct HIGS_dPRNAi_PITG_03410 against the *P. infestans* gene PITG_03410. After infection with *P. infestans* in the detached leaf assay, these lines exhibited a reduced sporangia production compared with the non-transgenic variety Hermes (mean of 3 biological repetitions). Hermes (non-transgenic control); H-23-T0003, H-23-T026, H-23-T038, H-23-T062, H-23-T063, H-23-T066: transgenic HIGS potato lines.

FIG. 22: Relative sporangia production of *P. infestans* on transgenic HIGS lines. The potato lines of the variety Russet Burbank were transformed with an RNAi construct HIGS_CoA in order to form dsRNA against the genes PITG_00146, PITG_08393, PITG_10447 and PITG_00708 from *P. infestans*. After infection with *P. infestans* in the detached leaf assay, these lines exhibited a reduced sporangia production compared with the non-transgenic variety Russet Burbank (mean of 3 biological repetitions). Russet Burbank (non-transgenic control); H-13-T050, H-13-T053, H-13-T036, H-13-T032: transgenic HIGS potato lines.

FIG. 23: Relative sporangia production of *P. infestans* on transgenic HIGS lines. The potato lines of the variety Russet Burbank were transformed with a RNAi construct in order to form dsRNA against the *P. infestans* gene PITG_06748. After infection with *P. infestans* in the detached leaf assay, these lines exhibited a reduced sporangia production compared with the non-transgenic variety Russet Burbank (mean of 3 biological repetitions). Russet Burbank (non-transgenic control); H-15-T008, H-15-T010: transgenic HIGS potato lines.

FIG. 24: Relative sporangia production of *P. infestans* on transgenic HIGS line. The potato line of the variety Russet Burbank were transformed with an RNAi construct in order to form dsRNA against the *P. infestans* gene PITG_09306. After infection with *P. infestans* in the detached leaf assay, these lines exhibited a reduced sporangia production compared with the non-transgenic variety Russet Burbank (mean of 3 biological repetitions). Russet Burbank (non-transgenic control); H-10-T111: transgenic HIGS potato line.

FIG. 25: Relative sporangia production of *P. infestans* on transgenic HIGS lines. The potato lines of the variety Russet Burbank were transformed with an RNAi construct in order to form dsRNA against the *P. infestans* gene PITG_09193. After infection with *P. infestans*, in the detached leaf assay, these lines exhibited a reduced sporangia production compared with the non-transgenic variety Russet Burbank (mean of 3 biological repetitions). Russet Burbank (non-transgenic control); H-12-T194, H-12-T195, H-12-T222, H-12-T239: transgenic HIGS potato lines.

FIG. 26: Relative sporangia production of *P. infestans* on transgenic HIGS lines. The potato lines of the variety Desirée were transformed with an RNAi construct in order to form dsRNA against the *P. infestans* gene PITG_09193. After infection with *P. infestans*, in the detached leaf assay, these lines exhibited a reduced sporangia production compared with the non-transgenic variety Desirée (mean of 3 biological repetitions). Desirée (non-transgenic control); H-12-T187, H-12-T216, H-12-T237, H-12-T245: transgenic HIGS potato lines.

FIG. 27: Relative sporangia production of *P. infestans* on transgenic HIGS lines. The potato lines of the variety Russet Burbank were transformed with an RNAi construct in order to form dsRNA against the *P. infestans* gene PITG_19177. After infection with *P. infestans*, in the detached leaf assay, these lines exhibited a reduced sporangia production compared with the non-transgenic variety Russet Burbank (mean of 3 biological repetitions). Russet Burbank (non-transgenic control); H-9-T271, H-9-T305, H-9-T308: transgenic HIGS potato lines.

FIG. 28: Relative sporangia production of *P. infestans* on transgenic HIGS line. The potato line of the variety Desirée were transformed with an RNAi construct in order to form dsRNA against the *P. infestans* gene PITG_19177. After infection with *P. infestans* in the detached leaf assay, these lines exhibited a reduced sporangia production compared with the non-transgenic variety Desirée (mean of 3 biological repetitions). Desirée (non-transgenic control); H-9-T280: transgenic HIGS potato line.

FIG. 29: Plasmid p95N_RNAi PITG_06748 as an exemplary representation of a vector which contains a sense-intron-antisense fragment in order to form dsRNA against a target gene (here PITG_06748). This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.

FIG. 30: Plasmid p95N_RNALPITG_09306 as an exemplary representation of a vector which contains a sense-intron-antisense fragment in order to form dsRNA against a target gene (here PITG_09306). This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.

FIG. 31: Plasmid p95N_RNALPITG_09193 as an exemplary representation of a vector which contains a sense-intron-antisense fragment in order to form dsRNA against a target gene (here PITG_09193). This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.

FIG. 32: Plasmid p95N_RNALPITG_19177 as an exemplary representation of a vector which contains a senseintron-antisense fragment in order to form dsRNA against a target gene (here PITG_19177). This vector additionally contains a CaMV 35S promoter, a multiple cloning site, an intron from the gene AtAAP6 which codes for an amino acid permease in *Arabidopsis thaliana*, a further multiple cloning site as well as a CaMV 35S terminator.

EXEMPLARY EMBODIMENTS

Preparation of Constructs

Figure 2:
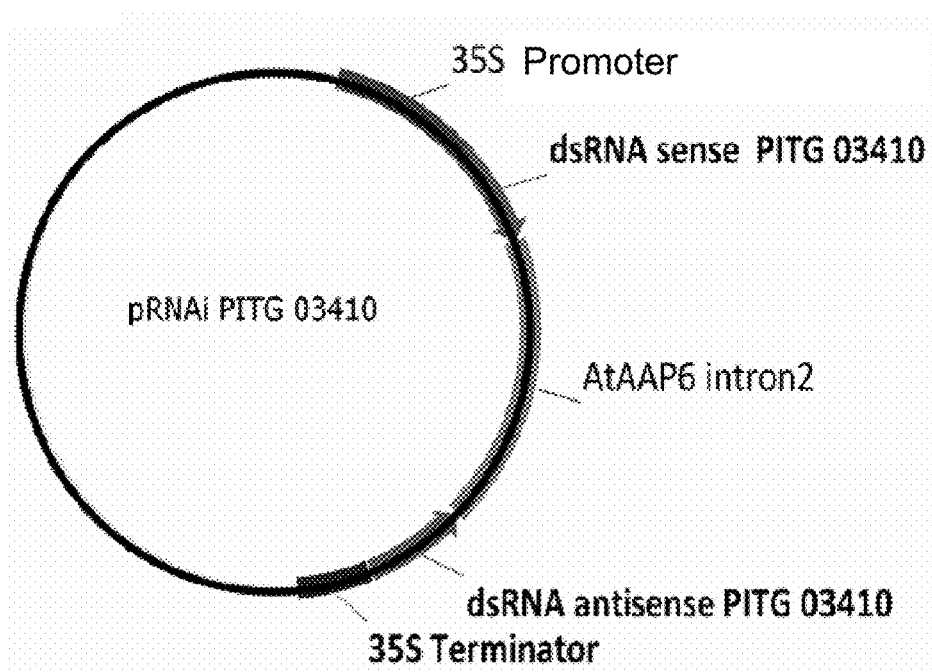

Defined sequence regions of the selected target genes were amplified using PCR and cloned in both the sense and the antisense direction into a pRNAi vector which is suitable for the system of hairpin structures (FIG. 2). In this manner, several fragments with sequence regions from various target genes can be cloned into a vector in order to generate a combination hairpin construct (FIG. 3).

Starting from genomic DNA from *Phytophthora infestans*, a sequence region of 290 bp from the coding region of the gene PITG_03410 was amplified using PCR, cleaved via the restriction enzyme cleaving sites XhoI and SmaI inserted via the primer sequences and cloned into the pRNAi vector (primer 1: cgctcgaggctggatctcgcgctgaggt (SEQ ID NO: 47), primer 2: ttgatatcgcggaaggcgagagacatcg (SEQ ID NO: 45)). This vector contains a CaMV 35S promoter, a multiple cloning site, an intron from the gene AtAAP6 which codes for an amino acid permease in *Arabidopsis thaliana*, a further multiple cloning site as well as a CaMV 35S terminator. This was cleaved with XhoI and Ecl136II and the 4.098 kb vector fraction was separated using agarose gel electrophoresis and then isolated. The ligation solution was transformed in *E. coli* strain XL1-blue (Stratagene, LaJolla, Calif.). The same PITG_03410 fragment was then cloned into the plasmid pRNAi_PITG_03410_sense in the antisense direction. To this end, the fragment was again amplified from genomic DNA from *Phytophthora infestans* using PCR, cleaved via the restriction enzyme cleaving sites XhoI and SmaI inserted via the primer sequences and then ligated into the vector pRNAi_PITG_03410_sense which had been cleaved with SmaI-SalI and then linearized (FIG. 1). The sense-intron-antisense (RNAi-PITG_03410) gene fragment was cleaved out of the pRNAi vector and cloned into the vector pGBTV/EcoRI_kan (FIG. 4). To this end, both pGBTV/EcoRI_kan and pRNAi_PITG_03410 were cleaved with HindIII and ligated so that the plasmid pGBTV/EcoRI_kan_PITG_03410 was generated (FIG. 5). Alternatively, HIGS-RNAi constructs such as HIGS-CoA were initially cloned into the vector pAM (DNA Cloning Service e.K., Hamburg) (FIG. 6). To this end, both pAM and pRNAi_PITG_03410 were cleaved with HindIII and ligated, so that the plasmid pAM_HIGS_CoA was generated (FIG. 7). From the vector pAM, the HIGS_CoA fragment was integrated into the vector p95P-Nos (DNA Cloning Service e.K., Hamburg) by SfiI digestion and ligation (FIG. 8), so that the plasmid p95N_HIGS_CoA was generated (FIG. 9), which was used for potato transformation.

Alternatively to a vector as described above which is suitable for the synthesis of hairpin structures, a section of the coding target gene region in the potato plant can be caused to carry out expression with the aid of two oppositely (reverse) orientated promoters (FIG. 10). In addition, gene silencing can also be envisaged by means of artificial microRNA constructs (amiRNA) using the Web microRNA Designers (WMD3) protocol. Artificial miRNAs are 21-mer single stranded RNAs which can be synthesised in order to specifically negatively regulate desired genes in plants. Regulation happens—like with siRNAs—via mRNA cleavage. These RNAi constructs are then cloned into a binary vector and transformed by *Agrobacterium tumefaciens*-induced transformation in potatoes.

Transformation and Regeneration

Transformation of the potatoes was carried out in accordance with the modified protocol by Pel et al (2009) using the antibiotic kanamycin. The donor material was cultivated in 80 mL MS(D) (25° C.; 16 h day/8 h night; 2000 lux) for 3-4 weeks. For transformation (C1), the internodes were cut out of the donor material in approximately 0.5 cm explants. These were cultivated in petri dishes with 10 mL MS(D) (15-20 Explants/dish) with 70 µl of an *Agrobacterium tumefaciens* culture which had been cultivated overnight at 28° C., which had earlier been transformed with the HIGS-RNAi construct as part of a binary vector such as, for example, p95N, incubated at 25° C. for 2 days in the dark. Next, the explants were dried on filter paper and placed in petri dishes on MSW-Medium with selection antibiotic (400 mg/L timentin+75 kanamycin mg/L) which were hermetically sealed and cultivated for 2 weeks (25° C.; 16 h day/8 h night; 2000 lux) (C2). This selection step was repeated every 2 weeks until the shoots had regenerated (from C3). Regenerated shoots (FIG. 11) were incubated on MS (30 g/L saccharose) with selection antibiotic (250 timentin mg/L+ 100 kanamycin mg/L) to cause rooting and tested by PCR for integration of the construct to be transformed and thus for the presence of the nucleic acids of the invention. The use of the primers Bo2299 (5'-GTGGAGAGGCTATTCG-GTA-3' (SEQ ID NO: 48)) and Bo2300 (5'-CCACCATGA-TATTCGGCAAG-3' (SEQ ID NO: 49)) led to the amplification of a 553 bp DNA fragment from the bacterial NPTII gene, which codes for neomycin phosphotransferase. Furthermore, the sense and the antisense fragment were detected using PCR, in order to ensure that the construct was complete (FIG. 12). The PCR was carried out using 10 ng of genomic DNA, a primer concentration of 0.2 µM at an annealing temperature of 55° C. in Multicycler PTC-200 (MJ Research, Watertown, USA). Propagation of the shoots which tested positive in the PCR was carried out on MS+30 g/L saccharose+400 mg/L ampicillin.

Detection of Processed Double-Stranded RNA and siRNAs

In the transformed plants, the expressed hairpin or double-stranded RNAs were processed over the natural plant RNAi mechanisms in a manner such that these RNA molecules were degraded into small single stranded RNAs. These siRNAs are deposited on the mRNA of the corresponding target gene in oomycetes and thus effect silencing of this gene. The plants are thus placed in the position of protecting themselves against attacking pathogens. By means of this concept, transgenic potato plants can be produced which have an increased resistance to *P. infestans*.

The transformation of potato plants with constructs for the expression of hairpin or double-stranded RNAs should result in the fact that the resulting dsRNAs are processed to siRNAs in preference to the natural plant RNAi mechanisms. In order to measure the fragmentation of the dsRNA, whole RNA was isolated from the transgenic plants using the trizol method (Chomczynski and Sacchi, 1987). 15 µg of whole RNA/sample was supplemented with formamide, denatured and separated electrophoretically in a 1% agarose gel with 10% formaldehyde in 1×MOPS buffer (0.2 M MOPS (sodium salt), 0.05 M NaOAc, 0.01 M EDTA in DEPC dH$_2$O, pH 7.0 with NaOH). The separated RNA was transferred from the gel onto a nylon membrane (positively charged) using the Northern Blot method into 20×SSC buffer (saline-sodium citrate buffer). This was hybridized with a radioactively labelled probe which was complementary to the sequence of the target gene fragment which was present in the sense or in the antisense direction in the construct transformed into the plants. In this manner, RNA fragments which are complementary to the sequence of the dsRNA fragment are labelled and detected by means of a phosphoimager.

The transformation of potato plants with constructs for the expression of hairpin or double-stranded RNAs should result in the fact that the resulting dsRNA are processed to siRNAs in preference to the natural plant RNAi mechanisms. In order to measure the fragmentation of the dsRNA into siRNAs, whole RNA was isolated from the transgenic plants using the trizol method (Chomczynski and Sacchi, 1987). 15 µg of whole RNA/sample was supplemented with formamide, denatured and separated electrophoretically in a polyacrylamide gel with 15% Tris/boric acid/EDTA (TBE) and uric acid in 0.5×TBE. The separated RNA was transferred onto a nylon membrane (neutral) from the gel using the Tank Blot method in 0.5×TBE. This was hybridized with a radioactively labelled probe which was complementary to the sequence of the target gene fragment which was present in the sense or in the antisense direction in the construct transformed in the plants. In this manner, siRNAs which are complementary to the sections of sequence of the dsRNA fragment are labelled and detected by means of a phosphoimager.

In various transgenic potato lines such as, for example, PR-H4 lines or PR-H2 lines, such siRNAs could be detected (FIG. 13 A, B). This shows that the constructs transformed in the plants are recognized and processed by plant RNAi mechanisms such that siRNAs against HIGS target genes from *P. infestans* can be formed which should carry out silencing of this gene in the pathogen.

Measurement of Resistance in Transgenic Potato Plants in the Detached Leaf Assay To test the resistance of the transgenic potato leaves, the transgenic plants were cultivated from in vitro plants in the greenhouse in 5 L pots. After 6-8 weeks, 2 pinnae per plant were cut off and placed in a sealed plastic box on a moist Grodan pad such that the leaf stem was in the moist Grodan material. This ensured that the humidity was high. The boxes were incubated at 18° C. using a day/night program (sunlight, February-September). The pinna leaflets were inoculated with drops of a zoospore suspension (10 μL; $10^4$ zoospores/mL) of *Phytophthora infestans*. After 24 hours, the lid of the boxes was opened somewhat in order to allow a gentle circulation of air in the boxes. The optical scoring and quantification of the zoospores was carried out after 6 days. The optical scoring evaluated the degree of infection and the destruction of the pinna leaf by *P. infestans*. Counting the sporangia led to quantification of the reproductive ability of the pathogen in the plant. In this regard, the previously infected leaves of a pinna were incubated in 5 mL of water in Falcon tubes on a shaker for 2 h, so that the sporangia were loosened from the leaf. The sporangia were then counted with the aid of a Thoma counting chamber under a microscope.

In various HIGS potato lines which were generated by transformation of various potato genotypes, a reduced sporangia count could be determined after infection with *P. infestans* (6 dpi) (FIG. 15B-18B). This indicates that the reproductive ability of the pathogen on the transgenic plants has been restricted.

The gene PITG_03410 was tested as a target gene for HIGS in the genetic background of the potato varieties *Baltica*, Hermes and Desirée as well as the variety Russet Burbank using a vector as shown in FIG. 5. The detached leaf assay applied to these transgenic plants of the variety Russet Burbank showed that the reproductive ability of the pathogen on the transgenic plants was restricted compared with non-transgenic control plants (FIG. 20).

As an alternative to vectors which are suitable for the synthesis of hairpin structures, a vector as shown in FIG. 10 with the target gene PITG_03410 was introduced into potato plants of the variety Hermes and the transgenic lines were investigated in the detached leaf assay (FIG. 21). Here again, it was shown that the reproductive ability of *P. infestans* was limited on the transgenic plants compared with non-transgenic control plants.

Potato plants of the variety Russet Burbank which had been transformed with a combination vector against the genes PITG_00146, PITG_00708, PITG_10447 and PITG_08363 of FIG. 3 were also tested in the detached leaf assay. It was observed that the reproductive ability of *P. infestans* on these transgenic plants was restricted compared with non-transgenic control plants (FIG. 22).

Similarly, the detached leaf assay showed that the reproductive ability of *P. infestans* on transgenic plants of the variety Russet Burbank is restricted when transformed with a vector in accordance with FIG. 29, FIG. 30, FIG. 31 or FIG. 32 which is directed against the genes PITG_06748 (FIG. 23), PITG_09306 (FIG. 24), PITG_09193 (FIG. 25) or PITG_19177 (FIG. 27).

Even on transgenic plants of the variety Desirée which were transformed with a vector as shown in FIG. 31 or FIG. 32 which is directed against the gene PITG_09193 (FIG. 25) or PITG_19177 (FIG. 27), the detached leaf assay showed that the reproductive ability of *P. infestans* was restricted compared to non-transgenic control plants.

Transient Test System for RNAi Vectors in Potato Leaves

A transient test system in accordance with Birch et al. (2010) was developed to investigate the functionality of the RNAi vectors against selected target gene sequences of *P. infestans*. By means of co-bombardment, a RNAi vector targeting a target gene was expressed transiently in potato leaves together with a fusion construct consisting of a luciferase reporter gene and the test target fragment. If the dsRNA construct is processed in the RNAi vector, then the formation of dsRNA and the resulting formation of siRNAs should be ensured. These siRNAs should not only carry out the degradation of the target gene fragment transcript, but also give rise to the fused reporter gene transcript, so that with a functional RNAi construct, a reduction in the luciferase activity can be observed. The plasmid pABM-70Sluci comprises a double CaMV 35S promoter, a multiple cloning site, the coding sequence for the luc gene from *Photinus pyralis*, which codes for a luciferase, separated from a modified intron PIV2 from the potato gene St-LS1 (Eckes et al. 1986, Vancanneyt et al. 1990), a further multiple cloning site as well as a Nos terminator from the nopalin synthase gene from *Agrobacterium tumefaciens*. The PCR-amplified fragment of the coding sequence region, for example of the PITG_03410 gene, was cloned into this plasmid pABM-70Sluci, which was also cloned into the pRNAi vector to produce the dsRNA construct (FIG. 14A).

This transient test system can not only be used for validation of the general functionality of the RNAi construct, but also be used in order to investigate different sequence regions of a gene as regards its silencing effect and finally can select the best sequence regions of a gene for optimal silencing. In addition, the bombardment of transgenic plants stably transformed with a RNAi construct can serve to determine the silencing efficiency of the individual transgenic HIGS potato lines which, for example, can differ substantially depending on the integration site for the construct. In various transgenic HIGS potato lines which are obtained by transformations in various potato genotypes, and which show a reduced sporangia count after infection with *P. infestans*, a reduction in the luciferase activity could also be measured (FIG. 15A-18A). This shows the functionality of the HIGS constructs processed to siRNAs in relation to a silencing of the target gene sequence in the transgenic plants.

When the coding gene sequences which are to be silenced by a combination construct such as pRNAi_HIGS-CoA, for example (target genes: PITG_08393, PITG_00146, PITG_10447, PITG_00708), each cloned into the vector pABM_70 Sluci behind the coding sequence for the luc gene from *Photinus pyralis* (pABM_70 Sluci_PITG_08393, pABM_70 Sluci_PITG_00146, pABM_70 Sluci_PITG_10447, pABM_70 Sluci_PITG_00708) and together with the vector pRNAi_HIGS_CoA, are to be transiently expressed in potato leaves, the silencing efficiency of the combination construct can be analysed on the various target genes. This is also possible by the bombardment of transgenic plants stably transformed with the RNAi combination construct with the individual fusion constructs consisting of the luciferase reporter gene and the test coding sequences of the various target genes.

The luciferase activity determinations were carried out with the aid of Dual Luciferase® Reporter Assays (Promega, Mannheim) (Schmidt et al. 2004).

Measurement of Resistance in Transgenic Potato Plants Under Outdoor Conditions

For the resistance test for the transgenic potato plants under outdoor conditions, the transgenic plants were initially cultivated early in the year (March) from in vitro plants in the greenhouse for 3 weeks in multiport pads. Next, these plants were planted out into a greenhouse with a wire mesh roof in natural soil so that the plants were exposed to environmental conditions, for example temperature, sunlight, precipitation and humidity, which were comparable with field conditions. The plants were planted out in 3 plots each with 6 plants. After 8 weeks, one pinna from each of 2 plants in a plot was inoculated with *P. infestans* by spray inoculation (750 µL; $10^4$ zoospores/mL). Plastic bags were placed over these pinnae to ensure that the humidity would be high and to promote infection. After two days, these plastic bags were removed. Proliferation of the blight by *Phytophthora infestans* in the greenhouse was scored optically and documented photographically every week. The criteria for scoring the infection was initially only on the infected pinna leaf (0: no infection, 1: slight infection (½ number of infected pinna leaves infected), 2: infection on more than ½ leaves of a pinna, 3: infection on all leaves of the pinna) and then the spread of the infection to the plant and the whole plot (4: infection also extends to some other leaves of the plant, 6: infection also extends to other plants, 8: infection also extends substantially to other plants, 10: 10% of the plants infected/destroyed, 20: 20% of plants infected/destroyed, 100: 100% of the plants infected/destroyed).

In various transgenic HIGS potato lines (PR-H-4-7, PR-H-4-11) which were obtained by transformations in the potato genotype Hermes, a greatly reduced degree of infection of these plants during the course of infection with *Phytophthora infestans* was determined compared with the transformation genotype Hermes which had been cultivated, planted out and infected as the control exactly as with the transgenic plants. The reduced degree of infection was initially reflected by a greatly reduced infection capability of the pathogen on the inoculated pinnae (scores 21 days post-infection: PR-H-4-7: 3.3; PR-H-4-11: 3.2; Hermes 7.6) and at later times by a substantially reduced propagation ability of the pathogen to these plants (scores 32 days post-infection: PR-H-4-7: 26; PR-H-4-11: 15; Hermes: 80) (FIG. 19 A, B).

By means of the tests described, not only could processing of the HIGS construct in transgenic potato plants to siRNAs be demonstrated, but also the functionality of these constructs in respect of silencing of the target gene sequence in these transgenic plants, and an increased resistance of these plants to *P. infestans* could be quantified by a reduced sporangia production of the pathogen on these host plants. Since the identification of functional HIGS target genes is not possible without careful testing of their functionality, these analyses as described in detail here are particularly suitable for defining genes which are effective in the HIGS construct and for generating resistant HIGS plants.

REFERENCES

Avrova A O, Boevink P C, Young V, Grenville-Briggs L J, van West P, Birch P R, Whisson S C (2008) A novel *Phytophthora infestans* haustorium-specific membrane protein is required for infection of potato. Cell Microbiol. 10(11):2271-84.

Birch R G, Shen B, Sawyer B J, Huttner E, Tucker W O, Betzner A S (2010) Evaluation and application of a luciferase fusion system for rapid in vivo analysis of RNAi targets and constructs in plants. Plant Biotechnol J. May 1; 8(4):465-75. Epub 2010 Jan. 19

Blackman L M, Arikawa M, Yamada S, Suzaki T, Hardham A R (2011) Identification of a mastigoneme protein from *Phytophthora nicotianae*. Protist. 162(1):100-14.

Benfey, P. N., Ren, L., and Chua, N.-H. (1990). Combinatorial and synergistic properties of CaMV 35S enhancer subdomains. EMBO J. (9), 1685-1696.

Chomczynski P, Sacchi N. (1987) Single-step method of RNA isolation by acid guanidinium thiocyanate-phenol-chloroform extraction. Anal Biochem. 162(1):156-9

Eckes P., Rosahl S., Schell J., Willmitzer L. (1986) Isolation and characterization of a light-inducible, organ-specific gene from potato and analysis of its expression after tagging and transfer into tobacco and potato shoots. Molecular and General Genetics 205 (1) 14-22, DOI: 10.1007/B F02428027

Fire A, Xu S, Montgomery M K, Kostas S A, Driver S E, Mello C C. (1998) Potent and specific genetic interference by double-stranded RNA in *Caenorhabditis elegans*. Nature February 19; 391(6669):806-11

Grenville-Briggs L J, Avrova A O, Bruce C R, Williams A, Whisson S C, Birch P R, van West P (2005) Elevated amino acid biosynthesis in *Phytophthora infestans* during appressorium formation and potato infection. Fungal Genet Biol. 42(3):244-56.

Inoue S B, Takewaki N, Takasuka T, Mio T, Adachi M, Fujii Y, Miyamoto C, Arisawa M, Furuichi Y, Watanabe T (1995) Characterization and gene cloning of 1,3-beta-D-glucan synthase from *Saccharomyces cerevisiae*. Eur J Biochem 231(3):845-54.

Judelson H S, Narayan R D, Ah-Fong A M, Kim K S (2009a) Gene expression changes during asexual sporulation by the late blight agent *Phytophthora infestans* occur in discrete temporal stages. Mol Genet Genomics. 281(2): 193-206.

Judelson H S, Tani S, Narayan R D (2009b) Metabolic adaptation of *Phytophthora infestans* during growth on leaves, tubers and artificial media. Mol Plant Pathol. 10(6):843-55.

Kamoun S, van West P, Vleeshouwers V G, de Groot K E, Govers F. (1998). Resistance of *nicotiana benthamiana* to *phytophthora infestans* is mediated by the recognition of the elicitor protein INF1. Plant Cell. September; 10(9): 1413-26.

Lesage G, Sdicu A M, Ménard P, Shapiro J, Hussein S, Bussey H (2004) Analysis of beta-1,3-glucan assembly in *Saccharomyces cerevisiae* using a synthetic interaction network and altered sensitivity to caspofungin. Genetics. May; 167(1):35-49

Li A, Wang Y, Tao K, Dong S, Huang 0, Dai T, Zheng X, Wang Y (2010) PsSAK1, a Stress-Activated MAP Kinase of *Phytophthora sojae*, Is Required for Zoospore Viability and Infection of Soybean. Mol Plant Microbe Interact. 23(8):1022-31.

Mazur P, Morin N, Baginsky W, el-Sherbeini M, Clemas J A, Nielsen J B, Foor F (1995) Differential expression and function of two homologous subunits of yeast 1,3-beta-D-glucan synthase. Mol Cell Biol. 15(10):5671-81.

Pel M A, Foster S J, Park T H, Rietman H, van Arkel G, Jones J D G, Van Eck H J, Jacobsen E, Visser R G F, Van der Vossen E A G (2009) Mapping and cloning of late blight resistance genes from *Solanum venturii* using an interspecific candidate gene approach. MPMI 22:601-615

Roemer T, Paravicini G, Payton M A, Bussey H (1994) Characterization of the yeast (1->6)-beta-glucan biosynthetic components, Kre6p and Sknlp, and genetic interactions between the PKC1 pathway and extracellular matrix assembly. J Cell Biol. 127(2):567-79.

Saito, K., Yamazaki, M., Kaneko, H., Murakoshi, I., Fukuda, Y., and van Montagu, M. (1991). Tissue-specific and stress-enhancing expression of the T R promoter for mannopine synthase in transgenic medicinal plants. Planta 184, 40-46.

Schmidt K., Heberle B., Kurrasch J., Nehls R., Stahl D. J. (2004) Suppression of phenylalanine ammonia lyase expression in sugar beet by the fungal pathogen *Cercospora beticola* is mediated at the core promoter of the gene. Plant Mol. Biol., 55: 835-852.

Stahl D. J., Kloos, D. U., and Hehl, R. (2004). A sugar beet chlorophyll a/b binding protein void of G-box like elements confer strong and leaf specific reporter gene expression in transgenic sugar beet. BMC Biotechnology 4; 31: 12

Vancanneyt G., Schmidt R., O'Connor-Sanchez A., Willmitzer L., Rocha-Sosa M. (1990) Construction of an intron-containing marker gene: splicing of the intron in transgenic plants and its use in monitoring early events in *Agrobacterium*-mediated plant transformation. Mol Gen Genet. 220(2):245-50

Van West P, Kamoun S, van 't Klooster J W, Govers F (1999) Internuclear gene silencing in *Phytophthora infestans*. Mol Cell. March; 3(3):339-48.

Wang Y, Dou D, Wang X, Li A, Sheng Y, Hua C, Cheng B, Chen X, Zheng X, Wang Y (2009) The PsCZF1 gene encoding a C2H2 zinc finger protein is required for growth, development and pathogenesis in *Phytophthora sojae*. Microb Pathog. 47(2):78-86.

Wang Y, Li A, Wang X, Zhang X, Zhao W, Dou D, Zheng X, Wang Y (2010) GPR11, a putative seven-transmembrane G protein-coupled receptor, controls zoospore development and virulence of *Phytophthora sojae*. Eukaryot Cell 9(2):242-50.

Yin C, Jurgenson J E, Hulbert S H (2011) Development of a Host-Induced RNAi System in the Wheat Stripe Rust Fungus *Puccinia striiformis* f. sp. *Tritici*. MPMI 24(5): 554-561. doi:10.1094/MPMI-10-10-0229. © 2011 The American Phytopathological Society Zhang M, Wang 0, Xu K, Meng Y, Quan J, et al. (2011) Production of dsRNA Sequences in the Host Plant Is Not Sufficient to Initiate Gene Silencing in theColonizing Oomyzete Pathogen *Phytophthora parasitica*. PLoS ONE 6(11): e28114.

EP 1716238 (Bayer S.A.S.) METHOD FOR MODIFYING GENE EXPRESSION OF A PHYTOPATHOGENIC FUNGUS WO 2006/070227 (Devgen N.V.) METHOD FOR DOWN-REGULATING GENE EXPRESSION IN FUNGI WO 2009/112270 (Leibniz-Institut für Pflanzengenetik and Kulturpflanzenforschung) METHOD FOR CREATING BROAD-SPECTRUM RESISTANCE TO FUNGI IN TRANSGENIC PLANTS US 2010/0257634 (Venganza Inc.) BIOASSAY FOR GENE SILENCING CONSTRUCTS WO 2006/047495 (Venganza Inc.) METHODS AND MATERIALS FOR CONFERRING RESISTANCE TO PESTS AND PATHOGENS OF PLANTS

The invention claimed is:

1. A transgenic plant of the species *Solanum tuberosum* or a part thereof comprising a stably integrated first double-stranded DNA and a stably integrated second double-stranded DNA, wherein the nucleotide sequences of the coding strands of the first and second DNA are reverse complements of each other, so that a transcript of the first DNA and a transcript of the second DNA hybridize to form a double-stranded RNA and whereby the plant expressing said double-stranded RNA is resistant to an oomycete of the genus *Phytophthora*, wherein the coding strand of the first DNA comprises:
- (a) at least 23 successive nucleotides of the nucleotide sequence of SEQ ID NO: 1, or
- (b) a nucleotide sequence which is the complementary sequence to at least 23 successive nucleotides of the nucleotide sequence of SEQ ID NO: 1.

2. The transgenic plant or a part thereof of claim 1, wherein the coding strand of the first DNA comprises:
- (a) the nucleotide sequence of SEQ ID NO: 1, or
- (b) a nucleotide sequence which is the complementary sequence to the nucleotide sequence of SEQ ID NO: 1.

3. The transgenic plant or a part thereof of claim 1, wherein the plant or a part thereof exhibits a resistance to *Phytophthora infestans*.

4. The transgenic plant or a part thereof of claim 1, wherein the double-stranded RNA is miRNA or siRNA.

5. The transgenic plant or a part thereof of claim 1, wherein the first DNA and the second DNA are operatively linked to at least one promoter.

6. The transgenic plant or a part thereof of claim 1, wherein the first DNA and the second DNA are under the control of the same promoter and are separated by an intron.

7. The part of the transgenic plant of claim 1, wherein the part is a seed or a cell.

8. The transgenic plant or a part thereof of claim 1, wherein the first and second DNA are complete reverse complements of each other.

9. The transgenic plant or a part thereof of claim 1, wherein the first and second DNA are partial reverse complements of each other.

10. A method for producing the transgenic plant of claim 1, which plant exhibits a resistance to an oomycete of the genus *Phytophthora*, comprising the following steps:
- (i) producing a transformed first parent plant comprising a first double-stranded DNA which is stably integrated into the genome of said first parent plant and which has a coding strand which comprises:
  - (a) at least 23 successive nucleotides of the nucleotide sequence of SEQ ID NO: 1, or
  - a nucleotide sequence which is the complementary sequence to at least 23 successive nucleotides of the nucleotide sequence of SEQ ID NO: 1;
- (ii) producing a transformed second parent plant comprising a second double-stranded DNA which is stably integrated into the genome of said second parent plant, wherein the nucleotide sequences of the coding strands of the first and second DNA are reverse complements of each other, so that a transcript of the first DNA and a transcript of the second DNA hybridize to form a double-stranded RNA and whereby the plant expressing said double-stranded RNA becomes resistant to an oomycete of the genus *Phytophthora;*
- (iii) crossing the first parent plant with the second parent plant;
- (iv) selecting a plant in the genome of which both the first double-stranded DNA and the second double-stranded DNA have been stably integrated.

11. The method of claim 10, wherein the coding strand of the first DNA comprises:
- (a) the nucleotide sequence of SEQ ID NO: 1, or
- (b) a nucleotide sequence which is the complementary sequence to the nucleotide sequence of SEQ ID NO: 1.

12. The method of claim 10, wherein the resistance is resistance to *Phytophthora infestans*.

13. The method of claim 10, wherein the double-stranded RNA is miRNA or siRNA.

14. The method of claim 10, wherein the first and second DNA are complete reverse complements of each other.

15. The method of claim 10, wherein the first and second DNA are complete reverse complements of each other.

* * * * *

SEQUENCE LISTING

```
<160> NUMBER OF SEQ ID NOS: 49

<210> SEQ ID NO 1
<211> LENGTH: 1042
<212> TYPE: DNA
<213> ORGANISM: Phytophthora infestans

<400> SEQUENCE: 1
cgtcaagatg ctgcggaggt ctgtgctgcc gttggcacgt cgtgccttcc cgcggtccgc     60
ggctagccta gcgccgtcct gtgctgctcc caagtacttt tcacgtgcct tcagcgttgc    120
ggagcagagt cagcggcatg tgatcgccgc gctggttgtc aaccagcctg gttgtctggc    180
cgagatcgcc aacctcttcg ccgctcgagg taactatcga tacgcaaaga cgctggccac    240
aggagatcct aaacatggtg tgatgcaggc tacaatattg acagtctggt tgtgggtcgc    300
acggaggtcg aggagctctc ccgtatgacg gttgtcgtca acggcactgc gcagagtgtt    360
```

```
gtcaacgtac gtatagtaat tacagagaca ggagcagtag gtgattgaca ctcaatgtgt    420
ctttgcagat gaagaagcag ctcgaggatg tcgtgtatgt tgctgtggtc aatatcctga    480
gcagtggcaa gaacgctgaa aagaactacg tcgagcgcga cctgatgctg gccaaggtgt    540
ccacggccgg tacgtcggac gctgatctga taccctacca ccaccggaat tcgtgaacat    600
ggacctgacg taaacatttg ctggtgtgtg tgctggctac agaggctgga tctcgcgctg    660
aggtggtgga gcttgccaac ctgttcgacg ccaaggtgat tgacgtgcga ccgcaccagg    720
ttatggtaca actggctggc acccctggtc gcattgaggc atttttggac ctgctaaagc    780
cgctgggtat cacagagatc caccgcagtg ggtcattgc gatggctcgc agcaccagtg    840
tgaccgacga cctgggcgat ctctcgacgt ttgagggcgc cacgcgaacg cttctggacg    900
aggccgatga cgaagagttc gatgtctctc gccttccgcc tggataatat gttggtagag    960
ttatgatcat gccatcacct ttttcttcga taggacttgt gcctgatgac aattgcagca   1020
aggaacgtgc tagcgaagat tg                                            1042
```

<210> SEQ ID NO 2
<211> LENGTH: 3072
<212> TYPE: DNA
<213> ORGANISM: Phytophthora infestans

<400> SEQUENCE: 2

```
atggtgctcc gagcggttcg gctgatcgtc caggcatctc tgctcctgca agtgctccag     60
tgtggcgcct ccgtaactgg tgctcaagta aatgaaaact ttgagaacac tgagcttacc    120
tcgaacgata aactgggaac agtggctccg gccgacatcc cgtcttcaca agacgagaat    180
ctcaagaaac aggaagagcg tggcttcttt gactggtttg gcaatggcga cgacacgcct    240
gccccggctg ctgacgacaa ctccggtaaa tatgcgacta cgacaccgat ccctggcacg    300
gctgcgcggc cgtctacgag tagtctgatg tcaaagtatg gtagtatgct cggtgacttt    360
actaaagaca cgacgccggc ctcggaagcc gatgagcgca caacgagcgc acgtagcgct    420
gccacccgtg ccacctcgga ctcctcttca ggtagtacct ctggcagcgc ggcagcagaa    480
gtcaagccga agagaaagaa gaccaagaag cctgtggttg ccgccgcgtc tgaaagcgga    540
gagagtgcaa gtgacgacga tgccagcgag gcgagcgctt cgggcagtga ggcaaagccc    600
aagaagagga caaccaagaa gacgaggaag ccggtcgtag ctgctgcgtc gacgtctgaa    660
tccgaggatg cctcgacgtc tgaatccgag gatgcttcgg gcagtgaggc aaagcctaag    720
aagaagacaa ccaagaagac tagaaggccg gtagcagctg ctgcatcgac gtctgaatcg    780
gaggatgctt cgggcagctc ggacgagtcg ggaagcgacg atctgtcgga tctgctcggc    840
agctcggcgg gttccggaag cgaagatgac atgtcggccc ttctcggtag cgcgggaggt    900
tccgggactg acgacgcctt atcagctctg ctggggtcgg gagtcggtgg ctcgggtagt    960
atgcttagtt tcgaagactt tatgaagaat tacggtagca tgttcggttc gggaagtagt   1020
gctgtcgacc tgttcggaga cccgagcacg ccccagaaca acacgattga cgacgaagat   1080
atcatcctcg gcgaactgta cggtggcaag gagcacggcg acgccttctc ggacatcagg   1140
aacatcaagt ttggtcagat gatcctgaac attacagttc gcggtcaaga gcgcgtggat   1200
tccattggta ttacagtgat gactcaagaa gctgttggta accttgtgca cggtggtgaa   1260
ggtggtaccg aaggattcat tgaaccggag atgggtgaca ctattgatac cgtcgaagta   1320
cactgggaca agaacaaggg caagacgtgc atcttctacc tcaagatggc gacttctggc   1380
```

```
ggtaagacga ttgcgacggg aacgaagacg gccaacagcg ccgtcatcaa gccgcccaag      1440
ggctaccagc ttgctggatt ccatggtcgt gccagtagtt ctggtatctt ttgtattggt      1500
ggaatcttca ccaagcaaga cgcgacggat ctcgcagtca cggacgtgat ggccatctcc      1560
agtaagggct ctcctgatat ctacaactac gacaccacca ttcgtaactg ggtgggacct      1620
ctagagacag cgagtgacaa cgcctgttac cagaagagag tcgacgtcag cagcaaggga      1680
atgtgtccgt cgggtttcaa caaggacgac gacaggtgca tcacccaatg tcctctcaac      1740
taccccattg actgcttgat ggagtgcatg cctcaaaaca gtgactgcac ccagttgatt      1800
gtcgctaagg tttccgccgt cgttgctgtc gctttaaatg ccgctacgat gggtatcttc      1860
ggtacgctgg tggctgccta cagaaccgct aactttgctc tcacctgcgc catcaacgtt      1920
gtgaacgctg tcaagtcgct gatttactac ctgcgttaca agcagacctt gatcccgact      1980
acggacacgg agaagttgat ggacaaggcg ttccagctgc agattgtcat tcttgacttg      2040
cctctggcta tctgttcttg cctgggcatc aagattcctc ctaagctcca gttctcggct      2100
accattctgg ctgtcgtgtc ggccattgtc atgatggctg tcatggtcgg tgaggccctc      2160
ttcgcgtcgt cgaacaacgt catgctcatg cttcgtgagt cgggcgcttt taacacttct      2220
gctctgaacg gagacaccat tgagcttgat acgttcctca acaccaagaa cggcacgtgt      2280
ggttacgaga tgagaactct cactaaccgc gtcatgggca aggtctacga aatccgtaac      2340
aacacgccga atgctgatgc cgatgatgta cgtgttgagg tgagcaagtc gtccatcatt      2400
acggatgaca tcccccattgt gaccaaccac tgcatgggtg atatctggac caacaagacg      2460
ggcgcgtcgt cgtacaagac gcgcaacctg ctgcgtaaga ccctcagtgt aattgttgac      2520
cagctcgttg aggacggtac gaccgatatg ggtaagcatg tgaccaagaa ggagaaggct      2580
ctcgaatact cgaatatggg tcttttcgtg ctgtccatgt tcgatccgac gggtattgcc      2640
tggatggctt ccgagttcgt gcagcccatt tgtggaccca ctgagtacct gggtgagatc      2700
gatgatggta cgctgtacga cgctctgggt ctaaacacgg tcgaccaggc gttcctggga      2760
agctacggtg tgtggaagaa gaagggtgat ggctccgtca cggtttactt cgagagtgtt      2820
gacaagttcc ctgtgtctgt ggtgatcacg tccggtggtg acaagctcaa ggaggtcaag      2880
gtgcctgcta acggcaacgt cacgtggaca tctacggtgg aggagcttgg tgacaagact      2940
ctttaccttg accgctggcg tcctggtctc tttggcctgc ctggtacggg cggtggttcg      3000
ctactgatgt ggatcccgcg atcgtctgag ggtggccagc ttgttcttca tgctcgcttg      3060
aatgttagct aa                                                         3072
```

<210> SEQ ID NO 3
<211> LENGTH: 2405
<212> TYPE: DNA
<213> ORGANISM: Phytophthora infestans
<220> FEATURE:
<221> NAME/KEY: modified_base
<222> LOCATION: (949)..(1048)
<223> OTHER INFORMATION: a, c, t or g

<400> SEQUENCE: 3

```
atgtcatccg tagacttgag tatcctgcgc aacggcatcc cggccgagct gccggcgcac     60
ccgggcaacc accccgaccc gacgctgccc aaggctccgc accgcaacat cgacggtctg    120
tccaaggacg atctcgtgct ggccgtgcag aacgcgttac ggtacttccc cgagaggttc    180
cacgccactc tggctcccga gttcgcgcag gaactcaagg acgagggcca catctacatg    240
caccgcttcc gtcccgtgca gtacgagatg aaggcgtacc ccattgacca atacccggcc    300
```

```
aaatgcaaac aggcagctag tatcatgctt atgatcatga acaacctcga ccgtcgcgtt    360
gcacagttcc ccaaccacct ggtcacttac ggtggcaacg gtagtgtctt ccagaactgg    420
gcacagtact tggtggccat gcgctacctg tccgaactca cggaacagca gacgctcgtc    480
atgtactctg gtcaccctat gggttgttc cctagtcgtc ctgcagctcc acgtatggta    540
gtgaccaacg gtctaatgat ccccaactac tccacacgcg ctcagtacga caaggcctac    600
gctatgggta acacccagta cggtcagatg actgctggca gctactgcta cattggtccg    660
cagggtattg tacacggtac gaccattact gtactgaaaa cctactgacg aggtctatgg    720
cggttcagat gagagcaatc taccttcctt ctagaaaaat gctaaacaat tccagtggat    780
gttgtatagg tcttgacaat caatattgcc ccctacgatt ttgtcaatat taacaatcag    840
tttatttctt ccaatccctg attttacagt gaggatttcg agagtgggaa cgtgaaaca    900
aaatcattgt caaatttgag cgagccttc tcgccgatgc cagactggnn nnnnnnnnn     960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnngc gtcatctccg gtgtcatctc cgtcactgca   1080
gagatcgacg aatctgcagt gaagaagcgt cacgaacagg gctgggttga cgaggtcgtg   1140
agcgacctgg acgcctgtgt cgttcgtatc cgtgaggcaa aagccaaggg cgaggtggtg   1200
agcttggcgt accacggcaa cgtcgtcact ctttgggaac gtctcgccga cgaggctgaa   1260
gctacgggcg agctgctcgt ggagctcggc tcggaccaga cttccctaca caacccgttc   1320
aacgcggct actacccggt ccagttgtcg ttcgaggagt ctcagcgcgt catggctgaa   1380
gacccggagc gcttccagga actggtacag gagtctctgc gtcgtcacgc tgtcgctatc   1440
aaccgtctga cagccaaggg catgcggttc tgggactacg gtaactcgtt cctattggag   1500
gcacaacgtg ccggcgcgga cgtgttgcgt cccggtgtta agcccgagga ggctgctgtc   1560
tcgactactg cctttaagta ccctagttac gttcaggaca tcatgggcga catttctcg    1620
cttggtttcg gtccgttccg ctgggtctgt acgtcgggtg accacgcgga cctgcagaag   1680
acagacgcca ttgctgcccg tgtgatgcgc gagctgctgg ccgaaccgga agtgccggac   1740
cgggtcgcgg ctcagctgcg tgacaacttg cgctggattg aggctgcaga ggagaacaaa   1800
ctggtcgtgg gatcggaggc gcgtatcctg tacgctgacc gtgtgggtcg cggcacgatc   1860
gccatggcgt tcaacgccgc tgtggctagc ggcgagctct cggcacccgt cgtgctcagc   1920
cgcgaccacc acgacgtcag cggcaccgac agtccgttcc gtgagacgtc gaatgtgacg   1980
gacggctcgg ctttctgtgc cgatatggcg gtgcagaacg cgctgggcga cgccgctcgc   2040
ggagctacgt ggatcgcact gcacaacggc ggcggtgtcg gctggggcga ggtcatgaac   2100
ggtggcttcg gaatggtact ggacggctcg gatgacgcgc gcgagaaggc ggcgtgcatg   2160
ctcggctggg acgtcaacaa cggcgtggca cgtcgtgcgt gggcgcgcaa cgccaacgcg   2220
cgcttcgcta ttgagcgcga gatgaaggcg gaccctttgg tacgtttgtt tggttacgag   2280
cttgagactt tggaagcgtt agatttttaat gtgtgtgtat ctttgtggta ttgcagctga   2340
cggtgacgct ggctaacgag gccgacgacg cgagcgtgcg tgacgctgtg agcaagctct   2400
tctag                                                               2405
```

<210> SEQ ID NO 4
<211> LENGTH: 1735
<212> TYPE: DNA
<213> ORGANISM: Phytophthora infestans

<400> SEQUENCE: 4

```
atgctctcgc agcttaaacg cagattcacc ctgggacgac gttgtcagac cgaagaagaa      60
gaccactcga ggatcaccat gagcctttcc aacagcaaca gtaccagctc cttgcccct     120
gtggacgagc accacggctg tgagtacctg gatacggcgc tgacgatctt tgtaatcggc     180
gcgtcgggcg atctggccaa gaagaagacg tatccgtcgc tctttgcgct ctacaccatg     240
ggctacctgc ctgaacacgc ggtcatcgtg ggctacgctc gcagcgccaa gaatgatgcc     300
gacttccgcg cgcaaattgc gccctggatc aagcctaaga cacccgaggc cgaggctcgc     360
aaggaggcct tcctcaacaa gtgcatctac cgcagcggca aatacgactc aactgaagat     420
gtgggcaagg taagcaagga gatggaggca ttggaagaag cccatggatc gcctgtggcc     480
aaccgcctct tctacttcgc catcccgccc acagtcttcg tgcccatcgg cacgagcatc     540
aagaaggcgg cactgaccac gcgtggttgg aaccgtctca tcgtcgagaa gccatttggc     600
cacgatctcg actcgttcga caagttgtct caggacatgg gcgcgctgta cagcgaagac     660
gagatctacc gtatcgatca ctacttgggc aaggaaatgg tgcagaactt gctcgtgttg     720
cgcttcggca atgcaatctt cgagcccatt tggaaccgca actacgtgtc cagtgtgacc     780
atcactttca aggaagacat cggcactcag gccgcggtg gctacttcga ctcgttcggt     840
atcatccgtg acgtcatgca gaaccacctg cttcaggtgc tgtcacttgt ggccatggag     900
ccaccaatcc aagctgctgg tgacaactac tccaactata tccgtgatga aaggtcaag     960
gtgcttaact gcattgagcc tatcaagatc gagaacaccg tcctgggcca gtatgaaggc    1020
agcaaggagc tcaacgagcc gggctacctc gaggacccga cggtgcccaa gggatcagtg    1080
accccccacct tcgccacagc tgttatgtat gtcaacaacc cgcgttggtc tggtgttccg    1140
ttcatcatga aggctggtaa ggccttgaac gaacgcaagg gtgagatccg tgtgcaattc    1200
cgcccgcctc ctggagcgca gcacttgttc ccaggtgtca agatcccagt acaagagttg    1260
gtgctgcgtc tacagccgga ggaagccgtc tacttgaaga tgaacgtcaa gagtcctggt    1320
ctgcagaccc aggcgatctc aagcgagctg gacttgtcgt acgccgagcg ttacgagggt    1380
gcagaggtgc cggacgccta cactcgcttg atcctggacg tgctgcgtgg taagcaggcc    1440
gcattcgtgc gtgatgacga gctccgtgct gcatggaaga tcttcacgcc attgctgaac    1500
gagattgaga cgcagaaggt gaagccgctg cagtatacgt tcggctcgcg tggccccaag    1560
gagagcgacg agctggtgaa cagagctggc ttccagtacc accagggcga ataccagtgg    1620
cagccgcgtg tgcgcactac cagtgcacta taggttgtct cttttggttga gcacaaagat    1680
gcccggaagt ctggcataaa tatgatggtt gagccagcta gtcttcaata aggga         1735
```

<210> SEQ ID NO 5
<211> LENGTH: 1245
<212> TYPE: DNA
<213> ORGANISM: Phytophthora infestans

<400> SEQUENCE: 5

```
gggagcttaa aagtgctaca ggaagtcgct atcatggcgt caagaagtct cgtccgccgc      60
tcggcgcgtc tcgccactgc catcgctact aagcgcagct tcgttcgcgc cgcttccgcg     120
tcggtgaacc tccagtgctt tcagacagca cccgccactc gccagacccg tcttcagagt     180
acgcagacaa gctccagcga tgagccgccc aaaacggagt ccccagtaga cccagagcag     240
ctcattctgg ccaaggctct ggaccatgtg atttcccacg ggtacgttat ggtttaagtg     300
ctataaaagc gaagatatcc taggttgtaa cgctctcgaa tgcaaggtgg gccattgagg     360
```

```
ctctagcagc tggcgccacg gatcttggct acccttcggt ggctcacggc atgttccagc      420
gcggagctat tgatttggtg gattatttta tggactcgtg tctcgccaag ctacgcgaga      480
cgctgattgt caacacggaa aagttgcagg ccatgacggt gactgaacgt ctcaagtttg      540
gcgtctgcac gcgtctgcag atgctggagc ctgtgttggc tacatggcca caggctatgg      600
ccattggcgc tctaccgcag aacgcacctg gtactgcaaa gagactggcc cagctctcgg      660
atgaaatctg gtacttcgct ggtgacaagt ccacggatct atcatggtac accaagcgcg      720
ctattctcac gggcatctac gctagcacgg agctgtttat gctgaatgac aagtcgccga      780
acttccagga cacgtgggat tcttggacc gccgtgtgga cgaaacgatc caactcggag       840
aactgcctca gaacgtacgt gaagctgttt gagtctctta taaggcttag ctgttgacgt      900
gactaactac ttgtgtgctg gtctgtgtct gagcagctga acgatgtggc tgggatggcc      960
agtattgggc tgcagtcggt gttttcggct gtgacgtcgc ttgcgggtcc tctggccagt     1020
cagatcatct cgaactcgcc tttgagtcaa gttccgaacc cgatttcagc tgtgggcagt     1080
gtggttcctc cctcggttgt atcggctgtt gcctctggaa tgccatttag caatcctact     1140
tctgctggac atgacggtat ggcgttcaag tcgaaggatc tggacgaaat taaccaagag     1200
cttgagaagc tcggcggcct tgacgcgagt gaacgacgga actaa                     1245

<210> SEQ ID NO 6
<211> LENGTH: 1461
<212> TYPE: DNA
<213> ORGANISM: Phytophthora infestans

<400> SEQUENCE: 6
ccacgtccag ctcaagccaa ttgccatgct gtccgctact cgccgcctta cgcgatctct       60
gcgtcgccct tctgcactgg gatgccgcct cgagtcctca ttcgctcccc tcactcagct      120
atccgaggag gaaaccatgt tcaaggacac agtcgcccgg ttcgcggctg acgtggtagc      180
tccgaatgtc cgcgccatgg acacagcggg ggagatggac catgctatca cacgaggact      240
attcgagaat ggactgctgt cggtagagat cccagcagac tacggaggta gcgaggcctc      300
gttcatgaac ctctgcttga ctattgagga gctgtccaaa gtggatcccg tcgtgggact      360
gctcgtggat ctacagaaca cagttgtgaa caacgtcttc ctggtgagtg aagagtacga      420
ttggtattct aaattctgta gctgaccatt gtgttgcagg tgcacggcac ggacgagcag      480
aaagaaaagt acctgccgag actcagcgcg gacatggtgc gtgcatcaat atttggaaat      540
attgtgataa tactaatatt gtacggtgtt gtagatcggc agtttctgtt tgtcagaggc      600
tggatcaggt agtgacgcgt tcgcgctgaa gacacgggcg gaggcctcgc cggacgggag      660
ctactactcc atcactggtc agaagatgtg gatctccaac gccgagtact ctggcgtgta      720
cttggtgttc gccaatgtgg acccgtccaa gggctacaag ggtatcacgt gctttatcgt      780
ggaccgagac atgaaggac tggagatcgg taagcccgaa gagaagctcg gcatccgcgc       840
atcgtcgaca tgtcccgtca cactgacgga tgtgaaggtc ccgaaggaga acattctggg      900
agagctgggc aagggataca agatcgcaat cagcacgttg aatgaaggac gcattggcat      960
tgcgtcgcag atgctgggac tggctcaggg agtctacgac cagacgttgc cgtacttgtt     1020
cgagcgccaa cagttcggct ctcccatcgg agagttccag gcgatgcagc accaatatgc     1080
ggaggcagcg ctcgatatcg agacggcgcg tttgttggtg tataacgcag cgcgtctcaa     1140
ggatgctggc caaccgttcg tcaaacaggc tgctatggcg aagcttcatg cctcgcgtgt     1200
```
ggcagagaag acggcatcca agtgcatcga gctgcttgga ggcattggct ttaccaagta 1260
cttgcttgcg gagaaattct atcgtgacgc aaagatcgga gctatctacg aaggaaccag 1320
taacatgcag ctgacgacga ttgcgaagct tgtgtcggag gaatacaaga ggtaattgaa 1380
tgtcgtgatc ctgtactcag acttgatcct tgtagcaaac caaacaagta acatttccgg 1440
agaacgagcg ttagaaccag a 1461

<210> SEQ ID NO 7
<211> LENGTH: 1580
<212> TYPE: DNA
<213> ORGANISM: Phytophthora infestans

<400> SEQUENCE: 7
atgctgcgtc gtcttgccct ccgtaccgtg aagccttctg tgcgcaactt cgcctccgcc 60
tcggagctgt acaagaaccc gcgcagctcc aagttcagca tgaccaagat cgtggccact 120
atcggccccg tgtcggagca gctggacatg ctacagaaga tcacggacga aggtttgcgt 180
atcatgcgca ttaacttctc acacgccgag tacgacgagg ccttgctgcg cgtcactaac 240
cttcgtgcct gtcgcggcgt gcacgccgag ggtcaggcca aattcaacct acgtgccgtg 300
ctacacgaca ccaaaggacc cgagatccgt acgggtaaga tgcgtgacgg caagaaaatc 360
acgttagaga gtggcaagtc ggtggtgctc acgaccgacc cggctttcga gcttgagggt 420
accgccgaca agttctacgt tacgtatcag cagttagccg aaaccgttaa ggtgggcgat 480
acagtgttac tatctgacgg ccttatccgt ctcacctgta cgtcagtggg taaggatgag 540
attacgtgcc acatccacaa taccgaggaa atcggtaacc gtaagggtgt aaacctcccg 600
ggtttgatcg tcgagttgcc tgctctatct gataaggaca aacgcgacct ggattggggt 660
gtcgagcacg atatcgactt tatcgcggcc tcgttcatcc gtaaggccag cgacgtgaac 720
tcgatccgtt cgttcgtggg agagtgcgtt aagaaacact ggggtaacca acctggttac 780
attgccccta agatcatctc taagatcgag aacctcgaag gtatccagaa ctttgaggag 840
atcctcgagg cctcggatgg catcatgtgt gcccgtggcg atttgggtgt cgaagtgccg 900
gcacagaagg tcctgacata ccagaagatg atggtggacc gctgtaacgc cgtcggaaag 960
ccggttattg tggcgacgca gatgctcgaa tccatgcaga acaacccgcg ccccacgcgt 1020
gccgaagtgt cggatgtcgg caatgccgtg ctggacggcg cggactgcgt catgctcagt 1080
ggcgagtcgg ctcagggcaa gtacccgatc gagtctgtgg ccacgatgaa cacggtgatc 1140
aaggaggccg accagctcct actcaagcct aactaccagg ccaagttcca gttcgagccg 1200
cccacgtcgg acgtcgagtc agccgtgtcg tcggcagtca agacggccaa cgagatgcac 1260
gcgcagctcc tgattgtgct cacccgtacc ggttacacgg cccgaaaggt cgccaagtac 1320
aaaccgactg tgccggtcat gtgcttcacc accgacctta aggtcggccg tcagctccag 1380
atccaccgcg gtctgtaccc ggtggtgccg gactaccttg accgtgcccc gactaccgcg 1440
gaggccatcg ctcacgccaa gaagatggga tggttgtctg ccggcgaccg tgtcgtcgtg 1500
atcagcggcg acaagctgtc ggacgatctc ggccgggaaa tcctcatcgg cgtcgctgac 1560
gtccagtaag acggagacaa 1580

<210> SEQ ID NO 8
<211> LENGTH: 900
<212> TYPE: DNA
<213> ORGANISM: Phytophthora infestans

<400> SEQUENCE: 8

-continued

```
atgtggtcga cgatgatcat gcggttccct acgcaggcca agtccgtgtc gcgcagcgcg      60
cttgtggcgg caggtatggc tgcgttcgct gccttctcca gtgtttcctc tactcgctgc     120
gaagaggaga agtccaaggt ggcgttgagc cccaaggagt tccgttcttt cactgtgcgt     180
aaagttgaga ccgtgaacta caacacgaag cgcgtgacgt tcgctcttcc cacacccgag     240
cacgagatgg gtctcacgac gcctagttgc cttatggctc gtgccaaggt agacggcaag     300
acagtggtgc gcccctacac gcctgtcaac gtgaacgacg agaagggttt cttggagctc     360
gtagtcaagg gttacccaca gggaaagctc agcaagcaca tcgtgcagct caaagaagga     420
gactctcttg acatgaaagg tccctttccc aagttcaatt actaccccaa caggtacaag     480
agcatcggca tgatcgctgg cggctccggt atcaccccca tgctgcagct catcaaggcc     540
atttgccgca acccggagga ccgcaccgag atcacgctgc tgtactgcag tgtctcggaa     600
gaagatatca tcctgcgtga agaagtggag gccatgatgt acctgtaccc gcagatctcc     660
gtgatccacg tgctcagcaa cccgtccgcc gagtggaagg gtcttacagg cttcgtgtcc     720
aaggagatga tcgaaaagta catgccggag ccgtcagacg acaacctcgt gtgtgtgtgc     780
ggtcctccgc caatgatgta ccacgtctcg ggtgacaagg cgaaggacag gtctcagggc     840
gaactgcaag gtctgctgaa agacatgaac tacacctcca ctcaagtgtt caagttttaa     900
```

<210> SEQ ID NO 9
<211> LENGTH: 1245
<212> TYPE: DNA
<213> ORGANISM: Phytophthora infestans

<400> SEQUENCE: 9

```
gtcgagcaca agaccaacac tcctgcacca tgactaccct caagatcgtc gtttccggcg      60
ccgccggcca aattgcgtac tcgttgctgc ctctcagtac gtccgtctcc ttccctcttg     120
tgtcttctcc ataccctaac gtctcaccat gttgcagtct gcatcggcca cgtcttcggc     180
cccaaccagc gcgtggagct gcgcctgctg gacatcgaac ccgcccagga agcgcttgag     240
ggcgtcaaga tggagctcca ggactgtgcc ttcaacctag tggacgctat catccccaca     300
gccgatctgg agactgcttt caaggacgcg gacgtcgcaa tcctcgtggg cggcttcccg     360
cgcaagcaag gcatgcagcg caaggatctg attgagaaga atgtagccat ttttaaggct     420
cagggagctg ctatcgacca gttcgccagt cgcgacgtta aggtgcttgt tgtggccaat     480
ccagccaata cgaactgcct cattgccatg gagaacgcac ccagcatccc gcggcgcaat     540
ttctcggcac tgacgcgtct ggaccatgag cgtttgcgct cgttcctagt ggagaaggtc     600
aacgagaccc aaagcccgaa agttacgtcg aaggacgtca acaaggtcgt gatctggggc     660
aatcactcga gcacgcaagt gcccgacgtc acgaacgcag aagtgaaggg ccagccgctt     720
gataagatcg tctcggacaa ggattgggct gagaagaagc tcgtcaagga cgtgcaggag     780
cgcggtgcag ccatcattaa ggctcgcaag ctctcgagcg ccatgtcggc tgccgccgct     840
atcggcgccc acctgcgcga ctggttcaat ggctccaagg acggcgagct cgtgtctatg     900
gccatttgct cggacggcaa caagtacggt gtgcccgagg ggctcattta ctcgttccca     960
gtcaagtgcg cgggcaacgg cgcgtacgag gtggtgaacg gtcttcccat ctcgccgcgt    1020
atcgacgcaa tgatgaaagc cactgcgcag gagctgacag aggagaaggc cgacgctgtg    1080
gagatcctgt cgcgccagtg agcagtattc agctaatagc tggacgatgg caacgtcgtc    1140
tacaccccat tcgatttttt tctcccatta tgagctgctt caatcgttta tttgaccatc    1200
```

```
taaaccaatt aatttcttgt tattacgatt tcttattgaa aaaaa            1245
```

```
<210> SEQ ID NO 10
<211> LENGTH: 1280
<212> TYPE: DNA
<213> ORGANISM: Phytophthora infestans

<400> SEQUENCE: 10
atgtcgtctt cattttgtca gctatccaag cgcgtgctgc agtatcttcg acatgagcat   60
ccacatcgtc tatttccctc catcggtcga agacgcaaac tcccaggcat aaacctcgac  120
ggaagatctc agcggtgatg gcgcgtggtt agccgcaagg tgttccgatg cacaccacac  180
actactcgcg aaaacgacca tacttctgtc ggccagggta acctctgggg agctgcacaa  240
cggccgtctt tttagcttat tttagcgagc aacaggttg tgcctcattg ccacgtgtt  300
cacgcacgta cgtcacgtgt gtgctcattt taatattaaa gatcccgttg aagacgaaaa  360
gcttctttgc tggcatcatg cgcttccaga cgttgttgct cgtccttgtc gcactagtca  420
tcgccccgtt tcaggccctg tctccaccca gcgagtccaa cgtgccgttc actcttcggt  480
acgtcccggg cttctttaaa caaggtaccc cgtccgtgga gattccacct tcaaattcaa  540
ggcatctcgg gctacttgac aacgtcacgt ggacggatgt agacgcctac attgctgcac  600
gagccgctca aggcgtggac gtcaagttgt tcctcttctt acgtcatgga aaggcctcc  660
acaacgtcgc cgaagccact tacggcaccg aagcctggga cagattctac agcaaactag  720
cgaaatatac tgacgccaag ttgacgaaac ttgggatgca acaggctgtc aaagcgtcgg  780
aaaggatcga cgaggagctt aagagaggac tgagcctgga ggaagtcgtg gtttccccgt  840
tggagcgtac actacatacg gcaatgatcg cgtgccagaa tcaccacgag atcccgaagc  900
ggtcgatgga atggccccgc gagaccatcg gcgtctgcac gtgcgactta cgcggcacca  960
tctccgccaa ggccgagctg tacccaagta tcgacttcag tgatatctgg agtgatgcag 1020
acccgtggtg gacgcctgat catcgtgaga ccgagctgca catcaacgac cgcgctcgca 1080
tcttcctgaa ccgcgtcttc tacggtcaca agtcagtgcg tgttggtgtg gtgacgcaca 1140
gtggactaac caccgccgcg atgcgtgtca ttggccatcg taagtacagt gttgcgacgg 1200
cggaagtgat accgttcctg cttgaagaca ccacggtgca cacgatcctg tcgatcttct 1260
ctggtaaaga agacatgtag                                              1280
```

```
<210> SEQ ID NO 11
<211> LENGTH: 1016
<212> TYPE: DNA
<213> ORGANISM: Phytophthora infestans

<400> SEQUENCE: 11
atgtcgtcct atcgtgctgt ccaagttgta aagttgacta aggacttccg cgccgctacc   60
agaatcgtga gtgtccccga actacccacc gctgggcccg acagcatcgt tgttaagaac  120
cgcttcttgg gaattaactc gaccgacgtc aatcttacga atggcatgta tcatgacaag  180
ctgccgtttc tcgcgggcgt tgaaggtgca ggtctcgtca ctgaggtcgg gagtaacgtc  240
acgactgtga agtgggcga cgctgtcatg taccagacgc tgggagccta tgcggactac  300
gtacaagtgc ccgtgtcggc cgccatcaag atcccagagc tgtcgaagaa cgctctaccg  360
gttgcagtgg gcgcgtctc tgcgtccatc tgccttgaat gtctcggtga gatgaagtcg  420
aatgagaccg ttcttgtgac tgctgctgct ggggaaccg gacagtttgt cgtacagctc  480
gccaaacttg ctggcaacca tgttatcggc actaccagct ctgacgagaa agtggaggct  540
```

```
ttgacgaaac tgggctgcga ccgtgtaata aattacaaca aggagaatgt cggcgatgtg    600
ctaaagaagg agtatccgaa tggagtagac atcgttttcg agtccattgg aggcgacatg    660
ttccgtgctg ctgtcgataa cattgcagtc cgtggtcgta tcatcaagat tggcttcatc    720
tcgcgagtat tggagaccaa agacaagacg actcccaag gccgcctccg ctgctatcgt     780
gggaagcgaa caagaagatt ctgatgaagt ctgcttccat ccgagggctc ttcatgtatc    840
actttgagga acacattcga gagcacacgg agcgattgct gaagctcatt agcgagggca    900
cgttgaagcc tggcgttgac cccactacgt acaagaaatt cgagtccatt ccgaatgcaa    960
tcgaccgcat gttcgcccgt gaaaatgtag gcaaactcat cgtagagctc gagtag       1016

<210> SEQ ID NO 12
<211> LENGTH: 267
<212> TYPE: DNA
<213> ORGANISM: Phytophthora infestans

<400> SEQUENCE: 12
atgggcaagc acacggagcg agccaaggag agtccattca agcagcagtc gatgatcctc     60
gtgcctatgg acacaccagg cgtgcaggtc gtgaagccca tgcatgtctt tggctacgac    120
gacgcaccgc acggacacat ggatatgctg ttcaaggacg tgccgtgtgcc gttcagcaac   180 gtgttgctcg gtgaaggtcg cggctttgag atcgctcagg atcgtcttgg acctggccgt    240
atccaccact gtatgcgagc catctga                                        267

<210> SEQ ID NO 13
<211> LENGTH: 1147
<212> TYPE: DNA
<213> ORGANISM: Phytophthora infestans

<400> SEQUENCE: 13
atgcgcaaaa tattgaatat tgattggtta aaacctggtc ttggcatcct tatgaccaat     60
tacagttatt gagtgcttta agcggggcag acgtccacta cgtcacactc agaatctcca    120
cacaagcaac agaccgacac aatgagcagg tgcgagtggc atcccagcaa cttcgtgcaa    180
atttagcctt gttatattaa ttgtataacg tggcatgttg cagaccgacg atctcagagg    240
ttatcgccga gcggaaggcc aacaacactg cggctttcat caccttcgtg ccctgcggct    300
tcaagactaa ggctgacaca gtggacattc ttctgggact gcagcgcggc ggcgcgaaca    360
tcatagaggt gggcattccg tactcggacc acaggccga tggcccgacc atccagcgcg     420
cacaccaggt gggcgtggac cagggcatca cgctgcatga cgtcctggcc acagtgagcg    480
aggcgcgaac taagggcctt actacgcctg tggtgcttat gggctactac aacaacattt    540
tgcagtacgc cgaagtcaaa atctgccccg acgcccagaa aggtacgcct gtaatcgacc    600
acaggagaga tttgtgggct caaaaactga caataaacgt atttgtagct ggggtggacg    660
gattcattat tgtggacctg ccgcctgagg aggcaaagac gctcagtgac gacgcagcta    720
agcacggact tgcgtacatc ccgttggtgt ccccaacgac gacggaggag cgtatgaagc    780
tcatcgactc ggtggcacat ggttttgtgt attgcgtgag tctcaccggt gtcacgggcg    840
ctcgtaacga gctgcctccg aacctcgacg cgttcatggc caagagtaag ttgcttttcg    900
cgctttagtt tattttaatt gtcgagctaa cgtggtccct tgattcgctg cagttcgtgc    960
caacgtgaag caccctctcg ctcttggctt cggtctgtcg acccgccagc acttcgttca   1020
agccagcgcg cttgcggacg gcgttgtgat cggctcgaag attgtcaaga tcatcgagga   1080
```

```
cgcgcctgac acagccacgc gtgctgccaa tgtggaggca tttgccaaga gcatcgtgaa    1140
cccttag                                                              1147

<210> SEQ ID NO 14
<211> LENGTH: 1917
<212> TYPE: DNA
<213> ORGANISM: Phytophthora infestans

<400> SEQUENCE: 14
atgggtaaca tcctggagga gatcgcagcg cagcgccgtc tggacgtggc ggccgccaag     60
caggtcatat ccgccgatga tctggccaag aagatcgagc acgcggaggt cgttttcggc    120
tcgaccctgc ccgtgcttga ccgccttaac gcacccacgg tgcgtccggc agtgcaggga    180
atctggagaa gaatctgcgt ctaacgcagc taccgctgta ctgtattttt tccttgtatt    240
tatggcagag agaggggtgg tccgacgtgg ctctggctgc cgagtttaag cgtgcgagcc    300
ccagcaaagg tgacatcgcc acggagctca atctgcgtga gcaagtgcag gcctacgcca    360
acgcaggtgc cagtatgatc tccgtactga cagagcccaa gtggtttaag ggatcgctag    420
acgacatgag ggcagcccgg gaggtggtcg agggcatgag tcagcgtcct gccatcctgc    480
gcaaggattt catcatcgac gtgtaccagt tgctggaggc ccgcgcttac ggagcggatt    540
gcgtgttgct catcgttgcg ctgctgtccc aggagcagct tatcgagctc attgacgtac    600
gtcgccccgc ttgcactaca gtagtgggt ttactgtaca ctgacaagcc tcttgttggt    660
ttgtaggcca cccacaatct cggtatgtgc gctctggtcg aggtgaacag catccaggag    720
ctggacatcg ctctggctgc gagggctcga ctcattggcg tcaacaaccg cgatctccgc    780
acgtttaagg tagacatgaa cacgacggct cgcgttgcag acgctattcg tgagcgtggg    840 cttttcgctgg gacgtgacgg cgttacgctc tttgctctca gtggcattcg ctcgcacgca    900
gacgtggtca gtacgagaa gtgcggcgcc cggggcatct tggtgggcga gtacttgatg    960
aagagtggtg atattgccgc gacggtgaag gatctcttgc agaatgtgac gcgtcacacc   1020
gagtcgggcg aattcgcttt ggctcctccg cttgccaaag tgtgcggcgt cacgacagtg   1080
gagtacgcgc tggcggcctt gcgtaatggt gccaatatga ttggtatcat catggcggaa   1140
cactcacccc gctatgtcca agtggaggaa gccaaggcca ttgcccaggc tgtgtgggag   1200
tatggggagc gcacgggccc tattctctca gacattgtgg agactcactt ggacggcaag   1260
aacgactggt tcatagaaa tgtccttgcg ttgcgtgaag cttgctcgcg tgcacctctc   1320
gtggtcggag tgtttgtcaa caagacagct gccgagatga acgcgactgc aaaggaaatc   1380
ggactggact tggtacagct acacggcgac gaggggtttc agatctgcag ggacattaag   1440
taccccacca ttcgcgcgtt gcatctgccc gacaccacgc tctgcgacgg cgtggacgca   1500
gaagccgttc tacagcaggt tcaggaaggc cttgccaact acattctgct tgatacgacc   1560
gtgaagggtc agcagggcgg cactggcgtc acattcgact ggaagattgc agccatcttt   1620
gcgcaggcac gacttccctg cctcatggct ggtggcctta cccctgagaa cgtggtgaag   1680
gctctatcgg tcggtcaccc cgttggggtg gatgttagca gtggagtgga agtgaaaggt   1740
tcacctggtg tgaaggatat ggacaaggtg actgcgttcc taaaggctgt gaaggattac   1800
ctctcgattg ctacgcttaa gatcgaggag gagacggaaa cctagagaga gaccctcgga   1860
gtgttctaat caatgagggc cactaatgaa gtgcttttac gttacgagct tggatgc      1917

<210> SEQ ID NO 15
<211> LENGTH: 1494
```

<212> TYPE: DNA
<213> ORGANISM: Phytophthora infestans

<400> SEQUENCE: 15

```
atggtgcact atcgtagtac tcgcggcggc gtccgcggcc ttagctttga gcaggcggtg      60
ctgacgggct tggcttccga ccgtggcctg ctgatacccg aagctgacga gttccctacg     120
cttccagctg atgcgctgga gaagtgggcg tctctttcgt accaggaatt ggccgtggag     180
gtcatgcgcc ttttcattga cgaaagcgag atctcgcgtg accagctgcg tgagcttgtg     240
accaagagtt acaacgcgac cacgttccgc tccgatgagg tggcgccggt ggtcaaggtg     300
acggatcaaa tgctggtgct tgagctcttc catggcccca cgtttgcctt taaggatatc     360
gctctccagt ttctaggcaa ccttttcgag tttttcttaa agcgcaagaa cgaggcgctg     420
ccttctgacg ctcctaaaca ccagatcaca gtcgtgggcg ccacctcagg cgacaccggt     480
agctcggcca tatacggtct ccgcggcaag gagaacgtcg aggtgttcat cctcttcccc     540
gagggtcgtg tgagcgccat tcagcagcga cagatgacta ctgtattgga ccagaacatc     600
cacaacgtgg ctgtgaaggg cacgttcgac gactgccagg ctatcgtcaa ggaccttttt     660
gccaacgctg acttcaaggc caagtacaac ctaggtgccg tcaactcgat taactttgcg     720
cgtatcttgg cgcagatcgt gtactacgtc tgggcctact tccgtgctca cgacgagggt     780
gttagcggcg aggttgcctt ctccgtccca acaggcaact tcggtgacat ccttgccggt     840
ttctacgcca agaagctcgg tgttcccatt ggcaagctga ttgtggctac caacgagaac     900
gatatcctgc accgcttttt ctccacagga aaataccacc gccgcgacat cgagcacacg     960
atttccccgt ccatggacat ttgcgtgtcg agtaactttg aacgttatct cttcgctctg    1020
tccggcgaga accacgacat tctacgcggc tggatgcagg ctttcgagca gactaatgag    1080
ctcacgatct cgggcgagct gctctccaag gcacaagacg agatggcatc gtatgcggtg    1140
cttcaggagc aggtgcgctc cactattgcg gagtacaaaa cgatgcatca gtacctcttc    1200
gacccgcaca gcgctattgg cgcagcagct gccatgcact ttgtccagga taaccttgca    1260
gacaagccaa actcggcggt agttgtagtc ggcactgccc actacggcaa gttcctcccc    1320
gtggtgtcga aggcactagg tgtcgctgag tcagagattg agcaacaccc gatcctcaag    1380
gcgctggaat cactgcccac ccggctttcc gttgccagca actcgagtga aactgtggct    1440
gagcatattc gcaagattat tgctgagaag aacgacgaag cctgtagtga ttga          1494
```

<210> SEQ ID NO 16
<211> LENGTH: 1299
<212> TYPE: DNA
<213> ORGANISM: Phytophthora infestans

<400> SEQUENCE: 16

```
atgagctcgt tccgtcttcg tattgccaac gcgcgccaga tcgttcaagt ttgtgcgaac      60
ggcgagccgt ttaagaccgg cgcggcccaa aaggatctgg ctgtgctcga gaatgcgtca     120
cttgtcgtgg acaaggcagg taagatcgcc ttcgttggtc ctgccgctga cgtagagaag     180
tggctgagca cgcagctgca gcccgtgagc tttgagaagg acgtggacgc tcgtgacatg     240
gtcgtactgc cgggttttgt ggatgcgcac acgcacccag tgtggagcgg caaccgtgtc     300
aacgagtttg ccatgaagct ggctggcgct acctacatgg aagttcacga gagcggcggc     360
ggcatcaaca acacggtgcg tcacaccaag aagagttcag aaactgagct gttggagctg     420
ctgcgtacgc gactagaccg catgttgcgt agcggtacga cgcttatcga agcgaagagc     480
```

```
ggatacggtc tcgagactga cactgagctc aagatgctgc gtgttttaca ctccgcatcg        540
acgggtgaca acgcacaccc tgtggagatc gtgtccaact acctgggtgg tcactcggtt        600
cctgacggca tgactgctgc tgaggccacg gaggatatca tcacgaagca gattcctgct        660
cttgtgcagg ccaagaagga cggcaccatc tcgcccgaat tcatcgacgt gttctgcgag        720
aagggtgtgt cgagcacaa cgactctcac cgtattctag aggcaggcaa gaaggcggga         780
ttggacatta acttccacgg tgatgagatg tgtccgatgc agtccggtac cttggcggca        840
actctgggcg cccgtgcaat ctcgcactgt gagatgctga ctgctgagga tcttcaggct        900
atggcagcgc acaagccaga gcctgtattc gccgtgcttc tgcctactac caagtatatc        960
ctgaagctgc ccaatccgcc agcacgcgac atgatcgctg ccggtgttcc tgttgctctg       1020
ggcagtgact acaacccgaa cgctcattgc ctttccatgg cactgaccat gaacatggca       1080
tgtgtgctgt tcggtatgac catgaaggag gctcttgtag gcgccaccat caacgccgct       1140
gcctccatca accggtcggc tactcacggc agtctcgagg tcggcaagca gggcgacttg       1200
gtcctgatgc gtgctacgca gtgggagcag atcatctacg aaatgggcga ccctcctatt       1260
gaacacgtag tgaagaaggg agttgtctac acgaagtag                              1299

<210> SEQ ID NO 17
<211> LENGTH: 1846
<212> TYPE: DNA
<213> ORGANISM: Phytophthora infestans

<400> SEQUENCE: 17
gcaacgaaca agtctcttcg ttccacttcc gtttcacctc gtcgtcatgg ccatcgccaa         60
ttcgaacacg aagtctgagc tcgttctgga cggcgagtct ctctgtgctg aagacctggt        120
gcagctgtcc aagggagaca cgagaatctc gctaagtcaa gaagcctgga agcgcgtggc        180
ttgtggccgt gaggtcgtgg acaatatcct caaggacaag actcgtgtgg cgtacggtat        240
taacacgggc ttcggactct tctccaacgt cattatcggc cccgagaagc tcacagagtt        300
gcaggaaaac ctcatccgct cgcactcgtc tggcacaggc gagccgttga cattcgctca        360
gacgcgtatg ctgctcgcgc tgcgtatcaa tgtattggct aagggacact cggggatccg        420
tgtgcacact ctggagcagc taatagacgc cttttaacgcc gactgtctgt ccgtggtgcc       480
agccagaggc actgtgggcg cctcgggcga cttggctccg ctagcacacc ttgcactcgg        540
tatgatgggt gaaggaccca tgtgggataa ggtggatggt cagttcgtca tcagcgaggc       600
ctccaaggtc ctggccaagc acggactgaa gcctgttcag ctcggagcaa aggaaggtct        660
ggctatgatc aacggcacac aactcatcac gtcggtgggt gctgaggcgg ttgtccgtgc       720
tcagaacgtc gctaactgcg ctgatatcgc cgtcgcattg acactcgagg tgctctgcgg       780
tactgtcaac gccttccacc cgcgtattca tgcagcccgt ccgcacactg gccagatgct       840
cgttgcctcg cgtattcgca cactactacg tgctgacaac ccgtccgagc tgttccgtag       900
ccacaactac gaaggaaagg tgcaggacgc ctacactcta cgttgtgcgc ctcaggtgca       960
cggcattgtg cacgacacga tcaacttcgt acgtggtgtg ctggacgtcg agatgaacag      1020
tgccacagac aacccatgg tcttcacggg tagtgccgag gtcacgacgg atctgtctcc       1080
ttcaattgac acgaatcaag tcaagcccaa catcgaacag gtagaacacg agatcacgga       1140
tctgaatgac gccaaggagg agatcaagcg tcttaaggct cttgttgcac agaagcagaa       1200
gcctgtggaa cacccggcgg cgggtatgaa gcgcacatcg gacacgttct accgtggcgg       1260
cggtggcttt gtcatctctg gcggcaactt ccacggcgag tatccggcta aggtgctgga      1320
```

```
ctacctggca attggtatcc acgagattgc tagcgttagt gagcgtcgta ttgagcgtct    1380
agtgaaccca acgctcagca acctgccggc tttcctcgtg ccagagggcg gtctgaactc    1440
gggttttatg attgctcact gtacggcagc cgctctggtt tcggagaaca aggtgctcac    1500
acacccgtcg tcggtggact cgatctctac gagtggagcc aaggaggacc acgtgtcgat    1560
gggaggcttt gctgctcgta aggcgcttac ggttgtggag catgtcgaga ctgtagttgc    1620
tattgagatt ctggcagcgt gtcaagccct tgacttgctg cgtccgctgc gtacgacgga    1680
ggctcttgaa gctgtccacg gactggtacg caccgcgtg gctaggtttg acaaggatcg     1740
cttcatgaag cccgacattg acgccgtgct ggacctcgtt cgtagtggag ctatctgcga    1800
cgttgtagct ccgttcttgt caaaactgca cgtgtcagga ctttaa                    1846
```

<210> SEQ ID NO 18
<211> LENGTH: 1218
<212> TYPE: DNA
<213> ORGANISM: Phytophthora infestans

<400> SEQUENCE: 18

```
ccgcacagag caactgccac taggcatcat gctgcaccga cttggccgcc gctcgactgc      60
cacttccgcc cagcggtcac tgcgccgatc agccatgacg ccaccgcagc gccaatcctt     120
tcatttcagc tcgtcagcac gcaagccggc atctttggat gctcagaacc gcgtagctgg     180
tgctgcctcc ttttcctgg acgccaaggc cgtttgcaag ggcaagcgct gtgcattggg     240
caagaacaac agcggtattg gagctaaccc ggccacatgc ggggaggatt cgttcttcct     300
cacacctgac gtggtgggcg tggctgacgg cgtcggtggt tggaacgaga acggcgtgga     360
tccaggcaag atatcgcgct cgctaatgcg caacgcggca ttatttgtgc agcagcagac     420
ggccaatagc gagagtgcca ccacgcaaca ggttctggct cacggctaca agcaggcgct     480
gctggatgac gaggtggagg cgggtagcac gacagcctgt atcgtgagac tgaagcagtc     540
gtctgagggc aaacccgtgc ttgagtactc gaacctcgga gattctggct tcgtggtcat     600
ccgcaacggc gagataatct ccgcagtaa atttcaggtt cgaattgact gttgggagtg     660
acagtagaag agttactgac ggcgttgctt tagtattatg gacgtgctcc gtaccaactg     720
gcaaagatcc ctctgcggtt taagcagtat ggtgctattg agaatcaccc tgatgatgta     780
agtctgcttc gcatttggat actatttatg ctggagacag tacaatgcta acggttattg     840
ctccaggcgg actcgggtga gattgacgtg caagacggag acctcgttgt actagccact     900
gatggtgttt gggacaactt cgcccccgac ctccagaaag ctccttcgca gttcccggta     960
agattcttta ccgccgtgtt cgagctacct gtaattactg actttgtttc tcgttattgt    1020
ctgctatttc taccgtagcc gatgctctcc tggcgaagat attggtcagg tgaactcgca    1080
tcttttgtgg atgttattgc agagaaccc gacaaggctg ccgaaaatat cgtcctggcc    1140
tcgctccgcc acaaccttaa gcccgacgac atcactgtcg tcgtggcaaa ggtagtcgtg    1200
atggcatcaa agctgtag                                                  1218
```

<210> SEQ ID NO 19
<211> LENGTH: 735
<212> TYPE: DNA
<213> ORGANISM: Phytophthora infestans

<400> SEQUENCE: 19

```
atgaagcagt tactgcagcc gatctcgttc tctggtgctg cgagtgtgtt cgtcgtggtg      60
```

| | |
|---|---:|
| gcaaagcaac gcaagaaacg ctgccgtgcc aatgacaagg aagatgacgc tgttaaggac | 120 |
| gacgaagaga ctgagacagc agaggacgaa ctggacgagg aagaccaacc cacgcgactg | 180 |
| tacgtggcca atgtgggcga ctgtcgagct gttttgtgca ctgcagacgc cttagcagtc | 240 |
| gacatgacga cggatcacaa ggcgtcgcta ccggctgaac aggagcgtat cgaggcgtca | 300 |
| ggtggcttcg tgcacaacgg ccgactggac ggcattctgc agatctcccg tggcttcggt | 360 |
| gacttggcgc acaaacagga tggccacttg gtggtcacgc cagatgtggt ggagcatctc | 420 |
| gtgaacccgt cggaccagtt cttgctgctt gcaagtgacg ggctcttcga cgtgttgacg | 480 |
| tcgcagcaag ctgtcaactt tgtgctgcgt aaacttcaga cccatggaga cgtccaactc | 540 |
| gcagctcagg agctggtgct caaggcgcaa gcttacttcg cacacgataa catcagtgtg | 600 |
| gtcattgtgg cgttgaacca gaaaggtgac gcgtgaaatg aacagcggct tctattgact | 660 |
| acggaagatc ggagaccgac gaagaagcag aaaacccgga gatcaagctc gagatccaag | 720 |
| aaattatgaa caaga | 735 |

<210> SEQ ID NO 20
<211> LENGTH: 1845
<212> TYPE: DNA
<213> ORGANISM: Phytophthora infestans

<400> SEQUENCE: 20

| | |
|---|---:|
| atgcgacgca aggagaccaa ggtgttgttg acgctcgaag aggtgcgcga ggccttcgag | 60 |
| cagcagacgc cgctggccgt caaggacgcg ctgggtgtca ttcatgaggc gcagttcatc | 120 |
| atgaacctgg agccgaacct tgtggccgtg cggcaaagag cttcaacata tgtttttgga | 180 |
| gatatccatg gccagttcta cgacctgatg cagctgatgg acgccgttgg cgttgccgac | 240 |
| ttggccgagc gtgatgtcca gctggtgttt ctggagagact acgtggaccg cggggccttc | 300 |
| tcgtgcgaag tgatgctcta tctgctactg ctcaagatcc gattttccga caaagttgtt | 360 |
| ctcctccgtg gcaatcacga gtgcgaatcg atttcatcct tctacggatt cgcaacgag | 420 |
| tgtaagggga agtacggcat tcagcctac taccacttct tgtcctgttt ccaatcgatg | 480 |
| ccagtggctg cgctgctgtc cacgtcgcgt gggcaagttc tgtgtgtgca cggtggcctc | 540 |
| tcaccccgagc tgaaaacaat cgaagacatt caaactatgg accgacggcg ggaaatccct | 600 |
| accacgggc tgttatgcga cctttttatgg tcggacccga agacttcgca cactcgcgat | 660 |
| gtggacgcag aggtggacac tcagccagga tgggagccca atcaggcccg tggatgctcc | 720 |
| tactacttca attcggcggc attgttcgag tttttaggca ccaacaagct gctgtcgatg | 780 |
| cttcgtgcac atgagttcga ggatgaaggc ttcacgtatc acttcaactc gcaggagtat | 840 |
| caagagctgg atactcgagt ggacaagtcc atgcctccac tcattaccgt tttttcggcg | 900 |
| ccgaactact gcgacagcta cggcaacacg gccgcctatt tgctcttccg gaatgaacct | 960 |
| ttctcgtggg aaatccagca aattaactcc gcgggacatc cagccccacc gattgcgagc | 1020 |
| gcagaacgag gatccgacat gtggcgacta ttcaatcaaa cgttgccatt cctcccagca | 1080 |
| agcaaggaat ctttgagga agttttgtgg ttagcagaag acgacgacg tcttacaagt | 1140 |
| gaaatgcacc cacaagctat ccgaaagatg ttggatgacg aagtgaacaa atgggaattg | 1200 |
| gtagaagaaa cgccaacgcg cagctcgggg ccagcgtctc ctcctcgaat ccaccgcaga | 1260 |
| ccttcttttga gtaatctgga cgagacccaa acggacgagc gtccaagtct gcttactccg | 1320 |
| caagagatgg acacaattaa gctgatgttt tcattaatgg acacggatgg cagcttggaa | 1380 |
| ctcagctcga ctaaagtgtc tcagttcatt ctcaatattc tgggtgaaaa aatcagcact | 1440 |

```
gcggacgcgg aggcttattt ggatgctttg gactacgacc gcaacggagt ggtggatttc      1500
gcggatattc tgtcgtgggt tgccgtgatg aaggcgaatc gcaacaagca cgagtcgagc      1560
cgactcctga gttggccaac tgtacagagc ggtgtgcgca tgttgactcg tgggattttt      1620
tccagtaaag tcttgctatg gctcgcattc ggctgcttac tacgcgatat tatcgtccca      1680
aagcagcgaa aagtgatcaa gtcgtcgtcg atccgagtgc tgggctcagc gtcgctagtc      1740
ctgtacatgg tgggcgtatt gtcagggcga gagcgtggct ggctgcggct tttctctctg      1800
caacgcgctg tcggaattat gacgcagcga ttcgtatcaa agtag                      1845
```

<210> SEQ ID NO 21
<211> LENGTH: 1489
<212> TYPE: DNA
<213> ORGANISM: Phytophthora infestans

<400> SEQUENCE: 21

```
atgatgccgc ggggcttacc accacgaggc ccacctggca gtttcccacc tactagtgtt       60
gcggctgtac cccctgcagg cggtgccgct gcagctcgtt tcggcaagct ctctgtgaag      120
gtgttgcgtg cgtttgacct aaaaaagctg gaatgctgg acactgcaga cccgtatgtg       180
aagctcacga tcggcacgca gaacgtacag actaaggtcc aagcaggcgg tggcaagacg      240
cctgagttta atgagacctt cgacttcaat attgcaaccg agaaggagct cgtggtcgaa      300
gtttgggacc aagaaaaagg aggacaagac cggttcatgg cgcaggcgaa ggtggagatc      360
gtgtcgtggc tatcaaaggg tggctttgaa ggtgacgtcg agctacggga tcgcgagaac      420
agccctgccg ggaagctggc gatcgttgcc aagttcacga agcccgaaat tggcgcgaca      480
ggacccgtca aggctccacc catggcccct ccgatactct caggtcctgc agtggctccg      540 ttgccccag gagcgaatgc cgtatctgtt cctggtgcgc tgccattggc accgtccgaa      600
ccgcctcgag acccgaacgg caagttcacc gacaaggaga ttctcgaggc atttaaagcc      660
tttgatctgg atcacaataa ctatgtgggt gctgcggaaa tccgccatgt gctaataaat      720
attggcgagg cgcctacaga cgaagaagta gatgaaatga tcaagatggt tgacaaggat      780
ggcgatggcc aggtgagctt tgccgagttt tacgcgatgg ttacgaaagg gaagcagccc      840
ccacccggat tgggtgtcac tacagctctt ccggagaaag ctgcagctcc tggaggtgca      900
gtttcgggcg ctcaggccat tcagcttcgt aatcagcgca aaatggcgct ggaagagttt      960
gcacgcgata cggtatcaa acccgagagt gtgaagaagg cgtacaagcg attccaagcc     1020
acagataaag atggatcggg ccagatcgac tactcggagt tctgcgaggt gctgcaggtg     1080
gatccatcgc cgcagtgcga aaggtgttc cagttgttcg acaatgacaa gacgggtcgg     1140
atcgacgtcc gggagttcat gattgcgttg tctaatttca cgggtgctga aaggaggag     1200 aaactaaagt tcgcgttcct cgtgtttgat aaagatggta acggtgtgat cacgcgacaa     1260
gaactgatga agatcctgaa ggcgaaccac atggcctcta gcgaatcgga agttgcgcgc     1320
aaggcggaca ctattatgtc caagggggat aaggacggcg acggagttat ctcgttcgac     1380
gagttctcag ttgtgagcaa gaagtttcct aatattttgt tcccagccta cacgctaggt     1440
acggccaaag attagaatac ccgatgaata caatatcctt atctctcgt               1489
```

<210> SEQ ID NO 22
<211> LENGTH: 2862
<212> TYPE: DNA
<213> ORGANISM: Phytophthora infestans

<400> SEQUENCE: 22

```
atggctagca agctcaacgc gttcctggcc gcggtgcctg cgaacgccaa cgtgcccagc        60
ccgcccaaga cagcgccggc cgtgatggcg ttcccgcagc ttgagttcaa ggaagcgccc       120
gagaacgtgg gcgcattcgc ccccaccacg ccgcagccgc ccgtggtgcg tcgtcgccag       180
cgcaaaaata accccagcct caagctggag ctggactcga accaggaaca tgacagacct       240
gaggatgatc gagatatgtc gcgtccttcc cctctaaaga gcttcatggc cgcccaagca       300
gccgccgtta agctgaaggc acagacggag aagcacgata tcccaacacc agacttggcg       360
cgcacaagca gcgggtccga gctggacgcc aagtcggagg cgggacccat gcgcatggcc       420
agcgtacaag gctcgcacca ccgtcgcgtg tccaccgaca caacgctatt taaccggtat       480
ctgcgtcaac aagcagacct ggatattagt cacgacacgg tgcagtattt cgcaaatgtc       540
ccggtcatta ccgccactgc agctgccgtt gatgctctgg aatgcgaaat gagtgtggat       600
aataacgccg acgaggagca cgcgatcatc gtacaggaac ccgaggagat ccttgctgtc       660
ttccgactcg gaggcaccat ccctgtgtcc agtgcgctgg aaattgtacg acgagctacg       720
aacctcatgg cactagagca gaacgtcatc tcgattcgtg cgccgtacac tctagtgggg       780
gatctccacg gccagttcca ggacttgctc gaactcttcc gagtacacgg ctctcctgcc       840
gtggacaacc cgttcttgtt cctaggtgac tatgtggacc gtggcgtgtc ttcgtgcgag       900
ataatcttat tgctcttggc cttcaaagtg gctttcccgg acagtgtcca tttattgcga       960
ggcaatcacg agtgtcggag tttgagtaca ttttacggtt tccgtgccga atgcctcaag      1020
aagtacggac ctgtgctcta taaccgtatg atcaagtgtt tcgagagtat gccactggct      1080
gcacgactcg agacagcgca cggcacgttc ctggctgtac atggcggact gtcgcccgat      1140
attcagttcg tgggggacat taaccggacaa gtgaaccgct ttatggagcc tgaaccaaac      1200
ggagctctgt gcgacttgtt gtggtcagat cctgcgaagg gcgaagctca ggagcaggag      1260
tgggcaccca atgggatgcg tggctgctcg ttcacattta tgaacgcgc ctgtcgcgaa        1320
tttctgaagc gcaacaacct cctggccatt gtacgtgctc atgaactgga agaaaatggt      1380
tataaggagc actttcgaca cgaaggagac cgcacagaag aagacgagga cgggaaactg      1440
gctctacctg cggttgtgac ggtgtttca gctccggagt actgcaacac gaaccacaat        1500
gtcggcgcga cgctgaaaat tccctgggaa agacaaaatg tcgtctgct gcagtatcag        1560
cagcataaac gcagtcaatg ttccgagttt gagttcacgc gagccagcga ggagacggcg      1620
gccaaggcgt ttctggagga gaatttgccg ttcttgccga ttgactttta cgacttggtg      1680
aatgtgtgtc ggcagctgcg gctcactctt gagagagcag cgagtatcac cccagcacct      1740
gcttcagaac ctattcgcaa gctgtcgctt gtgtcgtcgc tgtgtgcgcc agcaactagt      1800
ctggaaacga ggatcgagga ggaagaccca gagcttcccg tgtcgccacc tgcttctgca      1860
ccagcaaatg aagtggagaa ggaagctaca gcaactctga aggcagtggg cgagtcgttg      1920
caggattggg aacttgttga gacgaagagt gtcgaggttg acactaggaa ggtgaagaaa      1980
gacaagaaga aggagaaaaa ggagaaaaaa ctgaaggaga agatcgaaaa gaagaagcaa      2040
aaggacaaga agaagtggga tacgagtcga attgctagcg gttggaagct ctgccctggg      2100
tttgtacgct tctacgaccg ctacttctca agagacagta tgaagaagag cgagccggag      2160
atcacctcag ctcctggcca tctaggcaag cggccgtcgt ggatctcaaa ctacaaaaca      2220
ccttttagac gctcgacttc gaccggcgag gcccccaccg acactgaaac tgtcgacacc      2280
gtcttggact ctaccggtcc tgctcgacgg aagagtatga cggattggat gcccatgccg      2340
```

```
tcgttcgagc aggtggcgca gctgacgaac acgcttcagg gtcacattcc cgtgcagtcg    2400
aacggcgtca atgtattcac gaaggcacag tggcaagctc tgaagttgta cttctcgatc    2460
ctggatctgg atggcaatgg cgttttgatg gaagagagct tcgttgttct cctcgcagag    2520
caagacagcg gtgggttgag ttaaagtgaa gtgaggatgt gaatttgttg ctaatttaaa    2580
ttgttgttgg tgttgtgtgc agatgcatac gcgactgaag acgaactgag tctgttgatg    2640
gaagtcatgg actgcaacgc cgacaatatg atcactgagc aagatttctt gctattcgca    2700
taccgagcct tactgcgatg gaaaaagct ctacatggct ccgactagag tgtgcaggag    2760
cggaatcgaa ctgacgtagc gaagtatgaa caatgccaga ttagaatcca cagtagcgcg    2820
gcatatgccc ataatgaaga acgagaaatc tattagttga aa                      2862

<210> SEQ ID NO 23
<211> LENGTH: 984
<212> TYPE: DNA
<213> ORGANISM: Phytophthora infestans

<400> SEQUENCE: 23
atgtccgcgc cgaccttcca tcgatcattc cgcaatttgc agcttccaag tcaacagtcc      60
aagctccaaa ccgaaacaag agtgatgatc gcaatttcga cagctgagga tttccactct     120
gccgtggccg ctgcgactca gaagccgttg gttgcctgtt tctccgcgcc gtggtgcggc     180
ggttgcaagt tggtggcgcc caaggtggac aagctagccg aggagcttgc cgagaccgtc     240
tcgtttgcca gggtgagtgc tgaggagcac gagacgttat gcgaagaagt ggaagtggac     300
agcttcccgc acttccgcgt gtacagggac ggcaagattg tgggtgacta cacgagctcc     360
aagttcgaca aggtggagtc ctttatccgc ggccatgtgg ctcctaatac tgtgcaggag     420
accgaggaaa cacctgaagg cgaggttacg gaggaaacgg cggagaagga tgctgcgaaa     480
gaggaggaag tgtcagctga ggctgcgacg gaaggctcaa agaagcgcca ggagcgtgaa     540
gaggaggaga cgaatgacga gcaggtggct aagaaggcca gacggaggag ggaggcgtcg     600
acggaggctg agaaggctgc aactacggag ccagctgaga aggttgagga agcggcaacg     660
gaggagaccg agacggctga aaaggattca tcagaagaga agatcgaagc tgctcccgtt     720
gagaagtctg aaacggccgg gaaagacact gctccagtcg atgctgctgc tgcttaaacg     780
acactgctct gctttgcatg atgtctaaat cgacggacat cttctgtggg ctagctgggg     840
gctgattgat ccagctgaaa tcaagatgaa acaataaaaa agaagtatt ttatggcgat      900 tcttttgttt gtgcccgata tcctcgacat gttctgaata catgtacatg tgctctgcct     960
tcttgtcaga acaatgtgga atgc                                            984

<210> SEQ ID NO 24
<211> LENGTH: 501
<212> TYPE: DNA
<213> ORGANISM: Phytophthora infestans

<400> SEQUENCE: 24
caagcagtga agctaaggaa caacaagatc aaacaaacca tacacctatc tacgatgcct      60
gtcgagatca acaccccga agagttcaac gccgctatcg cgagaagaa gctgacggtc      120 gtgcagttct ctgcgccgtg gtgcggcggc tgcaagatgg tggccccaa ggtgaccaaa      180 ctgatggagt cggacttcgc tgacgtcaag ttcctcaagg tgagcgcgga ggagctagag     240
gatttctgcg aggagatcga cgtcgacagc ttcccaacgt tccgcgtgta caaggacggc     300
```

-continued gaagtggcgg cgtcttacgt gagctccaag tttgagaagg tagagcagtt catccgtgag 360
aatgcgaagt aagcgtgacg gcgatttgcg accgtctatc aaagctcgcg catggtgatc 420
tacaggcttg atgacctacg ctaagatggt ggagagcgag tgagtttggt ccccggcatt 480
gcgtatcggc agtggactga a 501

<210> SEQ ID NO 25
<211> LENGTH: 734
<212> TYPE: DNA
<213> ORGANISM: Phytophthora infestans

<400> SEQUENCE: 25
gacaagcagt gaagctaagg aacaacaaga tcaaacaaac catacaccca tctaagatgc 60
ctgtcgagat caacaccccc gaagagttca acgccgctat cggcgagaag aagctgacgg 120
tcgtgcagtt ctctgcgccg tggtgcggcg gctgcaagat ggtggccccc aaggtgacca 180
aactgatgga gtcggacttc gctgacgtca agttcctcaa ggtgagcgcg gaggagctag 240
aggatttctg cgaggagatc gacgtcgaca gcttcccaac gttccgcgtg tacaaggacg 300
gcgaagtggc ggcgtcttac gtgagctcca agtttgagaa ggtagagcag ttcatccgtg 360
agaatgcgaa gtaagcgtga cggcgatttg cgaccgtcta tcaaagctcg cgcatggtga 420
tctacaagct tgatgaccta cgctaagatg gtggagagcg agtgagtttg gtccccggca 480
ttgcgtatcg gcagtggact gaaggatgct actaatatat tgaaatagga aaccatttta 540
acgaagaccc tgagcctcag gctcattctc aaccggaaat atagaccgca tgcggtccca 600
ggaggacaaa tagagtcttc taattggctt acggggtagg tggtcgcatg cgacgaagtt 660
cataaaaaga cgctcatgcg gcaatttgcc cgcatgcgct aaacttgccg cacagtagag 720
tgtaggggtc gagt 734

<210> SEQ ID NO 26
<211> LENGTH: 1448
<212> TYPE: DNA
<213> ORGANISM: Phytophthora infestans

<400> SEQUENCE: 26
ctcgagccca agcgacaatg gcggcggtga ctggcagtgt ggtaagcgtt cagagtgtgg 60
cgcagttcga cgaggcaacg gcgcgcgagt cgacgctatc cgtgagtttc ttctgggccg 120
aatttcacga ggcctgccgt cccaatggac agctggacgt ggtggtgcgc cagctcgcga 180
ctctgcaccc tcgcatccgc ttcctcaagg tggcggccga ggagattccg gagctctcgg 240
agcgttttca gatcgccgta gtgcccactt tcgtcgtcgc acagggtcgc gccgtgctgg 300
acaaactcga gggcgccaat gtggccgaac tggccaagcg cgtggatgtt ctgagcaaga 360
gcgtggccaa gagcagctcc acatccgcgt ccacagccga ggacgccccg aaaccgctgg 420
atgacgcgct cgaataccgt ctcaagaagc tcatcagcgc gtcacccgtc atgctcttca 480
tgaagggcaa tccgacggag cccaagtgcg gctttagtcg acagatggtg gcgctgttga 540
acgaagaaaa gatccaattc ggcacctttg acatcctcaa tgacgacgaa gtgcgtcaag 600
gactcaagca gttttccaac tggcccactt accctcagct ctatgtgaat ggctcgctca 660
ttggcggact ggacatcgtc aaggagatga agtccgaggg atccatcgtc gagcaactag 720
gactcacgaa gaacgtcgag gaggctgaag ctgccttcca agagagtctc cgtgcactcg 780
tcaactccgc tccagtgctg ctcttcatga aaggccatcc gtccgagccc aaatgcggct 840
ttagcaagaa gacagtcaag ctcctacgtg accaccagat tggcttcagt tcgttcgaca 900

-continued

| | |
|---|---|
| tcttgagtga cgagcaggtg cgtcaaggtc ttaagaagtt ctccaactgg cctacgtacc | 960 |
| cgcagctgta cgtcaagggc aaactcgttg gtgggctgga tatcctgaac gagatggcgg | 1020 |
| aggacggcga cctcagtgaa cagcttggcg tggagaagaa ggccaagaag gagaacaaat | 1080 |
| acgaacagct aatcaaccgc gctcgcgtca tgatcttcat caagggaacg ccccagcagc | 1140 |
| cgcagtgtgg cttcagtcgc aagctcgtgg acatcctgga cgccgagggc ttcaagtacg | 1200 |
| actactttga catcctcacg gacgacacgc tgcgtcaggg actgaaggag cactcgaact | 1260 |
| ggcccacgtt cccgcagctt tacgtcaatg gcgagttgat cggcggactg acatcgtgc | 1320 |
| agcagctgca ggaggacgga gaactcgccg agctcaagga gtagacgacc aggtcatcct | 1380 |
| tcgcgtaaaa cgaatacaga aaatcatttc tcttatcctg catgtgtatg ctgggtttga | 1440 |
| tggtttaa | 1448 |

<210> SEQ ID NO 27
<211> LENGTH: 1106
<212> TYPE: DNA
<213> ORGANISM: Phytophthora infestans

<400> SEQUENCE: 27

| | |
|---|---|
| gtcggaagag gtcgtcggtc gtccatgcag ctgcagacgt tggcgtacgc catctccggc | 60 |
| gccttcacgc tgcttttccat tatcctttcg ggatggctca tctggacaca cttgctgtac | 120 |
| aatccgtcag ccggcatccg caagcacgtg atccgcatcc tcatgatggt ccccatttac | 180 |
| gcgctaacgt cctacatggc gctggtattc aacgagtcca aactgttgtt cgagactgtg | 240 |
| cgcgatctgt acgaagcctt cgcgctctat tcgtttcact gcttcctggt cgagtatctg | 300 |
| ggtggccaat ccgttctagc aagcaccatg cgctccaagc cgcagatgac acacgtcttc | 360 |
| cctttctgct gtgtacagcc gtggtccatg ggcggcaagt tcctgcgtca aaccaccatc | 420 |
| ggcatcttgc agtacattcc cattaagctg cttatgagca tcgtcatgct catcacgagc | 480 |
| ttggcaggtg tatacggaga aggagagctc atgaaccccc tagtgagcta cggctacgtg | 540 |
| tgctttatcc tcagtgcgtc gcagacgtgg gcactttact gtctgctgat attcttccac | 600 |
| ggagctcacg aggagttgca gcccatgcgg ccatggccca gttcctggc cattaaggca | 660 |
| attattttct ttacgtactg gcagtcgatc atgattagtg gacttgtaag tgtcggggtc | 720 |
| atctcggaga agtggcatat cggctgtccg gactgctggg acgctcagaa aatcgcctcc | 780 |
| gcactgaatg actttgtcat ctgcgtcgag atgctgggct ttgccattgc caccactac | 840 |
| gccttcgcga ttgaagactt tttgtcgccg tcaggtacgg caggtgttag tgtgccgtct | 900 |
| tcgaacgtca aggcaccact gctggccaat tttatggacg ctatcaacgt gacggacgtg | 960 |
| tcgacagacc tcaagaactc ccggaacgag attctcacca gaaacaggc gctggctgcc | 1020 |
| aagttcgagc gcatgaactc gacttcacct ggtggtggca tgtttttaata gcgtcagtta | 1080 |
| aaagggagcg atacagtaag cacacg | 1106 |

<210> SEQ ID NO 28
<211> LENGTH: 2007
<212> TYPE: DNA
<213> ORGANISM: Phytophthora infestans

<400> SEQUENCE: 28

| | |
|---|---|
| atgagctcac aggacggcgc tggtcgcgca tctgaggaca agaatggaga cggcgtgtac | 60 |
| gtgacgaaga accgctcgct cttctccatg tggctgcacg gcaaggcgat tccaagccgt | 120 |

```
tctggtccgg ccgtggtgtt ccgctcggcc gacgtgatac aggaagggta tttgctcaag      180
cagggcctgc gacttaaaat gtggtcccgc cgctacttta tactgcgact cgaggagcga      240
cacatgactc tagggtatta taccagcaag gactctctga ctttatgctc cgagacgccc      300
atcggaccag acacttgtt gggacacgtc aacacgacca aatacccgcg tcgtctcgag       360
ttgcgctgcg gtacaaaggt catggtactc gaggcggagg accaaaagtc gtatgaagcc      420
tggaagaacg ccctccaaga agcgatacgc tggaaccacg ccatggtgcc ttcaaaagac      480
ggcagttttg tcacgtacgg gaagcaagcg accgaggata taaaacaaga ggaacgcagt      540
cgcgccgagg cggccaagaa gctgcgagag aagcagcgag cggacgaggc cgccgccgcc      600
gccaacgccg ccaataaacc caaatatctg cccgcgacac gccccgggac gcaatgcttt      660
atgacatcga atacaagatt tgagattccc tctcatttcg aatatgtcaa aaccatcggc      720
tcgggcgcct acggagtcgt catctccgct acagctcgc aaacaggcac cacggtggca       780
attaagaaca tccagcgcgc gttcgacgac ctgacgacg ccaagcgcat tgtacgcgag        840
attaagctca tgcgccactt gaaccacaag tgcgtgcttg gggtggagga catttttcgag      900 cccgtggcgc tgtccaagtt cgaagacgtg tacattgtgt cccaattgat ggctacagat      960
ctccaccgcg tcatctactc gagacacgcg ctgtcgacac aacacatcgc cttcttcatg     1020
taccagatgc tgtgtgccat gaagtacgtg cactcggcca acgtgatcca ccgagacctg     1080
aagccgtcca acgtcctggt gaacgccaac tgcgagctca gatctgcga cttcggactg      1140 gcgagaggcg ttttccccga agaagagctg gaattgacag aatacgtagt cacaagatgg     1200
taccgagcgc cggagatcat gctggggtgt atgaagtaca ctcgggaggt ggacgtctgg     1260
tccatgggct gtatcttcgc cgagatgatg tcgcgcaagc ctcttttccc gggacaggac     1320
tacattgatc agctgcatct catcatgaac gcgctggggg ctccaaacga ccaggatctc     1380 tacttttga gcaacgcgcg tgctaggaag ttcatgaacg ccgagttcca gaagcgcgga     1440
cccaacccga cgaagcctct ggcgcacatg ttcgcagatt cgcctccaga cgctctggat     1500
ttactgcaga agatgctggt gattgacccg aataagcgga ttagtgtgga cgaggcgctg     1560
gcccatccgt acttggctgc gatccggaat gtggaggacg agacgaccgc cacttcgagc     1620
ttcgattttg actttgagaa cgagaaattg acgaaacccg tgctgcagag actgatctgg     1680
gacgagatga ggcatttcca ccctgaagtg ggcgacgaga cagcgacgga gggagatgac     1740
agcagtgtcg ctaccacgca ggcttctatc acacccgtga cacctgtgac ccccgctacg     1800
gtagagcaag acacaacaga gacgacaagt gacagctcgg acgcccctgt caaggtatcg     1860
acgccaacag cgtcagagga agccaagcca gaagacgaag acggggaaca acacagcacc     1920
aatagcgaca agatccatag gacagacaaa ctgacagacg cacagacgcg acaagaggcc     1980
ggcgaaccag ctcgggaagt cgcataa                                         2007
```

<210> SEQ ID NO 29
<211> LENGTH: 2053
<212> TYPE: DNA
<213> ORGANISM: Phytophthora infestans

<400> SEQUENCE: 29

```
gctcaagcca gagtccaaac gctcgttcaa cgcccattca acgctcgagc aacggctgat       60
accgacatga accgtaagct ggagctcatg gagctggaca cggcggcgc cagccctaac       120 agcagcaaca gtggaagccc cagtccgact ctcgacctgc tgcatcgctc tgattcgagt      180
agcagtaacc aggggggtga gatgcctctt gtcggggttg cccacaaccc agacgtacgt      240
```

-continued

```
cgtctgcctt tctctatttg tagtgatagt attttcacgt agacgtttgt tacagctgag      300
ttatttgagg gcaactgcaa cacatggagg cagcagcacg accagcagca agtatggcag      360
ccccgaggag tcatttggtg aagaggacga ggacaacaac aagaagacgg cgcgtcgcaa      420
gaccgactcc aacagcaagc gtccgtggac acgcgaggac aatgacaagc tcatgcaact      480
cgtcaagcag tacggcgcca agcgctggtc tctcatcgcc atgcacctgc aggccgtgt      540 cggtaagcaa tgccgtgaga gatggcacaa ccacttgaat ccgtcggtcc gcaaggacgc      600
atggacggct gaagaggact atgtcatctt cgagtgccac aagaatgtgg caaccaatg      660 ggccgagatt tccaagatgt tgcctggcag acggacaat gccatcaaaa accgctacta      720
ctcgaccatg cgtcgcatgc agaggcagtc aatccgcaaa aaggtccca tgcgtgatgg       780 caagagcatc cgcgtggcgt cagtcacgtc gtctcccgtg caaaacaaca accaaatggg      840
tcctgctccc agccagcgat ctttgactgg catgcaacac cagttgccac cgcaacaaca      900
gcttccgcac cgaggggtga gtttccaatc cacatatcaa cggctcttct cggaggcctc      960
tggggacgcc gcacgcgtga gtcccgctgc ttcgaattaa ttggagagga tcgatactaa      1020
ctattatggt gttgatatat aatgcaggat ggcaactcga tagtggactt tgaacgttca      1080
aacatgatgt ccgcatcact acgacaaccc acgatggtct acccgctaaa cggaggtagc      1140
ttttcaaacg ggatgaaccc ggactatagt cgtcccatgt ccatgacgtc gtctccctgc      1200
tcggtgtccc ccgccgatga tctgaatcat aacagccaga acgagacctt tgactacgtt      1260
ccgatgcaat cttcgatcca gcgtgtacgg tcatctagtc cggttgtgat gggcactcct      1320
ccttcgacgt caataggcat gatgaactca ccttacggct cgcctgcaag tcacatccaa      1380
cagcaacagc ctggcaacta catgatggca ggaaacccat attctaacaa caacgtgcgt      1440
gggatgtact ttgggacgtc tgggcttgct cagcaatacc gtcctgatgc ccctgtaaac      1500
gtcccacaca agcgcctcct cgacgtccag ggttcacaac gtgatatgtg aagaatgat       1560 agccctgtat cggtagcagc accgatattc cgcggtatgc cggcgacgca catgcagcaa      1620
ggtcaagtca gcgaaccgat ggcattgcag cagtccaagc cagcttccat gccactgtat      1680
aggcaagcgc cgaatatggg tcacttcaac agcatggagc aggtatggac ggatgatgca      1740
tatctgtgat tggaccgcca ttgtggcatg ctcctgatag actgcatgaa acaaatttaa      1800
agttattact taccaaagac agtggcttct cttactcttt acttggttaa cttttttcgc      1860
ttgatctaca gcggtttcac gttaggtagc tgtagctcct gatcgagttg cttattaaat      1920
agcaccactt gttgacaggg attgatatta aaatgaattt ttttcagact aatatattag      1980
ctgatattac atgtaccaaa atgtcaaact aatagctgac tattagtttg aaaaaggcgc      2040
caaaacaagc taa                                                        2053
```

<210> SEQ ID NO 30
<211> LENGTH: 1173
<212> TYPE: DNA
<213> ORGANISM: Phytophthora infestans

<400> SEQUENCE: 30

```
atgcttggcg acgtagacag tttcggcggt ctgggtccca ttccgtccat gaacgcggtg       60
ttggagaagc gcacgtcaag tcagtttttcc attagctcgc tgctgccccc gtccgtgagt     120
gtctcgagta ctggtgtgtt aaacacaact gttacacgga gcgagagcgc agtgacagat      180
agtgttgaag caactaccga taatgaaggc caaggatctg caccaagggt gtctaccaca      240
```

| | | |
|---|---|---|
| actgcagagg ggtctggtgg caacaccaag tacatggacc ccactacggg cgactacatg | 300 | |
| tacccggaca acgtcaagcc catgagcttc tacgacaaac aacgtcttgt gcagaagatt | 360 | |
| acgatgcttc ccagtcaata tctgcgtggc ctcatggacg tcatcagcaa gtaccagcca | 420 | |
| gatactgtac gtcagatcga cgacgatggc tacgcgttcg atctgggtca gatgaacgag | 480 | |
| aatactgtgt gggctatcag tgactacgta aaggactcga tgattgagct ggatggatac | 540 | |
| attaaatcac tcaaccaaac tgctattgac cttgctgccg gtgaggatcg acatggagaa | 600 | |
| actgttctga cggccgcaag tgcggctaca cccaccagca gtgcggttcg ccacttgacc | 660 | |
| gacactctgg cgatgaacac gtccaagatg tctgtcatca ctaataacga gaatcagaat | 720 | |
| aaattcctgg aacaggtgga gatgtattcc aaacccaaag tgaccaagtc gcgtgtaaag | 780 | |
| cccagcaaga agcaccagtg tccgacgtgt aacaagcaat tccgcggacg ctccgagctg | 840 | |
| cagaaccata tcagaactca cacaggcgag aagccactca aatgctcgta cgcgggatgc | 900 | |
| acgaagcgat atgcacacag ctcgaatctg cgtgcacacg agcgaacaca cgccggaata | 960 | |
| aagccgtata catgtcacta cgacggctgc gggaagagct tcgcccactc tgtatcactt | 1020 | |
| aaggaacata tttggatgca tgcaggattc cagccctacg tgtgtccgta cgagggatgc | 1080 | |
| cagaagaagt ttacgcaggt ctcaaatttt gcccgcacac agaagacgca cgagaaggaa | 1140 | |
| gacaacgaac actcgattga gagcgataat tag | 1173 | |

<210> SEQ ID NO 31
<211> LENGTH: 754
<212> TYPE: DNA
<213> ORGANISM: Phytophthora infestans

<400> SEQUENCE: 31

| | | |
|---|---|---|
| atgattaagc tcgcggccgg tgtgtccaag aaatccgtcg tcgatgtgta tgtcactctc | 60 | |
| agtgtgcccg acagccccgt acttagcacg gcacagaaga acgtggagct gaacgtcgag | 120 | |
| aagttcttcg tggtcagcaa gactctgcct gaattgcctt ccaggtagaa gacgctgccc | 180 | |
| gccccgacgc cttcgtcaag gcaacggatc ctcctacgtg aacgtcggtc tggaggatcg | 240 | |
| tctcaactcc cgtccgcttg acctgcatac acctgccaac cagtgtatca agcgcatcca | 300 | |
| ggccgctgtg ggccagctgt tccgtgcatt cctcatccag cgcgacttcg tggagaccca | 360 | |
| cacacccaag ctggtcgctg gcgcctcggg gagcggagcc aactgcttca cactcaagta | 420 | |
| cttcgattag gacgtcatct tggctcagag tccgcagaag tacaagcaga tggcgtgtgc | 480 | |
| tgctgctggt ctcgagcgcg tgttcgagat cggcccggtc ttctgtgctg agaactcgag | 540 | |
| cacgcaccgt cacatgtgcg agttcgtggg tctggatctg gagatgacta ttaaggagca | 600 | |
| ctaccacgag gtcctggagg tgttctcgga cctgtacatc tacatttttcg atggcttgaa | 660 | |
| ggaacgttac gccaacgaat tggctactat caacaatcag tacccgttcg agccgctcaa | 720 | |
| gtacattaag ccgtcgctta tcatcaactt ctag | 754 | |

<210> SEQ ID NO 32
<211> LENGTH: 659
<212> TYPE: DNA
<213> ORGANISM: Phytophthora infestans

<400> SEQUENCE: 32

| | | |
|---|---|---|
| gggctccatg tcatctgcga ctttggacgg agctctctat tgtagaattc aactgactct | 60 | |
| agacaagtaa ccatgcagaa cgaggccggc cagtcgatcg acatctacat cccgcgcaag | 120 | |
| tggtgcgtat tgcgctggtg actttaatac gctcagagct actggagcta actggtgctt | 180 | | gctattgtct gtcatcgtta tatagctcgt ggaccaaccg catcctggcg gccaaggacc 240 acgcctcggt gcagatcaac gtcggccgcg tgaacgccaa cggcgtcttc acgggtgagt 300 cggacacctt cgctcttgct ggctacattc gccaccacgg tgagggcgac atggccatca 360 ccgagctggc tcgccaggcg gacgccaaga actaagcaga ccaagttgtc gtgatcgcgc 420 gctgctgctg cgaagtggag tgtgcgttca tctacgtcta gctggcagtt caggaggctg 480 gtgattacga tatgtatcaa cagatacgtc tgtgatcgct ggcaggaatt gcggtaccgt 540 cgcttatgga gtcggttgtt tgcgggttcg acctcgcctt ttgatttgat cgggtgtagg 600 cttagtattt aactctggcc aacggacgag caagaataaa gtagttcaaa cccgtcaga 659

<210> SEQ ID NO 33
<211> LENGTH: 1049
<212> TYPE: DNA
<213> ORGANISM: Phytophthora infestans

<400> SEQUENCE: 33
ctcgagcgca agacgatctc cgctatcgcc ccaccatgtt cgccagcttc gccactgccc 60
tcatcgcttc cactctccgg ccctcgagcg cagccgccac caactatgcc ggtggctggc 120
ttccgtcgga ccccaccaac cagtgtgtgg atatttgctc cgctccgtcc aagacgtgcc 180
tcacttcgga cgctgcctgc ctcgccaagt cgatggtccc gggcgacttc gactatatgg 240
tcctggagca gctcttcgtg ccgcagttct gccgtgacct gctaaagggt gtcgactcca 300
ctatttcgca ccaaaacatc gatatgtacc cgaacggcac agcctgcgtg gagagtgtgg 360
tcaagagtga gctcacgatt cacggtctgt ggcccaatta caacgatggc tacgtgagct 420
gctgcaatcc gagctcagcg gtggccaacg acccttataa cgccgctgac ttcgctgccg 480
cccaaagcag cctactcacc accatgggtg agaagtgggt ggacgctacg caagccacta 540
cgtacgaatc gctatgcgag atctacaacc acgagttcca gaagcacggt ctctgctatg 600
ccgctgacga cgctgattac atctcggctg ctgtcacgta cttcactgct acgctgagca 660
cggcggaccg catcagttca gccaccgagc agatcaacaa gtgggcagct cagtcgacgc 720
ctcagacgac tctggccgag attgaggctc tctacggcca cagtgtcatg gtgttgtgct 780
cggctgtgga tggcaacaac caactgtcgg ctatccgtac gtgctacgag aagccgacaa 840
acatcacgag cgagggagcg tccgcgcaga ttgactgcgc agccgcgacg gccacctcct 900
cgttctccgt atgctccggt gactcgccga tcactctgac tgcatacaca gcccccacct 960
cggcttcgat gcaataagct ccgacgatag agcgacggtg cagtctgcta gtataaagtt 1020
caatgcacca gttacttaaa aatgtacca 1049

<210> SEQ ID NO 34
<211> LENGTH: 1203
<212> TYPE: DNA
<213> ORGANISM: Phytophthora infestans

<400> SEQUENCE: 34
atgaccaagt gggggttgt agtggcacta acactgctgt tagcgacgcc tagtttagtg 60
ctaggcgcct gccccaacaa gtgttccgga cacggcaaat gcggtctcaa tgacgtctgc 120
caatgcatgc agaactgggt cggcggtgat tgctcgggtc ggcaatgtgc gttcactcgc 180
gcgtggcaag atacagcaca gcgcgacgac gacgcacact accacgcaga atgtggcagc 240
cgcggaacgt gtgatcgagc tactggagaa tgcacatgtg acgcaggatt catcggcagc 300

-continued

```
ggctgtcgac gaatgcagtg tcccaatgac tgcagtggcc acggcacgtg tgagtttatt    360
gaggaattgg cgacggatac ggcccacaag cggattgggg gagtggcagg tcgtaaatac    420
acgctttggg accaagagaa gatcatgggc tgcgtatgtg acgccaacta cgaaggtcac    480
gattgctcga tgcgctcgtg tcctagaggc gacgatcctc tgaccccgaa tcaatacgac    540
atggtgcaag ctattattct tgataaggct ggcggtgagg ggtacttgac gtactatgat    600
ccgtacggca atgcgtatac tacggagaaa atcacgcttg gtggaacgct gagtgtcgct    660
tttcaaccaa cagacgatga taccacatgt gcaaacattc agaaggcgct ccgccgttta    720
ccgaacaacg tgctcaacac agtcactgtg gtagctgttg acaggtttta tgccttcaag    780
cgctctgacc caacggactc gttggggtat ggaacgttaa acaaaattgt aaatgacgac    840
gctgcagcgt acgcaggaac cggaactcaa attaaagcga tgtgcgaggt gatttttacg    900
tcggagccgg gcactacggg gtatcagaat ttgctggatt gcaatgttgc cgcgcatggc    960
gatactaagg gccagcaccc gcttactact ggtgtaacgt ctggcacttg cgtcgttaaa   1020
gaagtctatc cggtgacgct tggcacgagc aacatgcttg ccgaagatac tccagcgtat   1080
cgtccattga ccgagctcac cgagtgtgct ggtcgcggca cctgcgacta cgacacagga   1140
acatgcgagt gcttcgcggg ccacatgggc ttggcatgcc agaagcagga agcgctcgtc   1200
tag                                                                 1203
```

<210> SEQ ID NO 35
<211> LENGTH: 7947
<212> TYPE: DNA
<213> ORGANISM: Phytophthora infestans

<400> SEQUENCE: 35

```
atggcgcgcg ctccggcaca attggcgcag cttttactag cggcgctgct gctgtcagcg     60
atgtgtgagg cgttattgcc tatcacgaac gcgctgcagc gtgcccgcca aaacctcacg    120
gccttgcagc ggcaatggat cgatccggac acggacccca agttctacaa catatcagtc    180
cccaagggtg ccttcaactt cggtggcaac tcgagctaca acaacgagta caagctcatc    240
ttctcggacg agtttaatag ctccaagcgc acgttcgagt cgggtttcga ctccaaatgg    300
acggcagtca acctccgcga taccaccaac atggggcagc actacttttt gccccaggct    360
gtgcagatcg acaagggcaa cctcatcatc acgacctcca agcccaaaca gcgctaccgt    420
ggcactaagt acgtcagcgg tgctgtgcag acatggaaca agttctgtta caccggcggc    480
tacgtcgagg taagggccat tctgcccggc aagtggggta tccccggcac gtggcctgct    540
atctggatca tgggcaatat cggccgtgcg ccattcctcg gatcccagga cggtacgtgg    600
ccgtggagct tcgactattg cgccccctac gtggagaagg ccgagaaggt caagcagaag    660
atcaatgcct gtggcaatct gaccaacaaa cacgacaagg aatcgtatcc agagatgtac    720
ggcttgaacc cctttcaggg tcgtggagcc acggaaatcg atgtgattga agcgcagatt    780
cgtgctcgtg atgagcctgc attcatctcc acgtccctgc agatccgtcc cagtctgtac    840
gatgatatgc gcccggcttc agagtcgctc cctgctcctg gacaatggta ccagggtctc    900
aagtttggtg agttcacgaa aatcaatagc gactactacg gtgagatggg cctcgactcc    960
atttcggctc tgacacagct cgagtccaat gcgttcaagt cgttccactt gttccgcctg   1020
gactggtctc ctggtcccga aggttacatt cgatggtgga tggacaacag cttcgtgttc   1080
gaaatccctg gatccgcgct gaataagtgg gtaggtgctg tccccccctcg ccagatcccc   1140 gtggagccta gttatctcat tctgagtacg gctgtttcgg agaagttctc tccaccgtgc   1200
```

```
gatgggcaga tttgtaactc gctatggccc tccaacttta cgatcgacta cgtacgcgtc   1260
tatcaaggca acccgaaccg gtatacttcg gtgggatgca atccggaagc ctacccgacg   1320
aaagattgga tctacgccca cccagtggaa tacggtctcc cgtggtatgt ttcactacgt   1380
gtggacatcg gtctgctgca tcttttcgct gtggttaatg cgctgctggg tctcttcatg   1440
gcgttccgtg gcacgtccca accgaagatg ttgtcagcgt acgccagctc gttgtggctg   1500
actgcagcct tttatggagc tcttagttca agcgcccccg tagaccttgc ttggattcag   1560
actgcgcttg cgtgtctgtg cgggctggta cttggcggtc tttgttgctt ggtgtacccg   1620
gtttcgcttg gtgcaatgct tggactgtat ggcggggtga tagctagcca attcgtgcct   1680
ttgctgtcta cgcgcgtgat cactgcatta ctggttggtg tgggaatcgc gctaggatct   1740
gctccacaga tcgacacgaa gcacgttgtg attctgtcga cctctttgct tggtagtttg   1800
gcgtttctgc tctctgtatc gctgtgggtg agtgaaggcg atattgctga gaatgcgtgg   1860
aatctcgctg gcttcatttt caatggtaac aacgatgacc acgtgggttt ctgcacgaaa   1920
tattgcctgg cgatgtatat tctgcttgtc gtactcagtg cggtgagcac tacgtatgga   1980
tacctccgta tgcgtggcgt gacgctgcgc accaacccgc gtgaggccaa gttccccgcg   2040
gtgtcagcaa gttctgacgc gcgggcttgg agacctgatg atgatgcggg cgtggagaag   2100
actacggtga attttttctc gccatccaag ctgccgtaca acatgcagca gttcagtacc   2160
atcttccgta tcgctgtgaa cgtgcagcgc tcgtttggct ccaacttga caacttccgc   2220 aaccagacgg aacacgttgt ggtgcttctc accaacaact cgcgaaagag cggaaatcct   2280
taccgcaagc tgcacgattt ggtgttttcc aactacaaca actggtgctg caagcttaag   2340
atccagcctc tgaactgggg cgagcagcga ccaccgcagg gtggtctcac aatggtggac   2400
gagatgtcgg tggacttgtg tctgttcttc tttatctggg gtgaggccag caacctgcgt   2460
cactcgcctg agttcctgtg tttcctgttt cacaagatga agaagagtt cccgtccgtc   2520 cgtcactcag agcgcgaggc tggatacttt ttggatacgg tggtgacacc tgtctacggc   2580
ttgctgaagg ctgagatgac ttcaaagtac gaccatgagg accgtcacaa ctacgacgac   2640
ttcaacgagt tcttctggac gaagagatgt ctgaagtatg actacaaaca cgaagaggtc   2700
attgatttgg cgtcacccaa tccggctatg atctacaaac agaagcagca gcaacgtcaa   2760
ggtctgactg gccttggagc ccaaaaggct cgaggtggac tcaacggtgg ctcgaacggc   2820
tccaacttgt tcaacaagcg tcaaagtatt gccgagggat tcaccgagtc tgccaagacg   2880
ttcgttgaga agcgtacgtg gctgctaccg ctgcgcgctt tcaaccgtat cttcaacttc   2940
cacgtcatcg cgttccactt cttggcaatg ctcgcgttcg cgaatgagca agagatggac   3000
ttccaggacg cctgcaagat tatctcgagc actttgatat ctcacttctt gctggacatt   3060
ttacgtgatg gactcgacat tttcgctgtt tacgacgagc accggaaagt attctcaatg   3120
gcgcgttccg tgatgcgtgt gtttctgcat ctggctcttg tggtggtcac gtcgatgtta   3180
tactggtatg cgtgggcgta cggtggtgcc tggtggcagt cgtactacgt gaccgcggtg   3240
ctattccacg tgccaggcct gattaactgc gtcatgcaag tgatgcctgg tcttaccaac   3300
tggacacggc gcacggcgtt tgctcctgtt gcatttatcc gtgacattgt gagtccgatg   3360
aaccgcttat acgtgggtga caacgtgctg gatccggagt cgatgagcgt aggctaccag   3420
ttcttctgga tgtcgctatt ggcttggaag ttatacttcg gctacgagtt tgagatctac   3480
ccgcttgtgg tgccgagctt tctgctgtat gctgaccacg tggagaacaa cgtgagcatg   3540
```

```
attacgacag tgttcctcat cttcctaaac tggatgccgt tcttcttggt gttctgcgtt    3600
gacattacga tttggaactc gatctggatg gcattcacgg gtacgttcgt tggcttttcg    3660
tcgcgcattg gtgagattcg caacttcacc cgcgttcgat ctgcgttcag tcgtgctgtg    3720
gatgcattta acgcaaaggt gattgcgcga agctccaaga cgggacttca actctcggac    3780
agcaatggca cgtcgtatgg atcgacatca gtaggtcacg aggtgcttga tcgtgttgcc    3840
ggtggtgcgg atccgacgtc ccgcctcctg ttgcagcgcc ggacatcagc ccatgacgac    3900
gagactccgt tactgtcttt ctcgcgtcgc aaacagacgc ctacggagcg ccaagctgct    3960
cgtcgccgca agtggttctc gttctctgtg gcctgggaca ctatcatcga tagcatgcgc    4020
gcggatgatt tgatctcaaa caaggagaaa tctctgcttc atttccaccg tcttgacggc    4080
taccagcgcg aaatttacct gccgcagttc caacttgctg gttgcttcga aactttacg     4140 tcgcacattc ttgatattta ctcgtcgaac aacggcaagg tctcggagcg tgtgctgcaa    4200
gacaaactac tggaaattct cagtgataac ccaatggtgg aggagtcact tgaagagata    4260
tgggagcttg cgaactgggt gctggttaat gtgcttggtc cctgtcacgc gaatgatgtg    4320
aagtacatca catgtgtgct caactcgtgg gccgctcgtg gtgtgttccg tgcgctgaac    4380
ttgcaaaagg tggctccatg tggccgcgct ttggcgggtt tgatctcgct cttgaaggcc    4440
aacgtccgag gatggaagag caacgccaag gttatccctg ttcgcaaaga cccatccgac    4500
tacgcttcgt acgagtttcc gcaacagtct agctcctacc gtccttcgtc ggggcttact    4560
aagtctgcaa gtacgacagg tctgtcgtcg ttgggtctcg aaccacctcg tcgtagtcgt    4620
ggctctggtg ttgcgcgtat tgcacgtatg cagcagcaga cgcacaaacc agctgtcaac    4680
aatggcaagc ttactcattc tatctccagc tctcacatca tgcagattcg cgagcgcgtg    4740
cgtacgttcc tgaatcttgg aaaggagatt ctggcccacg tccacgagca agaccccgtg    4800
ttcgctgaaa gcaagggaat tcggatcgg ttgacgtgga ttcttacaca ggagcgtggt    4860
tttatgtggg acgataatta tacgggtgaa caaatcactc tcacagcgtt tgagagccac    4920
accgatgtgg tgttatcgca tctgcacgga cttttgacct tgcagaagat tgatgcggag    4980
ccccagtcgt acgatgctcg tcgccgcttg ctgttcttcg tgaattcgct gttcatggac    5040
atgccgcttg ctccgctgct cgaggaaatg aagtcgtgga gcgtcatcac tccgttctat    5100
gccgaagacg ttctgtactc cagaaaggat ttggaaagca acaggacgg tctgacgtg      5160 cacacgctgt tgttcttgca gacgctgtac aagcgagact gggagaactt cttggagcgt    5220
gtgaagccta agaagaacat ctggaaagac ccggagactg cgatcgagtt gcgtatgtgg    5280
gcttctctgc gtggccagac actgtcacgt acggtgcagg gtatgatgta cggtgaagct    5340
gccattcgtt tgctggctga gatcgaacaa gttccccaac agaaacttga ggagttgatc    5400
aacacaaagt tcacgtacgt ggtggcctgc caaatttatg gacgtcagaa gaagaacaac    5460
gacccgaagg cgagtgacat tgagtttttg ctgcaccgat tccctaactt gcgcgtggca    5520
tacatcgatg aggtccgtgt gaactaccaa aaggaacagt catacttctc ggtgctcatc    5580
aagggcggcg aggaactcgg ctcagttcac gagatctacc gcgtgcgtct gcctggcaat    5640
cctatcttgg gcgagggcaa acctgagaac cagaacgcag ccattgtttt cactcgcggt    5700
gaaaatctgc aggctatcga tatgaaccag gatggatatc ttgaagagaa cttgaagatg    5760
cgaaacctac tcgaagagtt tgacaagggg acgcagacc ggccgtacac gatcgtgggt     5820
atcccggagc acatattcac gggtagtgtg agctcgctgg caaactacat ggcgctgcag    5880
gagacgtcgt ttgtgacgct aagtcaacgt acgttggcgc gtccgctgcg tagccgtctg    5940
```

```
cactacggtc atcccgatgt gttcaacaaa cttttcttca taacgcgtgg cggtattagc    6000
aaggccagta agggtatcaa cctcagtgaa gatatctttg ctggctacaa caattgtatg    6060
cgtggcggtt ccgtgacttt cccggagtac accaagtgcg gcaagggacg tgatgtggga    6120
atgcagcaga tctacaagtt cgaggcaaag ttagcgcagg gtgcagctga gcaatcgcta    6180
tcgcgtgacg tgtaccgtat tagccagcgt ctcgactttt tcaagttgtt gtcgttctac    6240
tacaaccatg tgggcttcta cctggcgatg tcaatcatca tctggactgt gtactttctg    6300
ctgtactgca acttattgcg tgcactgctg tcggttgagg gtgttggcgg tcgtgaaccg    6360
gtattgctaa gtaagctgca gttgatgctt ggatcggtgg cattcttcac tactgcgcca    6420
ctgctggcga cgatttcagt cgagcgtggc tttaaggcgg cgttgaacga gatcattgtc    6480
ctgttcgtga ctggaggccc gctgtacttc cttttccaca ttggcacgaa atggttctac    6540
ttcggacaga cgattcttgc tggtggcgcc aagtatcgtg cgaccggccg tggattcgtg    6600
acaaagcact cttcttttga tgagctttat cgtttctacg ctagcagcca cctctatgct    6660
gcagtggaga ttgccattgg gctttccgtt tactacaagt tcacggtcgg caatcagtac    6720
ttcgcgctga catggtcgct atggcttgtg ttcgtgtcat ggtactggtc gccgttctgg    6780
ttcaacccac tggcgttcga atggtctgac gttatggagg acttccgtct atggttcaaa    6840 tgatgcgtg gtgacggtgg taaccctgat caatcgtggg aggcgtggtt caaagaggag    6900
aacgcgtact tttcgacgct tcgaccgtgg tccaaggcgt gcattacgat caagggcgtg    6960
ctgttcgcgt tgatcgccgt ctctatctct tcgacgagtg acaaatatca ctcgatcttg    7020
acggaaacca cgtggcttcc gctgcttatc tgcttatcga tggccgcggt gtatcttagt    7080
gcagaggctg tcttcttcac ctcgtcgcgt tcgggcgaga ccgggcttgt tcgcttcctg    7140
aagctccttc tggtgattgt gctgggcgct ggtctgattc tcgctttcat ctacgcggac    7200
ggtatgtggc agatgctgct gagtatggga tatctcgctg cagctatggg ctgttgggcg    7260
cttgtgatcc ttggtagcaa ctcgcgcttt gttggaacgc tttacttcgt tcatgacgcc    7320
gtgctgggtt tggtttcgct gagtctcatt ctgttgctct cggcgctcta cgttccgggc    7380
aagatccaga catggctact gtacaataat gctttgagtc gtggcgtggt gattgaagat    7440
attctgcgag ccaactcgag caatgatgaa cgcgatgatg atctgtcagt gcagcagatg    7500
cgctccatca tccttgagca gcagcgtttc atcaacgctc tgactgctag cggcagcgag    7560
actgacatcc gcggtgctgg tcctgggaag aaagaagatc taatgcacgc tatgagcgac    7620
aacacgctga acgcggtact gaggaatatg tcggagtcgg aactcagtgc gctgcaggac    7680
tcgtcgattc gtctgcaggc catcatgtcg gaggaggagc gcaaggccgc acaacgcaag    7740
cagcaacaag aagagcagag actcaccgag gcaggaatga actcgtcgtt gtcgcgcacg    7800
cgtcgtgcct tctccacgag cgatttctcc gccatcccgc tgaatgctag cccctacagt    7860
cttgctccta ctcaggatgg ttccgctgca cccgtcaacc gccccactaa cggttctgct    7920
gctcacggag cttatcctga tgtgtag                                         7947
```

<210> SEQ ID NO 36
<211> LENGTH: 6744
<212> TYPE: DNA
<213> ORGANISM: Phytophthora infestans

<400> SEQUENCE: 36

```
atggccacga cgcccggcgg caagatggac cggcgccgcg ccggctccaa ctacttccag     60
```

```
ctcgatgcgg accgcaagcg caacacgtcc aacaaccgca gcaactacgg cgacggccgt    120
ggcaccttcg gagaccgctt gagcttgatg gaggtgcttc ctcccaacac acagggcggc    180
aaccagatgc gcggcggtgg cttacagggc gactttgcgg acgaagtgtc gatcgatttt    240
tgctgcgagg tactgtacaa caagttcggc ttccagtcag gcagtgtgga caaccagcgc    300
gagcacgtgc tgctgctatt ggccaattcc aaggcgcgtg ccaagcccca ggaccctccg    360
ggacaccacg tcgtcacgct gcacaaaaag ctcatgagca actacacgga atggtgccag    420
ttcatcggcg ttcccagcat ctcgtactcg ggacagccac agggagacct caagaaccct    480
ctgcacatgg acattatgct cttcctgttg ctatggggag aggctggtaa cttgaggcat    540
atgcctgagt gcctctgcta cttgtaccac cagtcgctaa acttgctgaa ccaggacttc    600
ctcggtcagc agaaagtacc tgaaggttgg tacttaaggc aggtggtgcg ccccatctgg    660
aaggaggcgt ctaacatgca gaggaagaac agcttgggca gaacttgga gcacacccaa     720 gtgcgcaact acgacgatat caacgagtat ttctggaaaa aatactgtct taacgtggat    780
gtcacgcaga tcggcgagga gctgaccaag aagcacacca agacatacta cgagcaccgc    840
agtatcttca cgctcgtact gaactactac cgtattttc agttcaacat gatgttcatg     900
atggtcctga tggcgatcgg ctttatctcg gccatctcgc ctagcggagg acagcagtgg    960
ttcgctcagt tcgggtctat gggagaagtg gttgagcctt accagaaaca ggacgttaag    1020
ctgacctacg tggggattgt gttcgccctc tcctcgatgg gattctgcaa gaccgtcctc    1080
gaagcgtgtc acggatggca cttactcact gccagtgagt cgtcacagac gtcgtctcgt    1140
tcgttcaact acgtggtgc ccttgtggtt cgaatgctct ggaatggcgc gttcgctggc     1200
attttcggct tgatgatcta caccccgttg atcacgagca agaacacaga actgctcgat    1260
aaggctgcac cggcgtctgt tgcctacatc ctgcctggcg cacttattat cgtcgtgcag    1320
gcctttgctc catcggttgt aaccaaatcg tttgcggcca gtttatccg tgagggagaa     1380 acgtgctacg ttggccgcaa catggcgcct ccactgagct accagctcaa gtacatcact    1440
ttctggatca ttctgtgggc gctgaaggcg ttcgtctcat acttcattct agttcgccca    1500
ttggttctcc cgtcgctggc catttacgag atggagctcg agtacggtag caatgttgtt    1560
tcgttccaca acttcggagt catcgctgcg ctgtggctgc ctgtgatctt catcttcaac    1620
tacgataccc agatttactt taccgtgttc caggctacac ttggtggcgt tcagggtctc    1680
atcatgaaga ctggcgagat tcacggcatc aaggagatta ccaaggcttt ccgtgtggct    1740
ccacaactct ttgaccagaa ggttgtgacc aatctggctc gctcgaacga cgctgcggct    1800
gacggatctg ctgctgcata ccagtcgcaa atgatgctgc gcttcgtggt cgtctggaac    1860
gagattgtca actcgttccg cgaaggtgac ctggtggacg acaaggaggc tgccatcctg    1920
cagtatgaca tccagagctc gggcgacgtg ttcgaacctg tgttcctttc ggcgggtaaa    1980
ctgatggaag ctctggacta cacggttaag attgccaagg aaggtaaggg cgactcgcag    2040
cttcaagtgt acatggtgca gaaggattgt ctatcggctg tgcgcagctt cttcacagcc    2100
agcatgtacg tgatggaggc tctgctgggc agtgacgatg cagacattct tgatgcgctg    2160
cgtcaaatgg aggcgattgc tgcgaacagc agtttcatga gcacgtttga cgccaagagt    2220
ctagtgcagc tgcgcacagt ctcgatggag ttcctggaag ctgtgatgga tctgcccgac    2280
ccggatgcgc agtcctcgca catgacatcg tctcgagtgc acaccatggg agttgtgcgt    2340
aacttcgtga ccaagatgga aaacctgctc aacgctattc gcattttcgc caaccgcccg    2400
gagctcgctg ccaagttcag caactctaag ttctgctcga gcgccaacgg ctacgtgttt    2460
```

```
gctgctcgtg gcctcgtgaa cctgttccac aacgacactg cgatgggtgc tgctacccgt    2520
gcgtacctct tgatgtcgct cgagaaggcc gatgctatgc cccgtgtgcc tgaggctcaa    2580
cgtcgtcttg gttttttcat gaagtctctt ttgatggaca tcccgcagtt gacgtctgtg    2640
aaggagatgc actcgttctc cgtcgtgacg ccgttctaca gtgaaagtgt gttgatctca    2700
ttgtcggagc tgaacgatcc gctggccaac cacccggtct tccagaaggt ggaggagaag    2760
ggcaagaaca ttactattct gaagtatctg attaccatcc accccgagga gtgggagaac    2820
tttttggaac gtattgatgt gagcactgca gaggaagcac aagccaacta cccgctggaa    2880
atccgtctgt gggcgtcgta ccgtggtcaa accctggcac gtactgttca aggtatgatg    2940
ctgtacgagg atgctatcaa gattcttcac tggcttgaga ttggttcaag tcccggcaag    3000
tcggcggagc agaagcaggc tcaacttgag gacatggtgc gtctgaagtt ctcgtacatt    3060
tgtgcgtgtc aggtgtacgg taagcatcgc gcagagggca aggcccaggc cgatgatatc    3120
gactatctgc tcaagacgta cccgaacctg cgtgttgcct acgtcgacac catcgtgatg    3180
gacggtggca agcagttcga cacggtgttg atcaagagtg aaggcaatga aattgccgaa    3240
gtttaccgct acgagctgcc tggagacccg attcttggtg aaggtaagcc cgagaaccag    3300
aacaacgcgc ttccattcac gcgtggcgaa tacctccaga cgattgatat gaaccagcag    3360
cactacttcg aggagtgtct gaagatgccg cagcttctgg tgactgctga cctgcaccct    3420
tccaagaaac ctgtgtccat tattggtatg cgtgagcaca ttttcacggg taacgcttca    3480
tcgctgtcaa agtttaagtc gtggcaggag ctggtgttcg tgacgctgtc tcagcgtgtg    3540
ctggccgacc cgctgtatgt tcgtatgcac tacggtcacc ccgatatttt cgacaagatc    3600
attgctatgc ctcgtggtgg agtgtccaag gcttccaagg gcattaactt gtctgaggat    3660
gtgttcgctg gttttaactc gacgcttcgt ggtggtgtgg tgacgcacgt ggagttcatg    3720
cagtgtggta agggtcgtga tgtggctctg tcgcagattt ccatgttcga gggtaagctg    3780
gctaacggtg ctggcgagac gtctctcgct cgtgaggctc atcgtatggg ccagttcatg    3840
gacttcttcc gtctgaactc catgtactac tcgcacacgg gtttctactt cgccacgtgg    3900
atgacaattg tcacgacctt cgtgtacatg tactgcaagg tgtacttggc tctagcgggt    3960
gtgcagcagc agattgtgta cgatatgaac acgaccgctg tgatcaccga gaacatcgca    4020
aacaacttcg acgggcgtgt gttcaccgat ctgaaggctg tgctgaacac gcagttctac    4080
atccaagccg gtactttcct catgcttccg ctcatgtgtg tgtacttcgg tgaaggaggc    4140
ttcgtgcgcg gtatgactcg attcatcgac atgatcatca cgctgggccc tgccttcttc    4200
gtgttccagg tcggtacgac gatgcactac ttcgacaaca acatcgtgca cggtggcgcc    4260
aagtatcagg ctacaggtcg tggcttcaag atttcccgtg agacgctggt gctgctgtac    4320
aaggcgtatg caagctccca ctatcgaaag gcctgggagc tcatcgggtt gtgtcttgtg    4380
tacatggcgt tcggtaattt ttacatctgt cggaccgatg cggctgccaa cgacaacact    4440
tttgcgtccg actactgtga gactgctcag gcttacgggg tgcagacgtt ctcggtgtgg    4500
ttcatctcca tcttgtgggt ggtgggtccg ttcctcttca acagtgacgg tctggactac    4560
aggaaaacca aggtggatat ccagcagtgg tgcatgtgga tgtttgcccc cgaagactac    4620
aaggacgacg acccggccaa caagggaggc tgggtaggct ggtggaaggg cgatctggag    4680
cagctgcacg gctccaacat gatctcgcgc gtcacggtca tcctccgcga gtgtcgccac    4740
ttcctgctca tgttctacgt ggctacactc gagacgtccg acgtcatgta cgtggcgtac    4800
```

```
tcgttcggtg ctgcggtcgc gacgattgtt ctgcttggcg tgttccatgg ctttggtatg   4860
ggcatgcgct ccatgagccc ggtgacgcgc gctgtgatct acatggggac cgtcgcagcc   4920
atcgtgacgg cctacttctt ggccacttgg atcgtgctgg actggaaatt caagtacgcc   4980
atgtcgctct ggttcgccta cgtggctgcg ctctacggta tcaacgagtg cttccgcatg   5040
tggagtttcc caagctcgtc gatcgctggc attgctgtgt tccagcagct acagttcctc   5100
ttcgacttta tcttctgcat tggtatgatc atcccgcttg tggtcatgtc gtgcatcccg   5160
ttcctgaaca tcatccagac gcgtatgatg tacaacgaag gcttctccaa ggtcatgtct   5220
gcttcttcgc agtatgcctt ctctctggca gccttcatgg gaatcctggg cggtatcggt   5280
gtcggctggc tgttcaactt gctgtcaacg ctggagcagt ctgcgagttt cgcaagttac   5340
gtcgtcacgt acgatggcgt cctaagtgga aacgtgggcg atggcaccac gacgtacatg   5400
ctctacggtg cctgtgtggt gggtacgatc atcgctggct tcctcaactt cttcctgggt   5460
cgtcgtctgg ctattgttgc gggtggtctc ttcagtacgc tcggtatggt ggctgtcagt   5520
gccaacgacg atctccgttc gacgctgctg atgcctggta tcggtctgct tggagcctcg   5580
tgcggtattc tgctaccgtc gttggccatc tacatcttcg agatctcgac caaggagatg   5640
cgaggcaaag ccatgttgtt gctgggaatc ggcttcatca tcggcagttt gctgggcggc   5700
attttcgcga ccgtgaacca gctgggatgg atctggcaga cgtttgctgc ctgcatcgtg   5760
atcgccctgg tcacgccagt cgtcaatgtg ttcccagaga gtccgtactg ggtgctggat   5820
cgcaagggct gggacgcctg tgaagcctgt ctcgttatcc tgcgtcgtaa acctgatgtc   5880
caagaggagc tcaaggtcat gcgagaagag gaaacggcag atgaaggcgg cgccggcgcc   5940
tacaagttcc tcatcggtct cttcctcatg ctcgtgtcct ctctgactac tggtttcctc   6000
aacgccttca tcagctacaa gggagcgagc gagtacacgg accaagacca gctgttcgtg   6060
aacgcgatgg cgctgcagat ctccggtgct gcgatcgcca tcttctacat cgacaagctg   6120
gaccacaagt cgattctctt cggaacgttg atccctatcg ctatctgtgc tggcattctg   6180
ggcttcaacg agaactcaga gatgctggga gacaaagagg gctcgggtct gtacctcagt   6240
cttgtagtca tgctcatgta cttcttcatg gggctgggca cgagctctgc tctgtggtcc   6300
gcatgcgtcg gcatgttcaa tactcgcggc cgcgcctcgt ccaccaccat gctgttcgct   6360
atcttcttcc tggcggatat gggctacgtc tacttgcaca cggacgactc gatgatgcag   6420
aacgaatatt cctatctcta cgccatcgca ggcttcagtg tcgtcgccct ggtgctgtta   6480
atgggcgcag gcaccaagaa gaacggcgtc atctgtacca agtcagaagc tcagcgcgat   6540
cgcgaccgta tcgctcgtat gcgtgccgaa cgtgcaagtc gcaacacgcg gacgcctgga   6600
actgcgcgcc agcggaatct cagtcgcgtg cggtccaagt cgaacgctgg cggccagcgg   6660
ggcaacgcgg cgcatggcgg tggctaccaa atgtacgaaa cacccgccaa cgctgcgccg   6720
ccgctcatgc acgcgcgccc gtag                                         6744
```

<210> SEQ ID NO 37
<211> LENGTH: 2462
<212> TYPE: DNA
<213> ORGANISM: Phytophthora infestans

<400> SEQUENCE: 37

```
attcgagaga tttttcgaac tctgacatcg ttgcaaccat aacttgcctg cattaaggtg     60
ctcctcaact gtacccatgc cgagcaccca tcgactctgc cagtacgatg cttcaccaaa    120
gttttagtcc acaagaaaag ccgaaacgta catgtcgtaa cggaagccgt gcgacctttt    180
```

```
accgttcgtg cgctggtctc acgtagcttc attctccttc ttccctagcc agcaaaggcg      240
tctcccaaga tatcccagca attgtctatc ggttaagatc aaggagtaaa atgcactcgg      300
cgctgttctc gtgctcaact ttggctttga tcacgagttt ggtctcctca gagcgtgccg      360
actcgatgat caaatctcgg tctggattga gccctgggt ggacgttgac accccgaga       420 gtgcactcaa cgtcacgtcg tcgcgtggag atacgtggac gttggtcatg agcgacgaat      480
ttaacgttcc tgggcgtaat tttacgcccg gttcggatca catgtggacg gcgttagaaa      540
tgcccgacgg tgtcaatgca gctctcgaat actacagctt caatatgacc gataccgtaa      600
cggaatcgga cggtcgtggt gtcttccgga taaagattat ggaagaggac aacatcacct      660
acacggtgtg gaacacgtac gctaagcctg cgggtttcga gacccatcac atgtactacc      720
gagccggtat ggtgcaatcc tggaacaaat tctgtttcca aggaggaagg atggaagtgg      780
tggctcaatt accagcaaca accagctcta gtaaccccga tatgggtgac atcaaaggtc      840
gcgtcaagac aacagcttc tatcccacgt ggcctggtat ttggcttcta ggaaatctag       900
gacgagctct attctcccaa tcgaccagtc ggatgtggcc ttggagttac gacgaatgtg      960
acgaaaaatt cgaatccagt caaagaatca gtgcgtgtga cggtaatcca ggaagtggat     1020
tgaatgctca tcaaggacga ggagcgccgg aaatagatct actggaagga ggaggtgtag     1080
ccatctccac aagtatccag gtcgctcctg gaatgcccga taaattccgt atcattgctc     1140
ccacggatga taaaagtccc ttctgcgtct tcacggccga gtgtactact attggtgcta     1200
actttcctgg gatcccagcc aaagcgtacg aagctcgaga ttatgaaagc tggtatcaag     1260
gactacggta cgctccaaat actctttgta gcccagttgg cagcttgatg caagatccca     1320
aaacggtgct tgcaaatgcc gagaaaggct tcacttctaa tacgtgtaaa ggagtcaatg     1380
cgtgtccagc ttcgggtgac ggatactccg atttaggctt gatcgacggg aaagggcctg     1440
attactgggg ggttaacaaa gaaggcggct gtatgccggt tattaacgga tacacgggag     1500 cttttcctatg tgaccctgac agttccaaca aaaaatgttc ctctccgtta ggtgcggaag     1560
aacccaagag taaagttatg gaaccattcg agtatcagat ggacgccctg tccgctaatt     1620
ggccagttca gctcgcagca tatacaagtt atgtgaaata ccaagtcgaa tgggtcatgg     1680
gctcacaagg ttacattcgc tggatggtcg aggatattgt gattttgaa attccagccg      1740 agtcggtcga aatgttccca aagatgctg ccaagtccaa ccctaagaaa ctcatgttgg       1800
aagaacccat gtacgtgatt ttcaacgtcg ctctgtcaac tagttggggt accacgccac     1860
cgaatccagg gtcgccatgt cgtggagatg ggagcaatgc gcaacataac gctatttgtg     1920
acggtttccc catgttcatg aagatcgact acattcgtat ctatcaggat ctctcttcca     1980
actccacgat ggctatcggg tgtgacccgt ctactcatcc gactaaacaa tggatcgagg     2040
atcacattga tgagtatgag acgacggaga ataaatggat tgaggttcac ggtggagcca     2100
attgcaagac tgataacgac tgtacggtca gtacttctca cattttgacg gggaaatgta     2160
gcaagaaaca tcgctgtaga tgcggatctt ccggtgcttg gggtggtcca cgttgcacaa     2220
ctccactagc tgatacagcg aatggagaag gcttcggacc accaacagtt attacgagct     2280
tggttggtgc attcgtcatt gtgctttgg tctttgtggt gtacaagata atggaccaac      2340
gcagcaagaa ggcgatggtg ggagctggga ttactcaacc agcaattctc tccaagatcg     2400
agatggacga catcccacgt tcaaataaaa gccagagcgg ctcggaggat aaggtggtgt     2460
ag                                                                     2462
```

<210> SEQ ID NO 38
<211> LENGTH: 942
<212> TYPE: DNA
<213> ORGANISM: Phytophthora infestans

<400> SEQUENCE: 38
atggctccac tgccatccgc aaccttgacc acacccgacg tggctcctgt cacagctacc 60
accgcctcgc agcccttcga cgacctagtt gacaaggtcg agagtggcta tgcggctatg 120
cctaccaccc caaaggcggt ggctcccttc ccaacctcca aaccgcaagg tctccagcgt 180
ttcgccgttc agagcgtgca cctgcgcgag tgcttcgccg agttcctcgg caccttcgtc 240
atgatcgtct tcggtatggg cgtcaacaac caagtgacca actcacacga cgccaacggc 300
acgtggctca gcatcaatat gtgctggggg attggtgtac tcatcggcgt ctactgctcc 360
gagggcatca gtggtgctaa cctcaacaca gccgtgacgt tggcacattg cgtgtacggc 420
cgtctaccat ggtggaaagc acccggttac atgatctcac agctattggg cgccttctgt 480
ggagctttca ttatctacgt catgcagtac cagaacctca acgtcattga cccgtatcgc 540
gagaccacac agagcagctt ctcgacgtat ccgagcgaca acatctccaa ctacacagcc 600
ttctacaccg agttcatcgg tactgctatg cttgtgctca gtatctacgc catcacggac 660
aagcgcaaca gatctgccgg tctcgtgggt tctcccttcg ccttctgtct aatgatcatg 720
gcgttgggca tggcctttgg catgaacacg ggctacgctg tgaaccctgc acgtgacttc 780
ggcccccgca tcttcacggc catcgcgggc tggggctcca aggtctttac cactcggaac 840
tactacttct ggatcccgat cgtggccgat tctatgggcg gaattgctgg tgctggactc 900
tatcggctgc ttgtggagat ccaccaccca cccctctcgt ag 942

<210> SEQ ID NO 39
<211> LENGTH: 1636
<212> TYPE: DNA
<213> ORGANISM: Phytophthora infestans

<400> SEQUENCE: 39
atgtccgacg accaagtgcc accgttttcg ctcggtacga aacaccttac acgcatgacg 60
tgcagcgcac agttcagaga tgactaactg gccatgctgc cgctacgtgt atttaccaga 120
taagccgcgc cacgatactt cgacgtacgt cggtcggtgg cgtaagtttg cggagctcgt 180
gtcgccaaag tacgtcaaac aaggtagacg atggaaaaag tgtggctcta aacatcatgc 240
tggggcttta ggtggctctt tctaagctcg gagcagattc agcacgcgac gcagactctg 300
gaggacttcc gcaacggtaa aatcgcccct ggtcagttca aggatgcgga actttggaat 360
cttcgccagg gtacgaaaca atgcgacagg atggtaccaa cttgtggttt ttgctgacgt 420
tttggtgata attgaatcga tatgtagcgt acgaggctgc cgtgcaccct cagactggcg 480
agacagttcc ggctgtgttt cggctgtcgg ctttcgtgcc tgtgaacatt cccatttgcg 540
ttggcatgct gctcgctcct gccacggtat gtaaagtctt gctgcacttg taacaatagc 600
tttattttaa tttaaatgct cacttaaata tgcttacagt tgggaaacac gatcttctgg 660
caatgggtta accagagcta cagcgccggt ttcaactacg ctaaccgcaa cgccagcagt 720
gaacaggaca actccaccat cttcagtacg aagttctcga tgctaatggc cttctttcag 780
cgttctaaca cggctctttg catcgtatca cagagtcgta cgctaccgcg acgctcgtgt 840
cttgctcgac tgccgttggt ctgggtaaga tggtggagaa agccaagaga ctttctccca 900
gcacgcgttc cttcctcgga aaggttaaaa ctgctaaatg ccgaatgctg tgctccttat 960

```
gtgactgaat ttttgggctg caacttgatc agatggttcc tttcgttgct gtcgcgagcg    1020
caggtgcttt caacgccgtg tcgatgcgct tcaacgagtt ccagtacgtg tagagtgtct    1080
tgcactggaa atatgatgct gttgtgctca ttggagtgtg gtgatgcgtt acagagaggg    1140
aattgatatc atggacgagc acggagatgt tcacgggcgt tcagttgccg ctggacgtca    1200
gtcgcttggc caagtggcac tcacgcgtat tgcgctaccc atgcccagta cgtcctcgca    1260
ttgacaagct cttcttgggt gaattatgtc taatattggt ggacttggac agttttgctg    1320
ctcccgccgt acctgtatga gatcatgaag aaaaccaaca tcatgcccaa ggccaagtac    1380
ccgaagcttg ctgcggagct cggtacgtgc attatttctg ccatagtccg cggtaatgag    1440
ctaacttatt gcgtctctgc ctgcatctat gatagtcgtg ttaacgatgt gtctgtgggg    1500
tgccatgccc agcgctgtgg cgctcttccc gcagttggga acgatttcgg ctgacagcgt    1560
tgaggaggaa ttccgatctc gggtggatcg caacggccag cccattcgtc acttcatcta    1620
caacaaggga atctga                                                    1636

<210> SEQ ID NO 40
<211> LENGTH: 960
<212> TYPE: DNA
<213> ORGANISM: Phytophthora infestans

<400> SEQUENCE: 40
atgagcaccg ccaataaaga agcatctccc tttgtggagc ttcgccgtct taactttgcg     60
ttcgccaaag ttactatcgg tggccaactc atcaatcgct tgcagcatga ccccgctact    120
gctgacgcca tggaagacga cgatcgagtc ctgcgtgacg tgaatctaac gctgcagtct    180
ggtcagcgcc tgttggtcgt gggtggtaat ggagctggca aaagcacgct actcagtatc    240
ttggctggca agcacctgac ggctgacgac acggcgctga tcttcggtcg agacagcttc    300
cgtgacacga cactcaacgc tttaaggact ttcgttagtg ccgactgggg gcagcgctcg    360
gtggcgttcg caacgcacgc aatggcttac tcggctgaca tggcggtgga agaaatgatg    420
acgaaactgc agagtgaaca cccggagcga cgccaaaagt tactgaaggt gttgcgtatt    480
gacccaaagt ggcgtttaca tcgcctgtcg acggtcaac gtcgccgcgt tcagctcttt     540
ctggcgctac tgagaccttc gcagctcatc gtactggacg aagtgctggg aatgctcgac    600
atcatctcgc gcgaaaacgt actggcattc ctaaaggagg aaacagagac tcgacaagcc    660
acggtgttgc tagccacgca catcttcgat gggacggacg tctgggcatc tcatgtgctg    720
tatattcgtc gcggtactgt tgggttctat ggtccgattc agcagtgtac tgatggaggg    780
aagatcccga tgtataaggt ggtggaacac tggctacgtg aggaattggc cgacgacgac    840
cgtgtggaat gcgaggcggt gggcccaagt ggtgagttcg acctgggcaa cgcgcagaac    900
cgcgcaggag ggtatgccga cggtcgactg ggtggtgtcg atgtcaccac atcgttttaa    960

<210> SEQ ID NO 41
<211> LENGTH: 510
<212> TYPE: DNA
<213> ORGANISM: Phytophthora infestans

<400> SEQUENCE: 41
atgagcgacg gtactaagct cattgccgtg atcggagacg aagacaccgt cacgggcttt     60
atcctcgcgg gtgtcggcca tcgaacggcc gagggaacca actttctcgt cgtcaaaccc    120
tgtgcgtcgg cattcccgaa aggatttttt taaagcttag attaactact aacacgcgtc    180
```

| | |
|---|---|
| acatacgacg gtgctgcagc tactccaatc tccgctattg aggccagttt ccggacgctc | 240 |
| tcgagccgtg acgatatcgc aattatcctc atcaaccagc acgtacggca tcctagttag | 300 |
| aacccactct gaggtataag cctttatgtt tttctcactc gcttgatatt attgtttggg | 360 |
| caggttgctg aggagatccg tcaccttctc aacacgtacg acaagaccat cccacggtg | 420 |
| ctagagatcc cgagcaaaga ctcgccttac gacccagcta aggactatat catgaagcgc | 480 |
| gtgaatctca tgcttggagg agagtcgtga | 510 |

<210> SEQ ID NO 42
<211> LENGTH: 1491
<212> TYPE: DNA
<213> ORGANISM: Phytophthora infestans

<400> SEQUENCE: 42

| | |
|---|---|
| atggtcgctg aagacgcggt gttcacggaa gcgaagacgc ccaaggccgg cgatgtccag | 60 |
| gccggcagat ccgtcccgct ctcgccgacc ttctggttca gcctcgcggt gctgctcctg | 120 |
| ctccccttcc agttcggctg gtcggtcggc cagctcaacc tcacgacctt caacgacgaa | 180 |
| gacgagtgca acgcgcgacc tctagtcgac ggaacgtgcc tcatgtttcc cggtcatagc | 240 |
| agcacggaat ggaccttgat cgtgaacgcg tggattgtag cggtatgat cgggagtctc | 300 |
| ggttgtggcg ttatctccga acgtttcggt cgcaagaagg tattgctggc gaacgccgtc | 360 |
| gtcatgttgg ccggcgctgt cattcaagcg agtacgtcga gtatctcggt ttttatggtc | 420 |
| gggcgtatcg tcgccggtat cgcgtcgggt tgtgcgacgg gtatggtggg tggctacatc | 480 |
| agtgagatta caccccgag tctccgtaac tcgtacggca cgttcatgca ggtatctctc | 540 |
| tctgccggta tcttagtagt gaccatcagt ttttcttcg cggataccag tagcggctgg | 600 |
| aggtacatcg ccgcatttcc cgttcttaac gccggtttct tcttggcgtt cgcaccgttc | 660 |
| gttcttgtag agagtcccgc gtggcttttg gaaaagggcg accgggagca tgcggagcgg | 720 |
| gagatcgcca gactttacgg cttcgatttc gtcccagtag cactgacgtg gatgaaacca | 780 |
| ggtatcaata ctgacctgga gtcagaggaa ctgtgcggcg aacagcacga aggcggcaca | 840 |
| ttgtcgctgc tgttttcgcc gctctttatc aagcaactgc ttgtggctct tggtgtatca | 900 |
| gctgcgcaac aacttacggg tatcaacgcg gtgtgctatt actcgtccga tatcttctcg | 960 |
| gatgcaggga tgtcggatgg tcgtgtgggt ggcgtcatcg tgtacgtgct gatgttacta | 1020 |
| ccgacgatgg ctgttgcgcg attgtcggag cgattcggca accgacggct tctgcttact | 1080 |
| ggactggccg ggatgtttat tagtgctacg ggtataactt tggcgcttgc gttgtcggtc | 1140 |
| gaggtactct ctatcgtctt catgggtaca ttcgttgcgt tcttctctgc gagcgtgggg | 1200 |
| ccgcttatct agcctatcac ggccgcgctg ttcacggact cggtacgcgc cactgccgtc | 1260 |
| tctatgtgca tctttatcaa ttgggtatgc aacttgatca ttggcgtctg cttcccgtac | 1320 |
| gtctcggatg cgctagacga gtacaagttt gtcccctta tggtgaccac cgctgcgttt | 1380 |
| ttcttcttca ctcagttttg gatcccggag actgcaggta agagcaccga ggagatccaa | 1440 |
| gccacgttcc gatctaggaa agctcagaag ccggtggtgg tgttaagctg a | 1491 |

<210> SEQ ID NO 43
<211> LENGTH: 2462
<212> TYPE: DNA
<213> ORGANISM: Phytophthora infestans

<400> SEQUENCE: 43

| | |
|---|---|
| ttgtgctact c

-continued

| | | | |
|---|---|---|---|
| gcccccgcat | tagcagccta | catccactcg cgactgggtg catcgcacgg cgccatcgcg | 120 |
| tccatccgtc | agttccagca | tggccagtcc aacccgacgt acctcttgac aatggccggc | 180 |
| tcgaaagcca | agtgggtgtt | gcgtaagaag ccgcacggtc agatcctgcc gtcagctcac | 240 |
| gccgtagagc | gcgaatatcg | tgttctagag gctctggagc actcggaggt gcccgttccc | 300 |
| cgcgctgtgt | tgctatgtga | agaccccaaa gtcattggca cacctttcta cctcatggaa | 360 |
| tacatacatg | gtcgtatctt | ccaagaccca tcgctgcctg gcattaaacc tatgtatcgc | 420 |
| tacgccatgt | acagctcggc | agtagacgcg ttggttaagt tgcacgagct ggactacaag | 480 |
| aagatcggac | tggccgactt | cggtcgcccc gagaagtact gccaccgtgt cgtgacgcgc | 540 |
| tggagtcgac | aagtccaaag | tggccagaag gtctttagtg aagctggagt gaaggagaac | 600 |
| ccgaagatga | cgcagctgca | acgttggctg gagcagaacg ccgacgacgc cgagaaggcc | 660 |
| acgaccagtg | ccgagggagc | gagtatcgtc cacggagact tccgcattga caacatgatc | 720 |
| ttccacccga | cggagcctcg | tgtgttggcc attctggact gggagctgtg tactatcggc | 780 |
| aatccgttct | cggatgtagc | cacattggcg tcggcctaca gactgccact ggacaactcg | 840 |
| aacacaatca | tgacgcctgg | tctctcggat gctccgttga agacactcgg catcccatcg | 900 |
| gagagtgaat | tgttgctagg | ctactgtcgt cgtgccagac ggttccctct acccactcag | 960 |
| acgtggcatt | ttttcatggg | gatgatcgta taccgcttcg cagccatctg ccacggtgta | 1020 |
| tacgcccgcg | cactgctcgg | caacgcgtcg tcggccaacg cagcatgtgc caagacgacg | 1080 |
| atggaccgac | tcttggccat | gagcgacgac atcatggacg catcggctga tatttacccg | 1140 |
| gagccggagc | tgacgcacat | tctgccgttc ccgatccgtc ctcatgctct gcagatgtac | 1200 |
| aagaagctgc | taaagttttg | ccagaaccga gtgtaccccg ctgagtccgt ccacattgct | 1260 |
| cagatcgcca | aggcgagaga | agaaggacgg gagtggcaga gtgtgcctcc tgttattgaa | 1320 |
| gagctcaaga | cggaagccaa | ggcgctggga ctctggaacc tcttcctgcc tcagtgtgtg | 1380 |
| gtgccagctc | tggatggcaa | tggaccagac gtcaactacg gtggagacct gacgaatctc | 1440 |
| gagtacggac | tcatgtgtga | ggtcatggga cgctccattg tgttggctcc ggaggttttc | 1500 |
| aactgctcag | cacccgatac | cggcaacatg gagatcttga cgcggttctg cactgtggag | 1560 |
| cagaagcatc | agtggcttgt | tcctcttctt caaggtgaga tccgatcgtg tttcgcgatg | 1620 |
| acggagaagc | gtgtggcttc | gtcggatgcg acgaacatcg agacgcgcat tgtacgcgac | 1680 |
| gaacagcgtc | aagaatacgt | catcaatggc cacaagttct acatctctgg agctggagac | 1740 |
| ccacgatgca | agatcattgt | gctcatgggc aagcacacgg aacgagccaa ggagagtcca | 1800 |
| ttcaagcagc | agtcgatgat | cctcgtgcct atggacacac ccggcgtgca ggtcgtgaag | 1860 |
| cccatgcatg | tctttggcta | cgacgacgca ccgcacggac acatggagat gctgttcaag | 1920 |
| gacgtgcgtg | tgccgttcag | caacgtgttg ctcggtgaag gtcgcggctt tgagatcgct | 1980 |
| caggctcgtc | ttggacctgg | ccgtatccac cactgtatgc gagccatcgg agctgctgag | 2040 |
| cgttgtcttg | agctgatggt | gcagcgagcc aagacacgca cagcgttcaa gcagctcctg | 2100 |
| gccgagaatc | cgctcgtgtg | ttcgcagatt gccaagtcgc gttgtgaatt ggacagcgcg | 2160 |
| cgcttgttga | cgctccaggc | tgcacatcag atggacaagc acggcaacaa ggtggcgcaa | 2220 |
| caggccatcg | ctatgatcaa | gatcgtggcg cctaacatgg cactggacgt ctgcgaccga | 2280 |

```
gccatccaga tccacggcgc ttctggcgtg agtcaggact ttgtcctgtc ttacttgtac    2340
gccgccctgc gcacgctacg tatcgccgac ggaccggatg aagtgcacat gcggaccatc    2400
gcaaaactcg agctgagcca ctcgaagttg taagagaaat gtaaggcaaa agcaagcgtg    2460
aa                                                                   2462
```

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

```
atcccactat ccttcgcaag                                                  20
```

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

```
ttgatatcgc ggaaggcgag agacatcg                                         28
```

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
ctaagggttt cttatatgct caac                                             24
```

<210> SEQ ID NO 47
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

```
cgctcgaggc tggatctcgc gctgaggt                                         28
```

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

```
gtggagaggc tattcggta                                                   19
```

<210> SEQ ID NO 49
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 49
ccaccatgat attcggcaag                                                    20
```